United States Patent
Collins, Jr. et al.

(10) Patent No.: US 9,734,293 B2
(45) Date of Patent: *Aug. 15, 2017

(54) SYSTEM AND METHOD FOR ASSOCIATION OF PATIENT CARE DEVICES TO A PATIENT

(71) Applicant: Hill-Rom Services, Inc., Batesville, IN (US)

(72) Inventors: Williams F. Collins, Jr., Columbus, IN (US); Michael D. Gallup, Holly Springs, NC (US)

(73) Assignee: Hill-Rom Services, Inc., Batesville, IN (US)

(*) Notice: Subject to any disclaimer, the term of this patent is extended or adjusted under 35 U.S.C. 154(b) by 223 days.

This patent is subject to a terminal disclaimer.

(21) Appl. No.: 14/305,013

(22) Filed: Jun. 16, 2014

(65) Prior Publication Data
US 2014/0297310 A1   Oct. 2, 2014

Related U.S. Application Data

(63) Continuation of application No. 13/303,624, filed on Nov. 23, 2011, now Pat. No. 8,756,078, which is a
(Continued)

(51) Int. Cl.
*G06Q 50/00* (2012.01)
*G06F 19/00* (2011.01)
(Continued)

(52) U.S. Cl.
CPC .......... *G06F 19/3406* (2013.01); *A61B 5/002* (2013.01); *G06F 19/327* (2013.01);
(Continued)

(58) Field of Classification Search
CPC ...... G06F 19/3406; H04L 67/12; A61B 5/002
See application file for complete search history.

(56) References Cited

U.S. PATENT DOCUMENTS 2,330,356 A    9/1943  Belliveau
2,335,524 A   11/1943  Lomax
(Continued)

FOREIGN PATENT DOCUMENTS

DE   10 2006 056 723 B3   7/2007
EP         0 601 589 A2   6/1994
(Continued)

OTHER PUBLICATIONS

International Search Report Written Opinion for PCT/US2008/081049 completed Dec. 24, 2008.
(Continued)

*Primary Examiner* — Christopher L Gilligan
(74) *Attorney, Agent, or Firm* — Barnes & Thornburg LLP

(57) ABSTRACT

A system and method for collecting, communicating, displaying, and/or analyzing data from multiple medical devices is disclosed. The system includes a local data collection module and a number of medical device adapters. The medical device adapters are coupled to respective medical devices via hardwired connections to receive data from the respective medical devices. The medical device adapters wirelessly transmit the data to the local data collection module. The local data collection module communicates the data received from the medical device adapters to an Electronic Medical Records (EMR) system for automatic entry of at least some of the data in the electronic medical record of a patient associated with the medical devices.

20 Claims, 22 Drawing Sheets

Related U.S. Application Data continuation of application No. 12/256,637, filed on Oct. 23, 2008, now Pat. No. 8,082,160.

(60) Provisional application No. 61/000,489, filed on Oct. 26, 2007, provisional application No. 61/106,830, filed on Oct. 20, 2008.

(51) Int. Cl.

| *G06Q 50/22* | (2012.01) |
|---|---|
| *G06Q 50/24* | (2012.01) |
| *H04L 29/08* | (2006.01) |
| *H04L 29/06* | (2006.01) |
| *A61B 5/00* | (2006.01) |
| *A61B 5/0205* | (2006.01) |
| *A61B 5/021* | (2006.01) |
| *A61B 17/00* | (2006.01) |
| *A61B 34/00* | (2016.01) |

(52) U.S. Cl.
CPC ......... *G06F 19/3418* (2013.01); *G06Q 50/22* (2013.01); *G06Q 50/24* (2013.01); *H04L 67/12* (2013.01); *H04L 67/125* (2013.01); *H04L 69/18* (2013.01); *A61B 5/021* (2013.01); *A61B 5/0205* (2013.01); *A61B 2017/00221* (2013.01); *A61B 2034/256* (2016.02); *G06F 19/322* (2013.01)

(56) References Cited

U.S. PATENT DOCUMENTS

| | | |
|---|---|---|
| 2,736,888 A | 2/1956 | McLain |
| 2,896,021 A | 7/1959 | Philipps |
| 3,098,220 A | 7/1963 | De Graaf |
| 3,439,320 A | 4/1969 | Ward |
| 3,478,344 A | 11/1969 | Schwitzgebel et al. |
| 3,553,383 A | 1/1971 | Rochtus |
| 3,599,199 A | 8/1971 | Bunting |
| 3,599,200 A | 8/1971 | Bunting |
| 3,696,384 A | 10/1972 | Lester |
| 3,739,329 A | 6/1973 | Lester |
| 3,767,859 A | 10/1973 | Doering et al. |
| 3,805,265 A | 4/1974 | Lester |
| 3,913,153 A | 10/1975 | Adams et al. |
| 3,973,200 A | 8/1976 | Akerberg |
| 4,067,005 A | 1/1978 | Levy et al. |
| 4,150,284 A | 4/1979 | Trenkler et al. |
| 4,151,407 A | 4/1979 | McBride et al. |
| 4,183,015 A | 1/1980 | Drew et al. |
| 4,216,462 A | 8/1980 | McGrath et al. |
| 4,225,953 A | 9/1980 | Simon et al. |
| 4,228,426 A | 10/1980 | Roberts |
| 4,237,344 A | 12/1980 | Moore |
| 4,264,982 A | 4/1981 | Sakarya |
| 4,275,385 A | 6/1981 | White |
| 4,279,433 A | 7/1981 | Petaja |
| 4,298,863 A | 11/1981 | Natitus et al. |
| 4,331,953 A | 5/1982 | Blevins et al. |
| 4,356,475 A | 10/1982 | Neumann et al. |
| 4,418,334 A | 11/1983 | Burnett |
| 4,455,548 A | 6/1984 | Burnett |
| 4,489,387 A | 12/1984 | Lamb et al. |
| 4,495,495 A | 1/1985 | Ormanns et al. |
| 4,495,496 A | 1/1985 | Miller, III |
| 4,539,560 A | 9/1985 | Fleck et al. |
| 4,577,185 A | 3/1986 | Andersen |
| 4,578,671 A | 3/1986 | Flowers |
| 4,582,280 A | 4/1986 | Nichols et al. |
| 4,593,273 A | 6/1986 | Narcisse |
| 4,598,275 A | 7/1986 | Ross et al. |
| 4,601,064 A | 7/1986 | Shipley |
| 4,649,385 A | 3/1987 | Aires et al. |
| 4,680,790 A | 7/1987 | Packard et al. |
| 4,709,330 A | 11/1987 | Yokoi et al. |
| 4,740,788 A | 4/1988 | Konneker |
| 4,752,951 A | 6/1988 | Konneker |
| 4,792,798 A | 12/1988 | Wilowski |
| 4,795,905 A | 1/1989 | Zierhut |
| 4,814,751 A | 3/1989 | Hawkins et al. |
| 4,833,452 A | 5/1989 | Currier |
| 4,833,467 A | 5/1989 | Kobayashi et al. |
| 4,837,568 A | 6/1989 | Snaper |
| 4,853,692 A | 8/1989 | Wolk et al. |
| 4,899,135 A | 2/1990 | Ghahariiran |
| 4,947,152 A | 8/1990 | Hodges |
| 4,955,000 A | 9/1990 | Nastrom |
| 4,967,195 A | 10/1990 | Shipley |
| 4,990,892 A | 2/1991 | Guest et al. |
| 4,998,095 A | 3/1991 | Shields |
| 4,998,939 A | 3/1991 | Potthast et al. |
| 5,003,984 A | 4/1991 | Muraki et al. |
| 5,006,830 A | 4/1991 | Merritt |
| 5,027,314 A | 6/1991 | Linwood et al. |
| 5,041,086 A | 8/1991 | Koenig et al. |
| 5,062,151 A | 10/1991 | Shipley |
| 5,065,154 A | 11/1991 | Kaiser et al. |
| 5,086,290 A | 2/1992 | Murray et al. |
| 5,103,108 A | 4/1992 | Crimmins |
| 5,124,991 A | 6/1992 | Allen |
| 5,137,033 A | 8/1992 | Norton |
| 5,153,584 A | 10/1992 | Engira |
| 5,228,449 A | 7/1993 | Christ et al. |
| 5,266,944 A | 11/1993 | Carroll et al. |
| 5,291,399 A | 3/1994 | Chaco |
| 5,319,355 A | 6/1994 | Russek |
| 5,319,363 A | 6/1994 | Welch et al. |
| 5,357,254 A | 10/1994 | Kah, Jr. |
| 5,375,604 A | 12/1994 | Kelly et al. |
| 5,394,882 A | 3/1995 | Mawhinney |
| 5,396,224 A | 3/1995 | Dukes et al. |
| 5,396,227 A | 3/1995 | Carroll et al. |
| 5,416,695 A | 5/1995 | Stutman et al. |
| 5,434,775 A | 7/1995 | Sims et al. |
| 5,446,678 A | 8/1995 | Saltzstein et al. |
| 5,455,560 A | 10/1995 | Owen |
| 5,458,123 A | 10/1995 | Unger |
| 5,461,390 A | 10/1995 | Hoshen |
| 5,475,367 A | 12/1995 | Prevost |
| 5,511,553 A | 4/1996 | Segalowitz |
| 5,534,851 A | 7/1996 | Russek |
| 5,537,459 A | 7/1996 | Price et al. |
| 5,544,661 A | 8/1996 | Davis et al. |
| 5,548,637 A | 8/1996 | Heller et al. |
| 5,549,113 A | 8/1996 | Halleck et al. |
| 5,561,412 A | 10/1996 | Novak et al. |
| 5,568,119 A | 10/1996 | Schipper et al. |
| 5,576,952 A | 11/1996 | Stutman et al. |
| 5,579,001 A | 11/1996 | Dempsey et al. |
| 5,579,775 A | 12/1996 | Dempsey et al. |
| 5,588,005 A | 12/1996 | Ali et al. |
| 5,594,786 A | 1/1997 | Chaco et al. |
| 5,621,388 A | 4/1997 | Sherburne et al. |
| 5,628,324 A | 5/1997 | Sarbach |
| 5,635,907 A | 6/1997 | Bernard et al. |
| 5,636,245 A | 6/1997 | Ernst et al. |
| 5,640,953 A | 6/1997 | Bishop et al. |
| 5,650,769 A | 7/1997 | Campana, Jr. |
| 5,650,770 A | 7/1997 | Schlager et al. |
| 5,664,270 A | 9/1997 | Bell et al. |
| 5,678,562 A | 10/1997 | Sellers |
| 5,682,139 A | 10/1997 | Pradeep et al. |
| 5,686,888 A | 11/1997 | Welles, II et al. |
| 5,686,902 A | 11/1997 | Reis et al. |
| 5,687,734 A | 11/1997 | Dempsey et al. |
| 5,689,229 A | 11/1997 | Chaco et al. |
| 5,691,980 A | 11/1997 | Welles, II et al. |
| 5,699,038 A | 12/1997 | Ulrich et al. |
| 5,705,980 A | 1/1998 | Shapiro |
| 5,708,421 A | 1/1998 | Boyd |
| 5,712,795 A | 1/1998 | Layman et al. |
| 5,713,856 A | 2/1998 | Eggers et al. |
| 5,719,761 A | 2/1998 | Gatti et al. |

(56) References Cited

U.S. PATENT DOCUMENTS

| | | |
|---|---|---|
| 5,724,025 A | 3/1998 | Tavori |
| 5,731,757 A | 3/1998 | Layson, Jr. |
| 5,742,237 A | 4/1998 | Bledsoe |
| 5,751,246 A | 5/1998 | Hertel |
| 5,752,917 A | 5/1998 | Fuchs |
| 5,760,704 A | 6/1998 | Barton et al. |
| 5,767,791 A | 6/1998 | Stoop et al. |
| 5,781,442 A | 7/1998 | Engleson et al. |
| 5,793,290 A | 8/1998 | Eagleson et al. |
| 5,800,387 A | 9/1998 | Duffy et al. |
| 5,808,564 A | 9/1998 | Simms et al. |
| 5,812,056 A | 9/1998 | Law |
| 5,822,418 A | 10/1998 | Yacenda et al. |
| 5,822,544 A | 10/1998 | Chaco et al. |
| 5,825,283 A | 10/1998 | Camhi |
| 5,836,910 A | 11/1998 | Duffy et al. |
| 5,838,223 A | 11/1998 | Gallant et al. |
| 5,844,488 A | 12/1998 | Musick |
| 5,862,803 A | 1/1999 | Besson et al. |
| 5,867,821 A | 2/1999 | Ballantyne et al. |
| 5,873,369 A | 2/1999 | Laniado et al. |
| 5,877,675 A | 3/1999 | Rebstock et al. |
| 5,919,141 A | 7/1999 | Money et al. |
| 5,933,488 A | 8/1999 | Marcus et al. |
| 5,936,539 A | 8/1999 | Fuchs |
| 5,941,846 A | 8/1999 | Duffy et al. |
| 5,942,986 A | 8/1999 | Shabot et al. |
| 5,944,659 A | 8/1999 | Flach et al. |
| 5,957,854 A | 9/1999 | Beeson et al. |
| 5,963,137 A | 10/1999 | Waters, Sr. |
| 5,974,389 A | 10/1999 | Clark et al. |
| 5,990,866 A | 11/1999 | Yollin |
| 5,991,728 A | 11/1999 | DeBusk et al. |
| 5,995,937 A | 11/1999 | DeBusk et al. |
| 6,014,346 A | 1/2000 | Malone |
| 6,014,633 A | 1/2000 | DeBusk et al. |
| 6,038,469 A | 3/2000 | Karlsson et al. |
| 6,044,283 A | 3/2000 | Fein et al. |
| 6,044,382 A | 3/2000 | Martino |
| 6,047,203 A | 4/2000 | Sackner et al. |
| 6,057,758 A | 5/2000 | Dempsey et al. |
| 6,057,782 A | 5/2000 | Koenig |
| 6,067,019 A | 5/2000 | Scott |
| 6,074,345 A | 6/2000 | van Oostrom et al. |
| 6,076,166 A | 6/2000 | Moshfeghi et al. |
| 6,080,106 A | 6/2000 | Lloyd et al. |
| 6,085,493 A | 7/2000 | DeBusk et al. |
| 6,088,362 A | 7/2000 | Turnbull et al. |
| 6,093,146 A | 7/2000 | Filangeri |
| 6,097,308 A | 8/2000 | Albert et al. |
| 6,128,512 A | 10/2000 | Trompower et al. |
| 6,132,371 A | 10/2000 | Dempsey et al. |
| 6,133,837 A | 10/2000 | Riley |
| 6,147,592 A | 11/2000 | Ulrich et al. |
| 6,147,618 A | 11/2000 | Halleck et al. |
| 6,150,951 A | 11/2000 | OleJniczak |
| 6,159,147 A | 12/2000 | Lichter et al. |
| 6,160,478 A | 12/2000 | Jacobsen et al. |
| 6,167,258 A | 12/2000 | Schmidt et al. |
| 6,171,264 B1 | 1/2001 | Bader |
| 6,183,417 B1 | 2/2001 | Geheb et al. |
| 6,186,962 B1 | 2/2001 | Lloyd et al. |
| 6,198,394 B1 | 3/2001 | Jacobsen et al. |
| 6,208,250 B1 | 3/2001 | Dixon et al. |
| 6,213,942 B1 | 4/2001 | Flach et al. |
| 6,241,668 B1 | 6/2001 | Herzog |
| 6,259,355 B1 | 7/2001 | Chaco et al. |
| 6,264,614 B1 | 7/2001 | Albert et al. |
| 6,270,457 B1 | 8/2001 | Bardy |
| 6,277,080 B1 | 8/2001 | Nissila et al. |
| 6,279,183 B1 | 8/2001 | Kummer et al. |
| 6,287,253 B1 | 9/2001 | Ortega et al. |
| 6,289,238 B1 | 9/2001 | Besson et al. |
| 6,302,844 B1 | 10/2001 | Walker et al. |
| 6,304,774 B1 | 10/2001 | Gorman |
| 6,314,556 B1 | 11/2001 | DeBusk et al. |
| 6,320,510 B2 | 11/2001 | Menkedick et al. |
| 6,336,900 B1 | 1/2002 | Alleckson et al. |
| 6,336,903 B1 | 1/2002 | Bardy |
| 6,344,794 B1 | 2/2002 | Ulrich et al. |
| 6,348,777 B1 | 2/2002 | Brown et al. |
| 6,362,725 B1 | 3/2002 | Ulrich et al. |
| 6,364,834 B1 | 4/2002 | Reuss et al. |
| 6,368,284 B1 | 4/2002 | Bardy |
| 6,398,727 B1 | 6/2002 | Bui et al. |
| 6,398,728 B1 | 6/2002 | Bardy |
| 6,402,691 B1 | 6/2002 | Peddicord et al. |
| 6,406,426 B1 | 6/2002 | Reuss et al. |
| 6,407,335 B1 | 6/2002 | Franklin-Lees et al. |
| 6,411,840 B1 | 6/2002 | Bardy |
| 6,412,980 B1 | 7/2002 | Lounsberry et al. |
| 6,416,471 B1 | 7/2002 | Kumar et al. |
| 6,421,649 B1 | 7/2002 | Rattner |
| 6,439,769 B1 | 8/2002 | Polkus et al. |
| 6,441,742 B1 | 8/2002 | Lovely et al. |
| 6,441,747 B1 | 8/2002 | Khair et al. |
| 6,442,290 B1 | 8/2002 | Ellis et al. |
| 6,443,890 B1 | 9/2002 | Schulze et al. |
| 6,445,299 B1 | 9/2002 | Rojas, Jr. |
| 6,450,953 B1 | 9/2002 | Place et al. |
| 6,450,956 B1 | 9/2002 | Rappaport et al. |
| 6,462,656 B2 | 10/2002 | Ulrich et al. |
| 6,475,153 B1 | 11/2002 | Khair et al. |
| 6,486,792 B1 | 11/2002 | Moster et al. |
| 6,493,568 B1 | 12/2002 | Bell et al. |
| 6,493,747 B2 | 12/2002 | Simmon et al. |
| 6,494,829 B1 | 12/2002 | New, Jr. et al. |
| 6,494,831 B1 | 12/2002 | Koritzinsky |
| 6,496,705 B1 | 12/2002 | Ng et al. |
| 6,497,656 B1 | 12/2002 | Evans et al. |
| 6,510,344 B1 | 1/2003 | Halpern |
| 6,516,324 B1 | 2/2003 | Jones et al. |
| 6,517,497 B2 | 2/2003 | Rymut et al. |
| 6,526,310 B1 | 2/2003 | Carter et al. |
| 6,529,164 B1 | 3/2003 | Carter |
| 6,533,453 B1 | 3/2003 | Heidsieck et al. |
| 6,533,729 B1 | 3/2003 | Khair et al. |
| 6,535,576 B2 | 3/2003 | Vafi et al. |
| 6,540,686 B2 | 4/2003 | Heikkila et al. |
| 6,544,173 B2 | 4/2003 | West et al. |
| 6,544,174 B2 | 4/2003 | West et al. |
| 6,551,243 B2 | 4/2003 | Bocionek et al. |
| 6,551,252 B2 | 4/2003 | Sackner et al. |
| 6,553,106 B1 | 4/2003 | Gould et al. |
| 6,554,174 B1 | 4/2003 | Aceves |
| 6,556,630 B1 | 4/2003 | Brinsfield et al. |
| 6,559,620 B2 | 5/2003 | Zhou et al. |
| 6,560,274 B1 | 5/2003 | Leitgeb et al. |
| 6,569,094 B2 | 5/2003 | Suzuki et al. |
| 6,572,556 B2 | 6/2003 | Stoycos et al. |
| 6,575,901 B2 | 6/2003 | Stoycos et al. |
| 6,575,902 B1 | 6/2003 | Burton |
| 6,577,893 B1 | 6/2003 | Besson et al. |
| 6,579,231 B1 | 6/2003 | Phipps |
| 6,581,204 B2 | 6/2003 | DeBusk et al. |
| 6,584,182 B2 | 6/2003 | Brodnick |
| 6,584,454 B1 | 6/2003 | Hummel, Jr. et al. |
| 6,585,645 B2 | 7/2003 | Hutchinson |
| 6,589,170 B1 | 7/2003 | Flach et al. |
| 6,593,528 B2 | 7/2003 | Franklin-Lees et al. |
| 6,594,146 B2 | 7/2003 | Frangesch et al. |
| 6,594,511 B2 | 7/2003 | Stone et al. |
| 6,594,519 B2 | 7/2003 | Stoycos et al. |
| 6,595,929 B2 | 7/2003 | Stivoric et al. |
| 6,600,421 B2 | 7/2003 | Freeman |
| 6,602,191 B2 | 8/2003 | Quy |
| 6,603,401 B1 | 8/2003 | Ueyama |
| 6,603,494 B1 | 8/2003 | Banks et al. |
| 6,605,038 B1 | 8/2003 | Teller et al. |
| 6,609,115 B1 | 8/2003 | Mehring et al. |
| 6,611,705 B2 | 8/2003 | Hopman et al. |
| 6,612,984 B1 | 9/2003 | Kerr, II |
| 6,616,606 B1 | 9/2003 | Petersen et al. |
| 6,622,088 B2 | 9/2003 | Hood |

(56) References Cited

U.S. PATENT DOCUMENTS

| | | | |
|---|---|---|---|
| 6,640,246 B1 | 10/2003 | Gary, Jr. et al. |
| 6,643,238 B2 | 11/2003 | Nakajima |
| 6,650,346 B1 | 11/2003 | Jaeger et al. |
| 6,659,947 B1 | 12/2003 | Carter et al. |
| 6,665,385 B2 | 12/2003 | Rogers et al. |
| 6,665,820 B1 | 12/2003 | Frowein et al. |
| 6,669,630 B1 | 12/2003 | Joliat et al. |
| 6,671,547 B2 | 12/2003 | Lyster et al. |
| 6,671,563 B1 | 12/2003 | Engelson et al. |
| 6,685,633 B2 | 2/2004 | Albert et al. |
| 6,689,091 B2 | 2/2004 | Bui et al. |
| 6,694,180 B1 | 2/2004 | Boesen |
| 6,694,367 B1 | 2/2004 | Miesbauer et al. |
| 6,694,509 B1 | 2/2004 | Stoval et al. |
| 6,697,765 B2 | 2/2004 | Kuth |
| 6,707,476 B1 | 3/2004 | Hochstedler |
| 6,714,913 B2 | 3/2004 | Brandt et al. |
| 6,721,818 B1 | 4/2004 | Nakamura |
| 6,723,046 B2 | 4/2004 | Lichtenstein et al. |
| 6,726,634 B2 | 4/2004 | Freeman |
| 6,727,818 B1 | 4/2004 | Wildman et al. |
| 6,731,311 B2 | 5/2004 | Bufe et al. |
| 6,731,989 B2 | 5/2004 | Engleson et al. |
| 6,736,759 B1 | 5/2004 | Stubbs et al. |
| 6,740,033 B1 | 5/2004 | Olejniczak et al. |
| 6,748,250 B1 | 6/2004 | Berman et al. |
| 6,749,566 B2 | 6/2004 | Russ |
| 6,751,630 B1 | 6/2004 | Franks et al. |
| 6,754,545 B2 | 6/2004 | Haeuser et al. |
| 6,754,883 B2 | 6/2004 | DeBusk et al. |
| 6,758,812 B2 | 7/2004 | Lang |
| 6,759,959 B2 | 7/2004 | Wildman |
| 6,763,541 B2 | 7/2004 | Mahoney et al. |
| 6,771,172 B1 | 8/2004 | Robinson et al. |
| 6,773,396 B2 | 8/2004 | Flach et al. |
| 6,778,225 B2 | 8/2004 | David |
| 6,781,517 B2 | 8/2004 | Moster et al. |
| 6,784,797 B2 | 8/2004 | Smith et al. |
| 6,791,460 B2 | 9/2004 | Dixon et al. |
| 6,792,396 B2 | 9/2004 | Inda et al. |
| 6,801,227 B2 | 10/2004 | Bocionek et al. |
| 6,807,543 B2 | 10/2004 | Muthya |
| 6,817,979 B2 | 11/2004 | Nihtila |
| 6,819,247 B2 | 11/2004 | Birnbach et al. |
| 6,823,036 B1 | 11/2004 | Chen |
| 6,825,763 B2 | 11/2004 | Ulrich et al. |
| 6,826,578 B2 | 11/2004 | Brackett et al. |
| 6,828,992 B1 | 12/2004 | Freeman et al. |
| 6,829,796 B2 | 12/2004 | Salvatini et al. |
| 6,830,549 B2 | 12/2004 | Bui et al. |
| 6,832,199 B1 | 12/2004 | Kucek et al. |
| 6,840,117 B2 | 1/2005 | Hubbard, Jr. |
| 6,840,904 B2 | 1/2005 | Goldberg |
| 6,847,814 B1 | 1/2005 | Vogeleisen |
| 6,868,256 B2 | 3/2005 | Dooley et al. |
| 6,870,466 B2 | 3/2005 | Rust et al. |
| 6,871,211 B2 | 3/2005 | Labounty et al. |
| 6,873,884 B2 | 3/2005 | Brackett et al. |
| 6,875,174 B2 | 4/2005 | Braun et al. |
| 6,876,985 B2 | 4/2005 | Kawanaka |
| 6,885,288 B2 | 4/2005 | Pincus |
| 6,891,909 B2 | 5/2005 | Hurley et al. |
| 6,893,396 B2 | 5/2005 | Schulze et al. |
| 6,897,788 B2 | 5/2005 | Khair et al. |
| 6,904,161 B1 | 6/2005 | Becker et al. |
| 6,909,995 B2 | 6/2005 | Shiraishi |
| 6,912,549 B2 | 6/2005 | Rotter et al. |
| 6,915,170 B2 | 7/2005 | Engleson et al. |
| 6,925,367 B2 | 8/2005 | Fontius |
| 6,930,878 B2 | 8/2005 | Brackett et al. |
| 6,937,150 B2 | 8/2005 | Medema et al. |
| 6,942,616 B2 | 9/2005 | Kerr, II |
| 6,984,297 B2 | 1/2006 | Nisch et al. |
| 6,987,448 B2 | 1/2006 | Catton et al. |
| 6,987,965 B2 | 1/2006 | Ng et al. |
| 6,988,989 B2 | 1/2006 | Weiner et al. |
| 7,002,468 B2 | 2/2006 | Eveland et al. |
| 7,004,907 B2 | 2/2006 | Banet et al. |
| 7,010,337 B2 | 3/2006 | Furnary et al. |
| 7,020,508 B2 | 3/2006 | Stivoric et al. |
| 7,029,455 B2 | 4/2006 | Flaherty |
| 7,053,767 B2 | 5/2006 | Petite et al. |
| 7,053,831 B2 | 5/2006 | Dempsey et al. |
| 7,068,143 B2 | 6/2006 | Doering et al. |
| 7,088,233 B2 | 8/2006 | Menard |
| 7,099,895 B2 | 8/2006 | Dempsey |
| 7,103,407 B2 | 9/2006 | Hjelt et al. |
| 7,103,511 B2 | 9/2006 | Petite |
| 7,104,955 B2 | 9/2006 | Bardy |
| 7,107,106 B2 | 9/2006 | Engleson et al. |
| 7,117,041 B2 | 10/2006 | Engleson et al. |
| 7,123,149 B2 | 10/2006 | Nowak et al. |
| 7,127,261 B2 | 10/2006 | Van Erlach |
| 7,129,836 B2 | 10/2006 | Lawson et al. |
| 7,130,396 B2 | 10/2006 | Rogers et al. |
| 7,138,902 B2 | 11/2006 | Menard |
| 7,151,435 B2 * | 12/2006 | Brackett ............... G06K 17/00 340/5.62 |
| 7,153,262 B2 | 12/2006 | Stivoric et al. |
| 7,153,263 B2 | 12/2006 | Carter et al. |
| 7,154,398 B2 | 12/2006 | Chen et al. |
| 7,156,807 B2 | 1/2007 | Carter et al. |
| 7,171,166 B2 | 1/2007 | Ng et al. |
| 7,197,357 B2 | 3/2007 | Istvan et al. |
| 7,197,492 B2 | 3/2007 | Sullivan |
| 7,215,991 B2 | 5/2007 | Beeson et al. |
| 7,222,054 B2 | 5/2007 | Geva |
| 7,231,258 B2 | 6/2007 | Moore et al. |
| 7,256,708 B2 | 8/2007 | Rosenfeld et al. |
| 7,272,428 B2 | 9/2007 | Hopman et al. |
| 7,277,758 B2 | 10/2007 | DiLorenzo |
| 7,283,423 B2 | 10/2007 | Holm et al. |
| 7,292,135 B2 | 11/2007 | Bixler et al. |
| 7,292,139 B2 | 11/2007 | Mazar et al. |
| 7,294,105 B1 | 11/2007 | Islam |
| 7,301,451 B2 | 11/2007 | Hastings |
| 7,304,580 B2 | 12/2007 | Sullivan et al. |
| 7,319,386 B2 | 1/2008 | Collins et al. |
| 7,324,824 B2 | 1/2008 | Smith et al. |
| 7,336,563 B2 | 2/2008 | Holm |
| 7,352,652 B2 | 4/2008 | Holm et al. |
| 7,362,656 B2 | 4/2008 | Holm |
| 7,384,110 B2 | 6/2008 | Hoshiyama et al. |
| 7,461,425 B2 | 12/2008 | Chambers et al. |
| 7,468,661 B2 | 12/2008 | Petite et al. |
| 7,697,492 B2 | 4/2010 | Petite |
| 7,852,208 B2 | 12/2010 | Collins, Jr. et al. |
| 7,868,740 B2 | 1/2011 | McNeely et al. |
| 8,001,235 B2 | 8/2011 | Russ et al. |
| 8,031,057 B2 | 10/2011 | McNeely et al. |
| 8,082,160 B2 | 12/2011 | Collins, Jr. et al. |
| 8,604,916 B2 | 12/2013 | McNeely et al. |
| 8,756,078 B2 | 6/2014 | Collins, Jr. et al. |
| 2001/0034475 A1 | 10/2001 | Flach et al. |
| 2001/0050610 A1 | 12/2001 | Gelston |
| 2001/0051765 A1 | 12/2001 | Walker et al. |
| 2002/0014951 A1 | 2/2002 | Kramer et al. |
| 2002/0044043 A1 | 4/2002 | Chaco et al. |
| 2002/0044059 A1 | 4/2002 | Reeder et al. |
| 2002/0067273 A1 | 6/2002 | Jaques et al. |
| 2002/0070867 A1 | 6/2002 | Conway et al. |
| 2002/0080037 A1 | 6/2002 | Dixon et al. |
| 2002/0103674 A1 | 8/2002 | Reeder et al. |
| 2002/0151990 A1 | 10/2002 | Ulrich et al. |
| 2002/0165731 A1 | 11/2002 | Dempsey |
| 2002/0173991 A1 | 11/2002 | Avitall |
| 2002/0186136 A1 | 12/2002 | Schuman |
| 2002/0196141 A1 | 12/2002 | Boone et al. |
| 2002/0198986 A1 | 12/2002 | Dempsey |
| 2003/0010345 A1 | 1/2003 | Koblasz et al. |
| 2003/0028449 A1 | 2/2003 | Heinen et al. |
| 2003/0030569 A1 | 2/2003 | Ulrich et al. |
| 2003/0052787 A1 | 3/2003 | Zerhusen et al. |
| 2003/0074222 A1 | 4/2003 | Rosow et al. |

(56) References Cited

U.S. PATENT DOCUMENTS

| | | |
|---|---|---|
| 2003/0141981 A1 | 7/2003 | Bui et al. |
| 2003/0146835 A1 | 8/2003 | Carter |
| 2003/0149598 A1 | 8/2003 | Santoso et al. |
| 2003/0176798 A1 | 9/2003 | Simon |
| 2003/0206116 A1 | 11/2003 | Weiner et al. |
| 2004/0072475 A1 | 4/2004 | Istvan |
| 2004/0073127 A1 | 4/2004 | Istvan et al. |
| 2004/0121767 A1 | 6/2004 | Simpson et al. |
| 2004/0127802 A1 | 7/2004 | Istvan et al. |
| 2004/0147818 A1 | 7/2004 | Levy et al. |
| 2004/0167465 A1 | 8/2004 | Mihai et al. |
| 2004/0176667 A1 | 9/2004 | Mihai et al. |
| 2004/0183681 A1 | 9/2004 | Smith |
| 2004/0183684 A1 | 9/2004 | Callaway |
| 2004/0186358 A1 | 9/2004 | Chernow et al. |
| 2004/0193449 A1 | 9/2004 | Wildman et al. |
| 2004/0259494 A1 | 12/2004 | Mazar |
| 2005/0035862 A1* | 2/2005 | Wildman et al. .......... 340/573.1 |
| 2005/0065817 A1* | 3/2005 | Mihai .................. A61B 5/0002 705/2 |
| 2005/0102167 A1* | 5/2005 | Kapoor ............................. 705/3 |
| 2005/0119866 A1 | 6/2005 | Zaleski |
| 2005/0140508 A1 | 6/2005 | Tessier et al. |
| 2005/0144042 A1 | 6/2005 | Joffe et al. |
| 2005/0148303 A1 | 7/2005 | Dempsey |
| 2005/0177052 A1 | 8/2005 | Istvan et al. |
| 2005/0188083 A1* | 8/2005 | Biondi et al. ................. 709/224 |
| 2005/0197545 A1 | 9/2005 | Hoggle |
| 2005/0206518 A1 | 9/2005 | Welch et al. |
| 2005/0219059 A1 | 10/2005 | Ulrich et al. |
| 2005/0224083 A1* | 10/2005 | Crass .................. G06F 19/326 128/897 |
| 2005/0242946 A1 | 11/2005 | Hubbard, Jr. et al. |
| 2005/0246416 A1 | 11/2005 | Bloomquist |
| 2005/0251002 A1 | 11/2005 | Istvan et al. |
| 2005/0251003 A1 | 11/2005 | Istvan et al. |
| 2005/0251004 A1 | 11/2005 | Istvan et al. |
| 2006/0002340 A1 | 1/2006 | Criss et al. |
| 2006/0030759 A1 | 2/2006 | Weiner et al. |
| 2006/0049936 A1 | 3/2006 | Collins et al. |
| 2006/0077759 A1 | 4/2006 | Holm |
| 2006/0089539 A1 | 4/2006 | Miodownik et al. |
| 2006/0095234 A1 | 5/2006 | Brignone et al. |
| 2006/0106649 A1 | 5/2006 | Eggers et al. |
| 2006/0122867 A1 | 6/2006 | Eggers et al. |
| 2006/0136271 A1 | 6/2006 | Eggers et al. |
| 2006/0143051 A1 | 6/2006 | Eggers et al. |
| 2006/0179571 A1 | 8/2006 | Newkirk |
| 2006/0190302 A1 | 8/2006 | Eggers et al. |
| 2006/0214786 A1 | 9/2006 | Bixler et al. |
| 2006/0220839 A1 | 10/2006 | Fifolt et al. |
| 2006/0238350 A1 | 10/2006 | Tessier |
| 2006/0239195 A1 | 10/2006 | Camins et al. |
| 2006/0242293 A1 | 10/2006 | Russ |
| 2006/0248221 A1 | 11/2006 | Hottel et al. |
| 2006/0253281 A1 | 11/2006 | Letzt et al. |
| 2006/0258926 A1 | 11/2006 | Ali et al. |
| 2006/0267740 A1 | 11/2006 | Bixler et al. |
| 2006/0271207 A1 | 11/2006 | Shaw |
| 2006/0277202 A1 | 12/2006 | Dempsey |
| 2006/0279427 A1* | 12/2006 | Becker .................. A61B 5/0002 340/573.4 |
| 2006/0288095 A1* | 12/2006 | Torok .................. G06F 19/327 709/223 |
| 2007/0010719 A1 | 1/2007 | Huster et al. |
| 2007/0013511 A1 | 1/2007 | Weiner et al. |
| 2007/0060976 A1 | 3/2007 | Denzene et al. |
| 2007/0069887 A1 | 3/2007 | Welch et al. |
| 2007/0112602 A1 | 5/2007 | Bellon et al. |
| 2007/0120689 A1* | 5/2007 | Zerhusen et al. .......... 340/573.1 |
| 2007/0123955 A1 | 5/2007 | Verhoef et al. |
| 2007/0135866 A1 | 6/2007 | Baker et al. |
| 2007/0136102 A1 | 6/2007 | Rodgers |
| 2007/0141869 A1 | 6/2007 | McNeeley et al. |
| 2007/0142716 A1 | 6/2007 | Biondi |
| 2007/0156456 A1 | 7/2007 | McGillin et al. |
| 2007/0156707 A1 | 7/2007 | Fuchs et al. |
| 2007/0180140 A1 | 8/2007 | Welch et al. |
| 2007/0208235 A1 | 9/2007 | Besson et al. |
| 2007/0210917 A1 | 9/2007 | Collins et al. |
| 2007/0214013 A1 | 9/2007 | Silverman |
| 2007/0229249 A1 | 10/2007 | McNeal et al. |
| 2007/0233199 A1 | 10/2007 | Moore et al. |
| 2007/0251835 A1 | 11/2007 | Mehta et al. |
| 2007/0255111 A1 | 11/2007 | Baldus et al. |
| 2007/0255250 A1 | 11/2007 | Moberg et al. |
| 2007/0255348 A1 | 11/2007 | Holtzclaw |
| 2007/0258395 A1 | 11/2007 | Jollota et al. |
| 2007/0279211 A1 | 12/2007 | Fenske et al. |
| 2007/0288263 A1 | 12/2007 | Rodgers |
| 2008/0009694 A1 | 1/2008 | Hopman et al. |
| 2008/0018435 A1 | 1/2008 | Brown |
| 2008/0049555 A1 | 2/2008 | Holm et al. |
| 2008/0114689 A1 | 5/2008 | Psynik et al. |
| 2008/0120784 A1 | 5/2008 | Warner et al. |
| 2008/0122616 A1 | 5/2008 | Warner et al. |
| 2008/0126122 A1 | 5/2008 | Warner et al. |
| 2008/0126132 A1 | 5/2008 | Warner et al. |
| 2008/0147442 A1 | 6/2008 | Warner et al. |
| 2008/0164998 A1 | 7/2008 | Scherpbier et al. |
| 2009/0056027 A1 | 3/2009 | Ball et al. |
| 2009/0063183 A1 | 3/2009 | McNeely et al. |
| 2009/0112630 A1 | 4/2009 | Collins, Jr. et al. |
| 2010/0001838 A1 | 1/2010 | Miodownik et al. |
| 2011/0072583 A1 | 3/2011 | McNeely et al. |
| 2012/0013452 A1 | 1/2012 | McNeely et al. |
| 2012/0072238 A1 | 3/2012 | Collins, Jr. et al. |
| 2012/0330109 A1 | 12/2012 | Tran |

FOREIGN PATENT DOCUMENTS

| | | |
|---|---|---|
| EP | 1 480 388 A2 | 11/2004 |
| EP | 1 734 458 | 12/2006 |
| WO | WO 02/091297 A1 | 11/2002 |
| WO | WO 03/102851 A1 | 12/2003 |
| WO | WO 2004/028344 | 4/2004 |
| WO | WO 2004/036390 A2 | 4/2004 |
| WO | WO 2005/114524 A2 | 12/2005 |
| WO | WO 2007/063157 A2 | 6/2007 |
| WO | WO 2008/004205 | 1/2008 |
| WO | WO 2008/033970 | 3/2008 |
| WO | WO 2008/067176 | 6/2008 |

OTHER PUBLICATIONS

International Preliminary Report on Patentability for PCT/US2008/081049 issued Apr. 27, 2010.
"Cricket v2 User Manual," MIT Computer Science and Artificial Intelligence Lab, Jan. 2005.
"The Cricket Indoor Location System" (9 pages).
Priyantha, et al., "The Cricket Location-Support System," ACM MOBICOM, Aug. 2000.
Chakraborty, Anit, "A Distributed Architecture for Mobile, Location-Dependent Applications," Massachusetts Institute of Technology (1999).
Supplementary European Search Report for EP 08 84 1799, dated Jul. 18, 2013 (13 pages).

* cited by examiner

… (1)

SYSTEM AND METHOD FOR ASSOCIATION OF PATIENT CARE DEVICES TO A PATIENT

This application is a continuation of U.S. application Ser. No. 13/303,624, filed Nov. 23, 2011, now U.S. Pat. No. 8,756,078, which is a continuation of U.S. application Ser. No. 12/256,637, filed Oct. 23, 2008, now U.S. Pat. No. 8,082,160, which claims the benefit, under 35 U.S.C. §119(e), of U.S. Provisional Patent Application No. 61/000,489, filed Oct. 26, 2007, and U.S. Provisional Patent Application No. 61/106,830, filed Oct. 20, 2008, all of which are hereby expressly incorporated by reference herein.

BACKGROUND

The present disclosure relates to systems and methods for collecting, communicating, displaying, and/or analyzing data from multiple patient care devices. More particularly, the present disclosure relates to systems and methods for handling data originating from patient support devices, such as hospital beds, from patient physiological monitors, such as blood pressure monitors or electrocardiographs, and from other patient care devices, such as IV pumps or ventilators, just to name a few.

In the healthcare field, sophisticated equipment from a variety of original equipment manufacturers may be used in connection with the care of each patient. For example, most patients admitted to hospitals are assigned to a hospital bed having a variety of functions which may include, but are not limited to, the ability to weigh the patient, the ability to monitor the position of the patient on a support surface, the ability to determine the position of various portions of the bed frame such as whether the siderails are up or down and the position of various movable deck sections that support the surface, including the angle at which a head section of the bed is elevated. Some hospital beds or mattress systems (sometimes referred to as surfaces) placed on hospital beds are able to perform therapeutic functions such as continuous lateral rotation therapy, pulsation and/or vibration therapies, and/or alternating pressure therapy. Additional surface functions, such as low air loss, maximum inflate, and rapid deflation for CPR may also be included. Accordingly, hospital beds and/or the associated surfaces include sophisticated control and monitoring systems that generate a wide variety of data.

Of course, other sophisticated pieces of equipment are also used in the healthcare field to provide patient care or to monitor the condition of a patient. Such equipment may include, but is not limited to, for example, life support equipment, such as, ventilators; vital signs monitoring equipment such as electrocardiographs (EKG's), electroencephalographs (EEG's), heart rate monitors, blood pressure monitors, blood oxygen saturation monitors; and other patient care devices such as IV pumps, drug infusion pumps, insulin pumps, passive motion devices, and the like. Each of these pieces of equipment also typically has sophisticated control and monitoring systems that generate a wide variety of data.

Some hospitals may have similar pieces of equipment from different manufacturers to which caregivers may come into contract during their day to day activities. The ability of caregivers to master all of the control and monitoring functions of all of the equipment from different manufacturers in the healthcare setting is problematic. However, there are certain key pieces of information or data that common pieces of equipment will each make available to caregivers. Such key pieces of information are oftentimes logged into an Electronic Medical Records (EMR) system. It is not uncommon for caregivers to physically enter the key pieces of information on a handwritten chart and then that caregiver or a different caregiver keys the handwritten data into the EMR system at a later time. To enter the key pieces of information onto the handwritten chart may require the caregiver to know how to navigate through user interface screens of a number of devices marketed by a number of different companies. All of these manual activities by caregivers to find the needed information, enter the data on a chart, and transfer the data at a later time to the EMR system introduce potential sources of error in the data.

Acquiring the key pieces of information automatically from the wide variety of medical equipment for data entry into the EMR system, as well as having the ability to present the wide variety of data to caregivers more uniformly regardless of the type of equipment from which it originates, may be useful in some care settings. Also, a system which is programmable to establish alarm conditions based on logical conditions (e.g., OR conditions and/or AND conditions) applied to data from different patient care devices may have benefit in some instances. Standards of Care are sometimes established for the care of patients and data from different pieces of care equipment may measure aspects of the Standard of Care. The ability to have a common system that monitors the various aspects of the Standard of Care based on data from different devices and that alarm or provides alerts to caregivers when conditions outside the Standard of Care are detected may also be useful in some care settings.

SUMMARY

The present invention may comprise a system or method having one or more of the features recited in the appended claims and/or one or more of the following features which, alone or in any combination, may comprise patentable subject matter:

A system for collecting, communicating, analyzing, and/or displaying data from a plurality of patient care devices of different types may be provided. The system may have a local data collection module comprising a first controller, a receiver coupled to the first controller and operable to receive local wireless signals from a variety of patient care devices, and a transceiver coupled to the first controller and operable to communicate wirelessly with a wireless access point of an Ethernet of a healthcare facility. The local data collection module may also have an Ethernet connector coupled to the first controller and configured for hardwired connection to the Ethernet of the healthcare facility.

The receiver may be operable according to a first wireless communication protocol, such as the 802.15.4 protocol (also known as the Zigbee protocol) or an ultrawide band protocol, and the transceiver may be operable according to a second wireless communication protocol, such as, for example, an 802.11 protocol.

The system may also have a plurality of data communication modules which are also referred to herein as medical device adapters (MDA's). Each MDA may have a second controller and a device connector coupled to the second controller and coupleable to a respective patient care device of the plurality of patient care devices to receive data therefrom. Each MDA may have a transmitter coupled to the respective second controller and operable to transmit local wireless signals to the receiver of the local data collection module according to the first wireless communication protocol. The controller of each of the plurality of MDA's may be programmed to convert the data received from the plurality of patient care devices according to unique device data protocols of the respective patient care devices into data according to a common data protocol and then to signal the associated transmitter to transmit the data so converted to the local data collection module as part of the local wireless signals. In other embodiments, the MDA may simply transmit the data in the data format it is received from the respective care devices. Data conversion then may take place at the local data collection module or even further remotely, such as at a server or other computer device coupled to the hospital Ethernet.

The local data collection module may be coupled to a hospital bed or may even be included as part of the circuitry of the hospital bed. The local data collection module may be coupled to some other device, such as a headwall, arm, column, or other piece of architectural equipment, or be part of a stand alone computer, or even coupled to or integrated with another patient care device. The local data collection module may be coupled to a computer on wheels (COW), such as a mobile cart that caries the local data collection module as well as additional optional computer devices, in some embodiments. Data from the hospital bed also may be communicated to the first controller of the local communication module and transmitted by the transceiver to the wireless access point of the Ethernet of the healthcare facility. Data from the hospital bed may include, but is not limited to, the following: data regarding a function or feature of the hospital bed, data regarding an identification of the hospital bed, data regarding a model number of the hospital bed, data regarding a software revision version of the hospital bed, data regarding a position of a siderail of the hospital bed, data regarding the status of a caster braking system of the hospital bed, data regarding a status of a therapy surface of the hospital bed, data regarding a weighing system of the hospital bed, data regarding a patient position monitoring system of the hospital bed, data regarding a bed exit monitoring system of the hospital bed, and data regarding the angle of elevation of the head section of the hospital bed.

At least one of the MDA's may be configured to also wirelessly communicate with another one of the MDA's to create a local wireless mesh network. The local data collection module may comprise at least one expansion port coupled to the controller and configured to permit at least one additional device to be coupled to the local data collection module via a hardwired connection. The expansion port may comprise, for example, multiple RJ-45 connectors or ports. The controller of the local data collection module may run JAVA applications.

The MDA's may each have a locating device coupled thereto or included as part of the circuitry thereof. The locating devices may comprise an RF receiver and/or an RF transmitter and/or an ultrasonic emitter and/or ultrasonic receiver and/or an IR receiver and/or an IR transmitter. Each of the MDA's may include an Ethernet connector coupled to the respective second controller and configured for hardwired connection to the Ethernet of the healthcare facility or to a port associated with the local data collection module.

The local wireless signals transmitted by the transmitters of the MDA's may comprise packets including a destination address. The destination address may correspond to an address of the local data collection module, for example, or correspond to an address of another one of the MDA's or another computer device of the Ethernet of the healthcare facility, such as a computer device associated with an EMR system.

The types of patient care devices to which the MDA's may be coupled include, but are not limited to, the following types of devices: a vital signs monitor (e.g., an EKG, an EEG, a respiration rate monitor, or a blood pressure monitor), a physiologic monitor (e.g., a blood oxygen saturation monitor, or a temperature sensor), a ventilator, an IV pump, a drug infusion pump. Different MDA's may be coupled to different types of devices.

The system may also have a display communicatively coupled to the local data collection module and operable to display information indicative of the data received by the local data collection modules from some or all of the data communication modules. The display may be coupled to a hospital bed or may be included as part of a tablet or may be included as part of a remote computer or may be included as part of a local computer or may be included as part of a hand-held wireless device such as a personal data assistant (PDA). In some embodiments, the display is integrated with the circuitry of the local data collection module and carried by a common housing that is mounted to a room wall, or a headwall, for example. In some embodiments, the display may show the types of equipment with which the local data collection module is in communication to receive data without showing the data being received. In such embodiments, the local data collection module may simply send the data to another computer device, such an EMR computer, via the hospital Ethernet for automatic logging in the patient's record. The EMR computer may be configured to prompt a user to accept the data prior to logging the data in the patient's record.

The system may further have a third controller that may be operable to analyze the data received by the local data collection module from the MDA's. In analyzing the data, the third controller may determine the existence of an alarm condition based on data from at least two different MDA's. If desired, the controller of the local data collection module may be programmed with similar data analysis capability in lieu of, or in addition to, the third controller having this functionality. The third controller or the controller of the local data collection module may be configured to permit an end user to program the alarm condition based on object oriented programming techniques. Using such object oriented programming techniques, for example, a caregiver may be able to select data thresholds from different types of patient care devices and link them logically (i.e., via greater than, less than, and/or equal to conditions in combination with AND conditions and/or OR conditions) to generate an alarm. To give one general example, the alarm condition may programmed by a caregiver as follows: if a first measured condition (e.g., heart rate) measured by a first patient care device is greater than a first threshold and if a second measured condition (e.g., temperature) measured by a second patient care device is greater than a second threshold, then transmit an alarm message to a designated caregiver.

The third controller or the controller of the local data collection module may be configured to permit an end user to selectively choose data from the plurality of data communication modules for display on at least one dashboard shown on the display. The end users, for example, may be able to create dashboards by selecting a field on a display, such as a touch screen, to indicate which data is to be included in the dashboard or in multiple dashboards. The data field may be located on a virtual rendering of the associated patient care device which appears on the display. The local data collection module may be coupled to a hospital bed and the display may be operable, for example, to display hospital bed data simultaneously with displaying the information indicative of the data received by the local data collection modules from at least some of the MDA's.

Some or all of the MDA's may be operable to perform data filtering so that subsequent packets of information received from the associated patient care device that are identical to previously received packets are not transmitted to the local data collection module. Such an arrangement reduces unnecessary band width usage by transmitting information that has already been transmitted to the local data collection module. If communication is lost between one of the MDA's and the local data collection module, the MDA may be configured to buffer the data received from the respective patient care device for transmission to the local data collection module at a later time when communication is restored.

According to this disclosure, an MDA may be used with a patient care device which has device data pertaining to operation of the device and that has patient data relating to a patient. The patient data may be, for example, patient physiologic data or vital sign data or the like. The patient care device may have a port through which the device data and patient data is obtainable. The MDA may comprise a controller and a connector coupled to the controller and coupleable to the port of the patient care device to establish a wired connection between the patient care device and the data communication module. A cable having appropriate connectors at its end may be provided to couple to an output port of the patient care device and to an input port of the MDA. The MDA may further have a transmitter coupled to the controller and operable to transmit wireless signals which comprise information regarding the device data and the patient data.

A location device that sends or receives at least one signal which is used to determine a location of the MDA, and therefore, the location of the patient care device in a healthcare facility may be coupled to, or included in, the data communication module as alluded to above. The location device may have circuitry that is coupled to the controller. The location device may comprise a location tag coupled to a housing of the data communication module. The location device may comprise an ultrasound emitter, an ultrasound receiver, or an ultrasound transceiver.

The data communication module may also have a module port that permits a hardwired connection to be made to the data communication module. The module port may be a different type of port from the port of the patient care device. For example, the port of the patient care device may comprise an RS-232 port or a Universal Serial Bus (USB) port and the module port may comprise an RJ-45 port. The transmitter of the data communication module may transmit the wireless signals according to the 802.15.4 protocol or according to an ultrawide band protocol. The controller of the data communication module may be configured to perform data filtering so that subsequent device data or patient data received from the patient care device in packets that are identical to previously received packets are not transmitted by the transceiver.

The transmitter of the data communication module may be included as part of a transceiver that is coupled to the controller. The data communication module may further have a receiver coupled to the controller and operable to receive wireless signals. The location device of the data communication module may comprise an ultrasonic receiver. The controller may be programmed so that in response to the receiver receiving an RF location signal from a beacon module contemplated herein, a timer is started, and in response to the ultrasonic receiver receiving an ultrasonic signal from the beacon module the timer is stopped. Accordingly, the controller of the MDA may be able to determine a time difference between receipt of the RF signal and receipt of the ultrasonic signal. In some embodiments, the MDA may be configured to calculate its distance from the beacon based on the time difference. The controller of the MDA may be programmed to transmit the time difference and/or the distance to another device, such as the local data collection module, for example. If the time difference is transmitted by the MDA, the other device may calculate the distance between the MDA and beacon module. The RF location signal and/or the ultrasonic location signal may comprise the at least one signal which is used to determine a location of the data communication module. Based on the time difference data or distance data the other device, such as the local data collection module, may be programmed to automatically associate the data received from various MDA's with a particular hospital bed or patient. In some embodiments, a caregiver may be prompted to confirm the association on the display.

According to this disclosure, a bed listener module (BLM) may be provided for coupling to a hospital bed. The BLM may have circuitry that receives an RF signal and an ultrasound signal from the beacon module, which may be mounted to a room wall or head wall, for example. The BLM may be coupled via a hard wired connection to the local data communication module which is located on the bed or may be coupled to other circuitry located on the bed. If the local data collection module or association computer is not mounted to the bed, such as if the local data collection module is mounted to a room wall or headwall or on a COW, the BLM may have a transmitter to transmit the time difference between receipt of the RF signal and the ultrasound signal to the local data collection module or the association computer. Thus, the BLM may have circuitry substantially similar or even identical to that of an MDA. If the bed data is transmitted via a hardwired connection or via wireless circuitry included as part of the bed to a nurse call system or other computer device of the hospital Ethernet, then the BLM circuitry may still be similar to the MDA circuitry, but may omit the circuitry to transmit according to the 802.15.4 protocol.

Further according to this disclosure, a method of associating a plurality of devices in a room with either a first patient in the room or a second patient in the room is provided. The method may comprise providing time of flight or time of arrival data to an association computer. The association computer may be operable to determine a distance to each device of the plurality of devices from a first reference point associated with the first patient and from a second reference point associated with the second patient based on the time of flight or time of arrival data. The first and second reference points may correspond to locations of first and second beacon modules, respectively. The method may also comprise associating, in the association computer, any devices within a first predetermined distance from the first reference point with the first patient and associating any devices within a second predetermined distance from the second reference point with the second patient. The first and second predetermined distances may be substantially equivalent distances or may be different distances.

As among two like devices in the room, the method may comprise associating the like device that is closest to the first reference point with the first patient and associating a second of the like devices that is closest to the second reference point with the second patient. With regard to ambiguities regarding which patient care device is associated with which patient, the method may also include obtaining data via an Ethernet of a healthcare facility from a remote computer and resolving the ambiguities based on the data obtained from the remote computer. The remote computer may be part of an electronic medical records (EMR) system and/or an admission, discharge, and transfer (ADT) system, for example. The method may comprise prompting the user on the display to resolve any ambiguities regarding which patient care devices are to be associated with which of the two or more patient's in the room.

The time of flight or time of arrival data may be determined as a time difference between receipt of an RF signal and receipt of an ultrasound signal by the MDA's coupled to the patient care devices. It is also contemplated by this disclosure that the locations of the various MDA's, and therefore, the associated patient care devices, with regard to one or more reference points, may be determined using multiple ultrawide signals that are transmitted from different locations in a room and then using triangulation techniques. The reference points may correspond to a patient location, a hospital bed location, a local data collection module location, or a master beacon location. Beacon modules according to this disclosure, therefore, may be configured to transmit ultrawide band signals without transmitting any other signals such as ultrasound or IR signals.

Also according to this disclosure, a method of associating a plurality of devices in a room with either a first patient in the room or a second patient in the room may comprise transmitting wireless location data from each of the plurality of devices to an association computer. The association computer, in turn, may be operable to determine that at least some of the plurality of devices is associated with the first patient and that others of the plurality of devices are associated with the second patient based upon an association rules program that is executed by the association computer. Any ambiguities as to whether at least one device of the plurality of devices is associated with the first patient or the second patient may be resolved by prompting a user on a display to provide information to resolve the ambiguity and receiving the requested information from the user to resolve the ambiguities. The display may comprise part of the association computer. The display may be coupled to a hospital bed and the association computer may be remote from the hospital bed. In other instances, the display may be coupled to a room wall or a headwall coupled to the room wall. The devices may comprise patient care devices having MDA's coupled thereto. The devices may comprise a hospital bed having a BLM.

Transmitting wireless location data from each of the plurality of devices may comprise transmitting wireless location data from location tags coupled to each of the plurality of devices. Furthermore, transmitting wireless location data from each of the plurality of devices may comprise transmitting wireless location data from MDA's attached to each of the plurality of devices. Transmitting wireless location data from each of the plurality of devices to an association computer may comprise transmitting wireless location data from each of the plurality of devices to an association computer via an Ethernet of a healthcare facility.

According to this disclosure, a computer on wheels (COW) is operable as a local data collection module and is wheeled from room-to-room to collect data from MDA's that are coupled to patient care devices in the room. In such an embodiment, a display of the COW may prompt a caregiver to select which devices in wireless communication with the COW within a particular room are to be associated with a particular patient for which data is to be logged automatically. After the COW receives the data from the MDA's of the patient care devices associated with a particular patient, the COW may then transmit the data wirelessly to an EMR computer via the hospital Ethernet. Additionally or alternatively, the COW may simply store the acquired data for the particular patient for transmission to the EMR computer at a later time. By using the COW, a caregiver can go from room-to-room and acquire data for automatic logging into the medical records of the various patients in these rooms. The data acquisition is done automatically by the COW thereby reducing or eliminating the amount of manual data acquisition that needs to be done by the caregiver. In some instances, the caregiver may be required to perform some amount of data entry using a keyboard associated with the COW, for example. However, the more electronic data than can be acquired automatically by the COW from the patient care devices via the MDA's, the less chance there is for human error.

Methods of making and methods of using the local data collection module, the MDA, the beacon module, the BLM, the COW, and systems having these devices are also contemplated and are intended to be within the scope of this disclosure.

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures, in which.

DETAILED DESCRIPTION OF THE DRAWINGS

Figure 1:
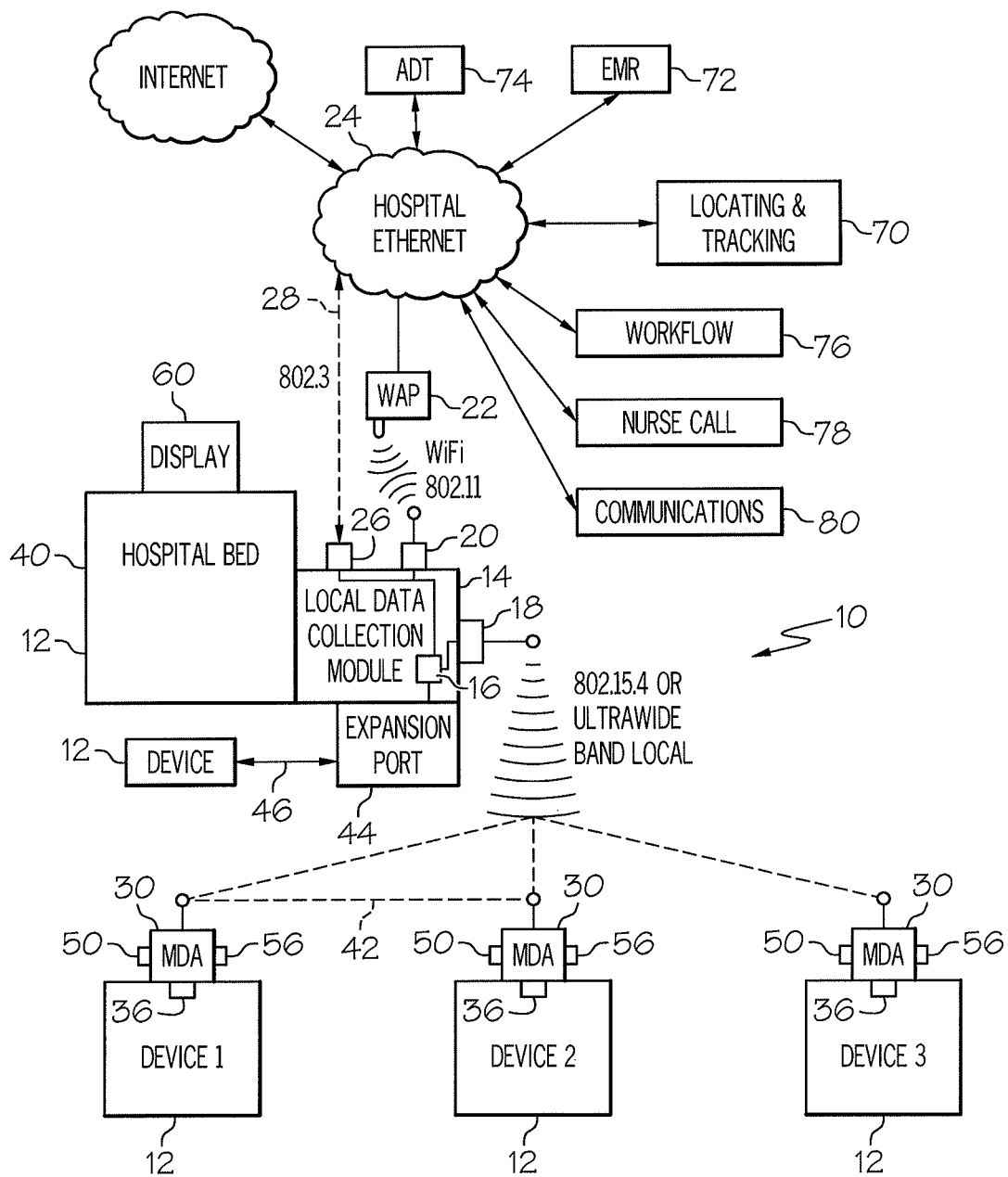
FIG. 1 is a block diagram showing a local data collection module coupled to a hospital bed and receiving wireless signals from medical device adapters (MDA's) that are attached to a number of patient care devices, the hospital bed having a display for displaying at least some of the data received by the local data collection module from the hospital bed and from the other patient care devices, and the local data collection module being coupleable to the hospital Ethernet either via a hardwired connection (indicated by phantom two-way arrow) and/or via a wireless connection to an wireless access point (WAP) of the Hospital Ethernet, and the Hospital Ethernet including or being coupled to an admission/discharge/transfer (ADT) system, the Internet, an electronic medical records (EMR) system, a Locating and Tracking system, a Workflow system, a Nurse Call system, and a Communications system.

A system 10 for collecting, communicating, analyzing, and/or displaying data from a plurality of patient care devices 12 is shown in FIG. 1. System 10 has a local data collection module 14 such as a Java Application Control Engine (JACE) available from Tridium, Inc. of Richmond, Va. In a prototype of system 10, a JACE-201 was used as module 14 and included Tridium's NIAGARA™ software. In other embodiments, however, module 14 may comprise other types of computer devices having wireless communication capability. For example, an embodiment of system 10 in which a JACE-700, which is sometimes referred to as a JACE7, is used as module 14 is contemplated by this disclosure. Module 14 includes a controller 16 (e.g., a microprocessor or microcontroller and related circuitry, or the like), a receiver 18 coupled to the first controller and operable to receive local wireless signals. Module 14 also has a transceiver 20 coupled to controller 16 and operable to communicate wirelessly with a wireless access point 22 of an Ethernet 24 of a healthcare facility, such as by a WiFi protocol including, for example, an 802.11 protocol (e.g., $802.11_g$, etc.). The local data collection module 14 may also have an Ethernet connector 26, such as an 802.3 port or RJ-45 connector, coupled to controller 16 and configured for hardwired connection to the Ethernet 24 of the healthcare facility as indicated by dashed line 28 in FIG. 1. Thus, two-way data communication between module 14 and Ethernet 24 may be via a wireless or wired connection or data link.

The receiver 18 of module 14 is operable according to a short range wireless communication protocol, such as the 802.15.4 protocol (also known as the Zigbee protocol) or an ultrawide band protocol (e.g., any of the ultrawide band communications protocols that currently exist or that are in development currently or that may be developed in the future). In other embodiments, receiver 18 is included as part of a transceiver that also is able to transmit data from module 14 to devices 12. It is also within the scope of this disclosure for module 14 to have one or more separate receivers and transmitter for communication with devices 12 and other devices for that matter.

System 10 also has a plurality of data communication modules 30 as shown in FIG. 1. Data communication modules 30 are sometimes referred to herein as medical device adapters (MDA's) and these terms are intended to be interchangeable. Each MDA 30 has a controller 32 (e.g., a microprocessor or microcontroller and related circuitry) and a device connector 34 (see FIG. 2) that is coupled to controller 32 and that is coupleable to a connector 36 (see FIG. 1) of the respective patient care device 12. The connector 36 of some patient care devices 12 is an RS-232 port and, in other patient care devices, is a Universal Serial Bus (USB) port.

In some embodiments, connector 34 of module 30 is configured appropriately for coupling to the connector 36 of an associated device. Thus, it is within the scope of this disclosure for the connectors 34 of module 30 to be appropriately fashioned for the connector 36 of the device 12 to which the particular module 30 is to be coupled regardless of what type of connector 36 a particular device 12 may have. In some embodiments contemplated herein, cables having appropriately configured couplers at their ends are used to connect to connectors or ports 34 of modules 30 and to connectors or ports 36 of devices 12. It will be appreciated such cables may be custom-designed in some instances in which devices 12 have output ports that are unique or of a type that are rarely used.

Figure 2:
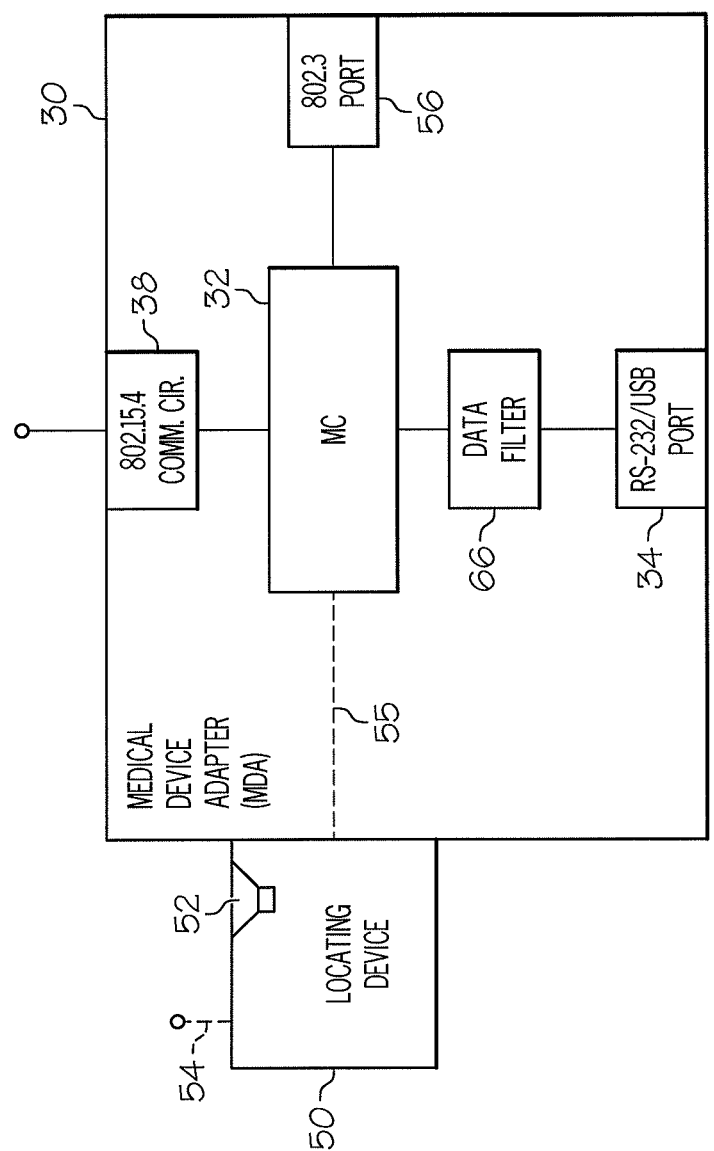
FIG. 2 is a block diagram showing the MDA having a controller, a wireless communication circuit coupled to the controller, a hardwired connection port coupled to the controller, a device connection port coupled to the controller, and a locating device coupled to the controller (in phantom)

Each MDA 30 has communication circuitry and/or a transmitter 38, as shown in FIG. 2, coupled to controller 32 and operable to transmit local wireless signals to receiver 18 of the local data collection module 14 according to the associated wireless communication protocol, which in some embodiments of system is the 802.15.4 protocol but may be some other ultrawide band protocol or other protocol in other embodiments. The wireless signal transmitted by transmitter 38 of module 30 includes data received from the associated device 12 by module 30 via connector 34.

In some embodiments, the data received from device 12 is transmitted according to the data format or protocol in which the data was received from device 12. However, it is contemplated by this disclosure that controller 32 of module 30 may be programmed to convert the data that is received from the associated device 12 according to a device data protocol, which may be unique to the particular device, into data according to a common protocol or format and then to signal transmitter 38 to transmit the converted data to the local data collection module 18. In other embodiments, the protocol or format conversion of data from devices 12 is performed by controller 16 of module 14. Systems in which data is converted by module 30 for some devices 12 and is converted by module 14 for other devices 12 are also contemplated. Also contemplated by this disclosure are systems in which conversion of data from one format to another is performed at some other computer device that is coupled to hospital Ethernet 24 and located remotely from the room in which modules 14, 30 are located.

The local data collection module 14 is coupled to a hospital bed 40 in the illustrative example. In other embodiments, module 14 may be included as part of the circuitry or electrical system of the hospital bed 40 rather than being a separate, discrete module that attaches to it. Data from the hospital bed 40 also is communicated to controller 16 of the local communication module 30 and, in turn, transmitted by the transceiver 20 to the wireless access point 22 of the Ethernet 24 of the healthcare facility. The controller 16 of the local data collection module 14 may run JAVA applications. In the some contemplated embodiments, hospital bed 40 is a Hill-Rom TotalCare® bed, for example.

Figure 9:
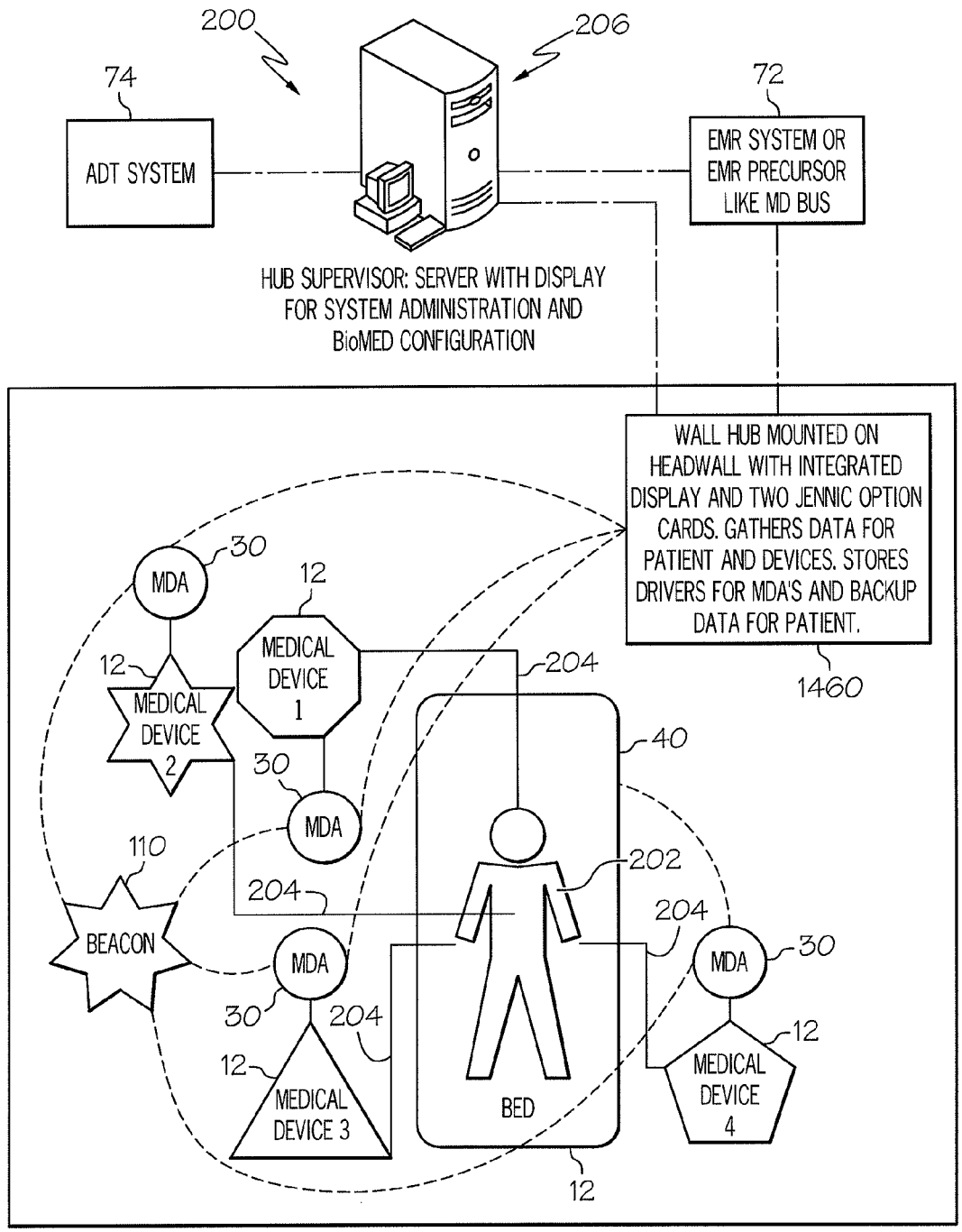
FIG. 9 is a diagrammatic view, similar to FIG. 1, of an alternative embodiment of a system according to this disclosure, showing the system including a local data collection module (referred to in FIG. 9 as a "wall hub") mounted to a headwall of the room and receiving data from MDA's coupled to associated medical devices which, in turn, are coupled to a patient support on a bed, the system also having a beacon module in communication with the MDA's to determine location information about the MDA's in the room, and the local data collection module being coupled to an EMR system and to a hub supervisor which is, in turn, coupled to an ADT system.

It is within the scope of this disclosure for module 30 to be coupled to some other device, such as a room wall, a headwall (see headwalls 101 and 102 of FIG. 3) that is coupled to a room wall, an arm, a column, or other piece of architectural equipment (not shown), or to be part of a stand alone computer, or even coupled to or integrated with another patient care device. In the illustrative embodiment shown in FIG. 9, for example, the local data collection module and display are integrated together and are indicated diagrammatically to be coupled to a headwall of a room. In FIG. 9, module 1460 is referred to as a "wall hub." When module 14 is coupled to hospital bed 40, it may be referred to as a "bed hub" and the bed data is communicated to the bed hub via wired connections. When module 14 is not mounted on bed 40, or included as part of the circuitry of bed 40, then bed 40 communicates its bed data wirelessly to the module 14 in much the same way that the MDA's 30 communicate data from devices 12 to module 14.

Data from the hospital bed may include, but is not limited to, the following: data regarding a function or feature of the hospital bed, data regarding an identification of the hospital bed, data regarding a model number of the hospital bed, data regarding a software revision version of the hospital bed, data regarding a position of a siderail of the hospital bed, data regarding the status of a caster braking system of the hospital bed, data regarding a status of a therapy surface of the hospital bed, data regarding a weighing system of the hospital bed, data regarding a patient position monitoring system of the hospital bed, data regarding a bed exit monitoring system of the hospital bed, and data regarding the angular positions of deck sections of the bed, including the angle at which the head section of the bed is elevated. U.S. Pat. App. Pub. No. 2007/0210917 A1 gives additional examples of bed data and is hereby incorporated by reference herein in its entirety for all that it teaches.

In some instances, the MDA's 30 receive power from the devices 12 to which they connect either via connectors 36 of devices 12 or via other power connectors (not shown). In other instances, MDA's 30 receive power from batteries carried by the MDA's. The 802.15.4 protocol is suitable for offering a fundamental lower network layer to provide a low-cost wireless personal area network (WPAN) that has communications between devices which are short range, low-speed (i.e., low data rate), and low power. Thus, use of the 802.15.4 communication protocol between MDA's 30 and local data collection modules 14 enhances battery life in those instances when power is not otherwise available to a particular MDA from another source.

As indicated by dashed line 42 in FIG. 1, at least one of the data communication modules 30 may be configured to also wirelessly communicate with another one of the data communication modules 30 to create a local wireless mesh network. Thus, if one of modules 30 is within range to successfully communicate with module 14 according to the short range RF transmission being used, and another of modules 14 is within range of the first module 30 but not module 14, then the module 30 within range of module 14 may communicate to module its associated data and the data associated with the other module. Furthermore, multiple modules 30 may form a wireless mesh network and the modules 30 that are outside the range for communicating with module 14 directly may route all their associated data to module 14 via one or more modules 14 that are within the range for communicating with module 14.

As shown in FIG. 1, the local data collection module 14 may comprise at least one expansion port 44 coupled to controller 16 and configured to permit at least one additional device to be coupled to the local data collection module via a hardwired connection 46. It is contemplated that multiple expansion ports 44 may be included in system 10. The expansion ports 44 may comprise, for example, multiple RJ-45 connectors or ports. Other types of connectors or ports, such as RS-232 ports, RS-485 ports, USB ports, etc. are contemplated as being included in an expansion port device. In an illustrative example, shown in FIG. 8, a bank 111 of RJ-45 ports 112 is used as an expansion port 44 to permit hardwired connections with devices 12. In the FIG. 8 example, a cable 114 has an RJ-45 connector 116 at its end inserted into one of the RJ-45 connectors 112 of expansion port 44.

Figure 8:
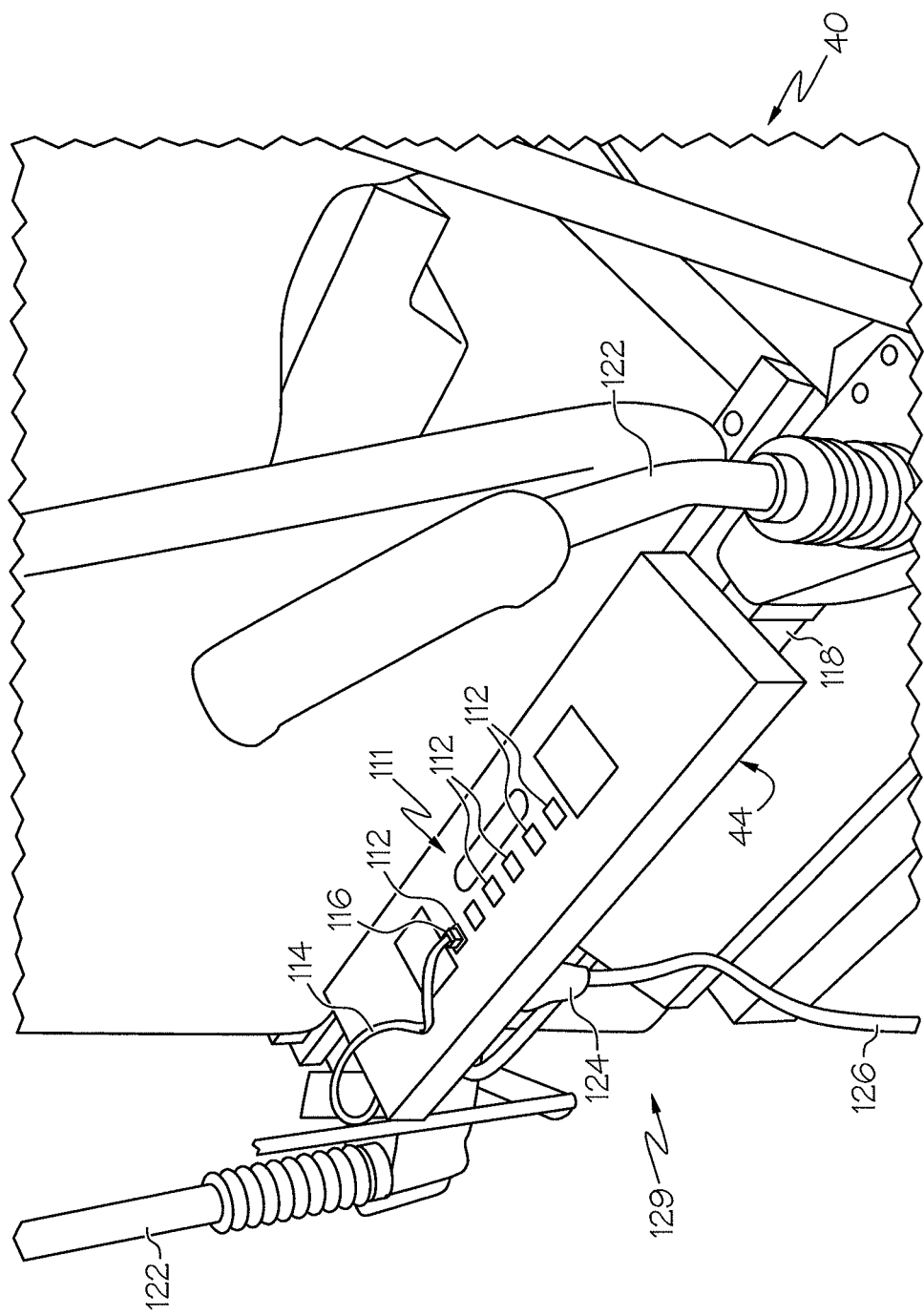
FIG. 8 is a partial isometric view of a head end of a hospital bed showing an expansion port mounted to a frame of the hospital bed between push handles of the bed, the expansion port including a bank of ports to which patient care equipment is coupleable via a wired connection to transfer data to the local data collection module without the need for wireless transmission of the data.

The expansion port 44 of FIG. 8 is physically attached to a frame member 118 at a head end 120 of bed 12 between a pair of push handles 122 of bed 12. As also suggested in FIG. 8, one or more power outlets may be provided on the underside of expansion port 44 for receipt of a plug 124 of a power cord 126. Power cord 126 and/or cable 114 extend from one of the patient care devices 12 that is providing care to the patient on bed 40. Because the head end 120 of bed 40 is typically positioned near a room wall or headwall of a hospital room and because a large number of patient care devices are typically located near the head end of the bed supporting the patient during use, providing expansion port 44 at the head end of the bed 40 allows for the various cables, such as cable 114, to be routed to expansion port 112 in a manner that minimizes interference with the caregivers access to the patient at the bedside and that minimizes interference with the operation of bed components, such as the siderails. In other embodiments, expansion port 44 couples to a wall or headwall of the room and devices 12, or cables from MDA's that are coupled to devices 12, are coupled to connectors 112 of expansion port 44.

The MDA's 30 may each have a locating device 50 coupled thereto or included as part thereof as shown diagrammatically in FIG. 2. The locating device 50 may comprise a receiver 52, such as an RF, IR, or ultrasound receiver, and/or a transmitter 54, such as an RF, IR, or ultrasonic transmitter. In some embodiments, the circuitry of the locating device 50 may be coupled to controller 32 as indicated by dashed line 55 in FIG. 2, in which case transmitter 54 may be omitted and transmitter 38 may be used for the locating functionality in addition to its other uses. Each of the data communication modules 30 may include an Ethernet connector 56 coupled to the controller and configured for hardwired connection to the Ethernet 24 of the healthcare facility or to some other port such as a port associated with another module 30 or to expansion port 44. Port 56 may be, for example, an 802.3 port such as an RJ-45 connector. The locating device 50 is used to locate the whereabouts of the associated module 30, and therefore, the associated device 12 in a healthcare facility. Such location data may be used to automatically associate a particular device 12 with a particular patient or with some other device, such as bed 40.

The local wireless signals transmitted by the transmitters 38 of the data communication modules 30 may comprise packets including a destination address. The destination address may correspond to an address of the local data collection module 14, for example, or correspond to an address of another one of the data communication modules 30 that form part of a wireless mesh network, or may even correspond to some other device that is coupled to or included in Ethernet 24.

The types of patient care devices 12 to which the data communication modules 30 may be coupled include, but are not limited to, the following types of devices: a vital signs monitor (e.g., an EKG, an EEG, a respiration rate monitor, and/or a blood pressure monitor), a physiologic monitor (e.g., a blood oxygen saturation monitor, and/or a temperature sensor), a ventilator, an IV pump, and/or a drug infusion pump. This disclosure contemplates that modules 30 may be coupled to any and all types of patient care devices that have output ports for providing available data to external devices. In some instances, in order to fully decipher the data (e.g., the formatting of the data) being output by some patient care devices 12, cooperation will be needed by the manufacturer of such devices as such manufacturers may have developed their own unique and/or proprietary data formatting protocols. However, it will be appreciated that system 10 permits data collection by module 14 of data from a wide variety of equipment made by different manufacturers. In a prototype system, for example, module 14 received data transmissions from a Puritan Bennett 840 ventilator and a Dinamap Pro 300 which is a physiological monitor for monitoring blood pressure and pulse oximetry.

Illustrative system 10 also has a display 60 communicatively coupled to the local data collection module 14 and operable to display information indicative of the data received by the local data collection module 14 from some or all of the data communication modules 30. Display 60 may be coupled to hospital bed 14, as shown in FIG. 1, or may be included as part of a tablet (not shown, but included in the prototype system) or may be included as part of a remote computer (not shown) or may be included as part of a local computer (not shown) or may be included as part of a hand-held wireless device such as a personal data assistant (PDA).

System 10 may further have a third controller, such as a computer device, that may be operable to analyze the data received by the local data collection module 14 from the data communication modules 30. In analyzing the data, the third controller may determine the existence of an alarm condition based on data from at least two different data communication modules. The third controller may be part of a computer that is coupled to Ethernet 24. If desired, the controller 16 of the local data collection module 14 may be programmed with similar data analysis capability in lieu of, or in addition to, the third controller having this functionality. The third controller or the controller of the local data collection module 14 may be configured to permit an end user to program the alarm condition based on object oriented programming techniques. See U.S. Pat. Nos. 7,225,426 and 6,832,120 which are believed to relate to object oriented programming of Tridium's JACE devices. The alarm conditions may be established in accordance with a Standard of Care.

According to this disclosure, the third controller or the controller 16 of the local data collection module 14 may be configured to permit an end user to selectively choose data from the plurality of data communication modules 30 for display on at least one dashboard shown on the display 60. The end users, for example, may be able to create dashboards by selecting a field on a display 60, such as a touch screen, to indicate which data is to be included in the dashboard. The data field may be located on a virtual rendering of the associated patient care device 12 which appears on the display 60. The data acquired by MDA's and transmitted to local data collection module 14 may be displayed in graphical or tabular form on display 60.

Figure 4:
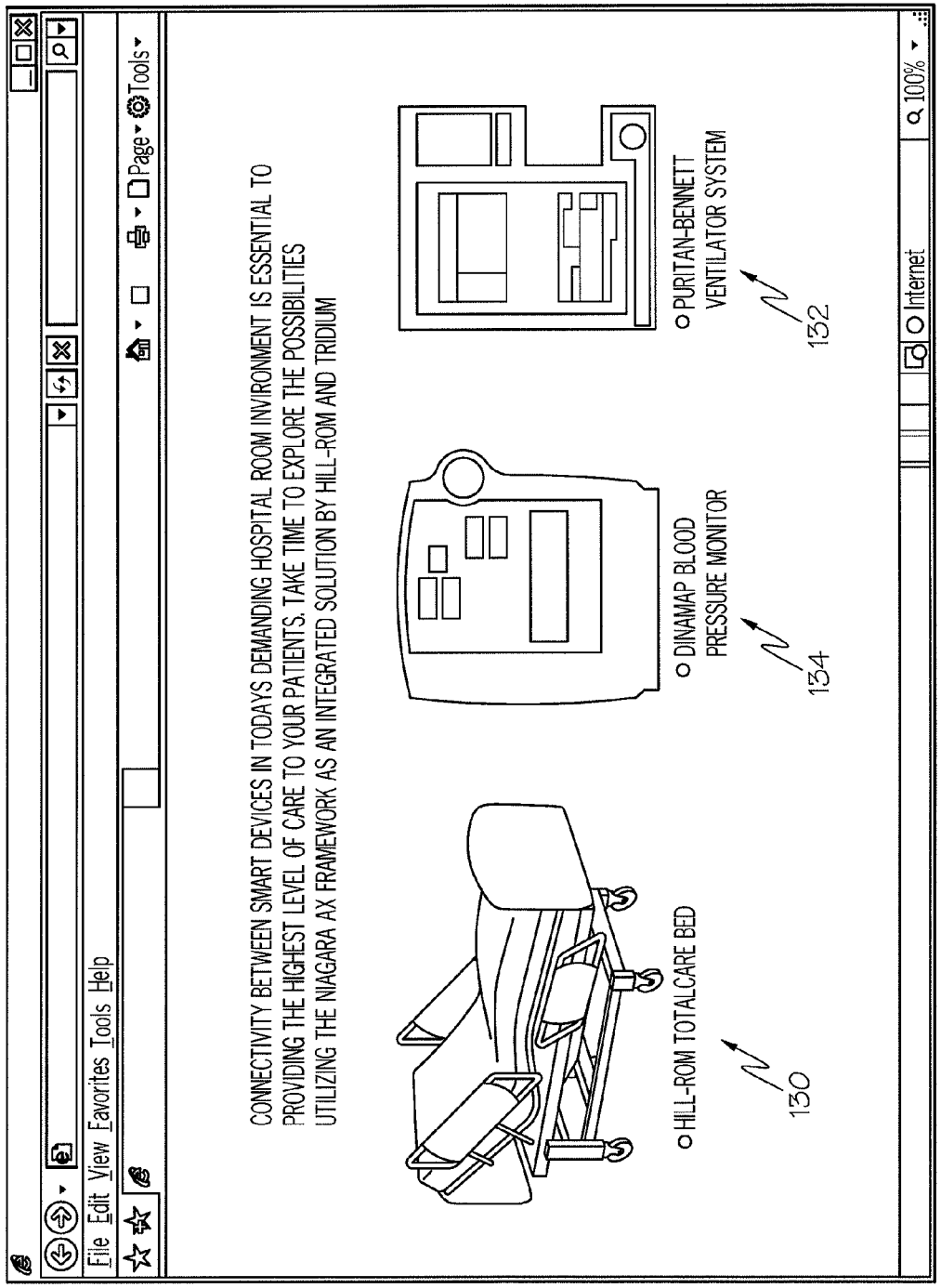
FIG. 4 is a screen shot of a home screen on which a rendering of a hospital bed, a blood pressure monitor, and a ventilator are displayed.

In one embodiment of system 10, virtual renderings 130, 132, 134 of the Hill-Rom TotalCare® bed, the Puritan Bennett 840 ventilator, and the Dinamap Pro 300 monitor, respectively, were displayed simultaneously on the display 60 on a home screen 129 as shown in FIG. 4. In this example of system 10, the virtual renderings 132, 134 of the monitor and ventilator mimic the look and feel of the user interface (i.e., input and output portions) of these devices including showing at least some of the digital readings appearing on the actual devices and updating them from time to time as the data from the MDA's 30 is received by module 14. Also in this example, the virtual rendering 130 of the hospital bed is an image of the overall bed that mimics the position of various positions of the bed (e.g., siderails up or down, head section raised or lowered, upper frame raised or lowered, and so on). It will be appreciated that, the display 60 may be operable, for example, to display hospital bed data simultaneously with displaying the information indicative of the data received by the local data collection modules from at least some of the data communication modules. Such data may appear on a different portion of the display 60 than where the virtual rendering appears.

Figure 5:
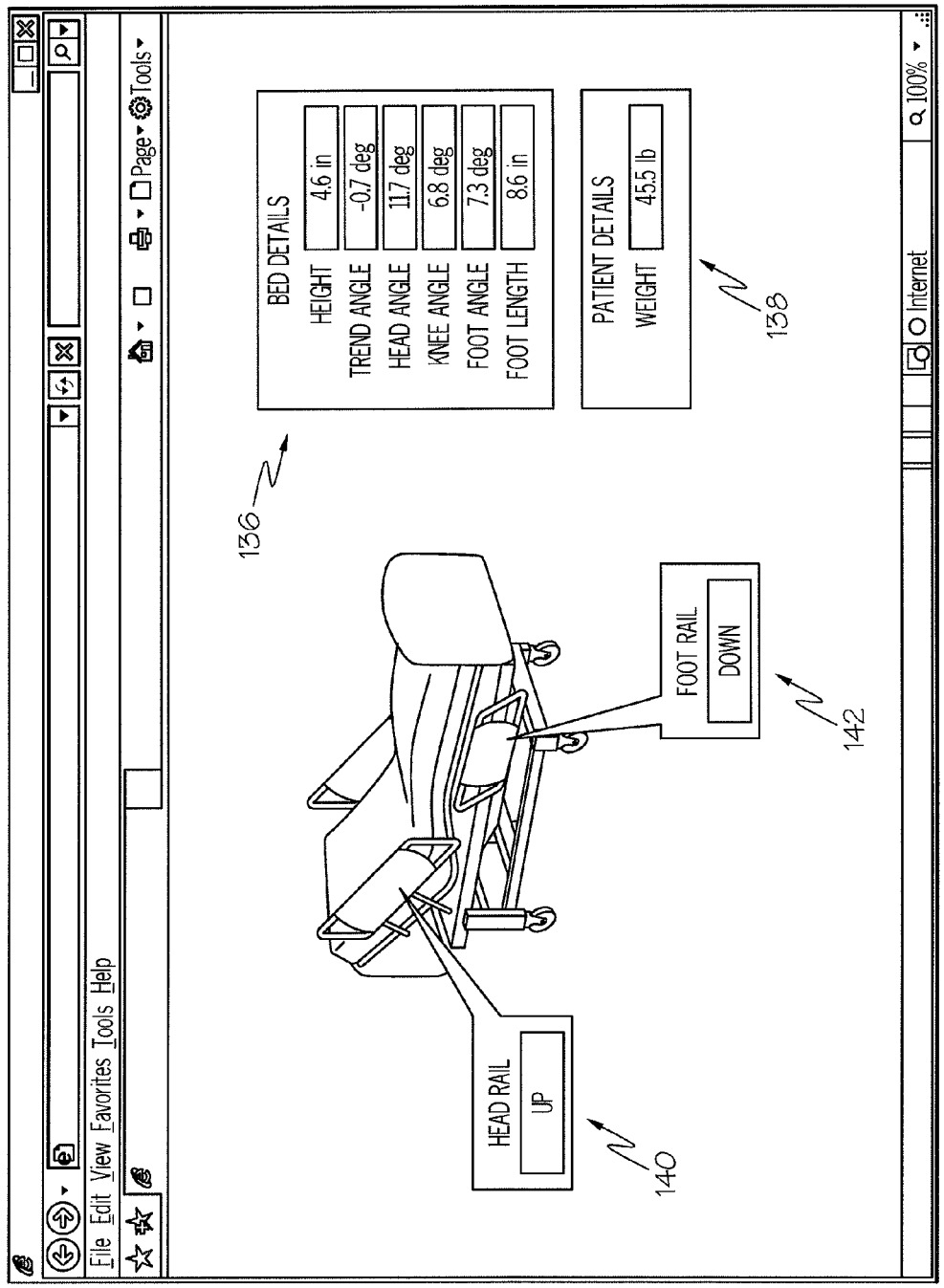
FIG. 5 is a screen shot of a bed screen that is displayed in response to selection of the bed rendering on the home screen, the bed screen providing a variety of information regarding the angular, height and length positions of various portions of the bed as well as the weight sensed by a weigh scale system of the bed of a patient supported on the bed.

It is contemplated by this disclosure that display 60 is a touch screen display. A caregiver may touch one of renderings 130, 132, 134 to view additional information about the associated patient care device. For example, if the caregiver touches rendering 130 of hospital bed on screen 129 shown in FIG. 4, the controller 16 responds by displaying a bed screen 135 which includes a table 136 having information about various positions of bed components as shown in FIG. 5. In the illustrative example, table 136 includes data relating to bed height (i.e., the amount that an upper frame of the hospital bed is elevated relative to a lower frame or to the floor); Trendelenburg angle (i.e., the angle that the upper frame of the bed is tilted relative to horizontal or relative to the base frame); the angular positions of head, knee, and foot sections of an articulated deck of the hospital bed; and the length that the foot section is extended. Also in the illustrative example, a box 138 is provided on screen 135 to display the weight of the patient as sensed by a weigh scale system of the hospital bed. First and second boxes 140, 142 are also provided on screen 135 to indicate the positions of a head rail and foot rail (e.g., the siderails). In the illustrative example, the head rail is up and the foot rail is down.

Figure 6:
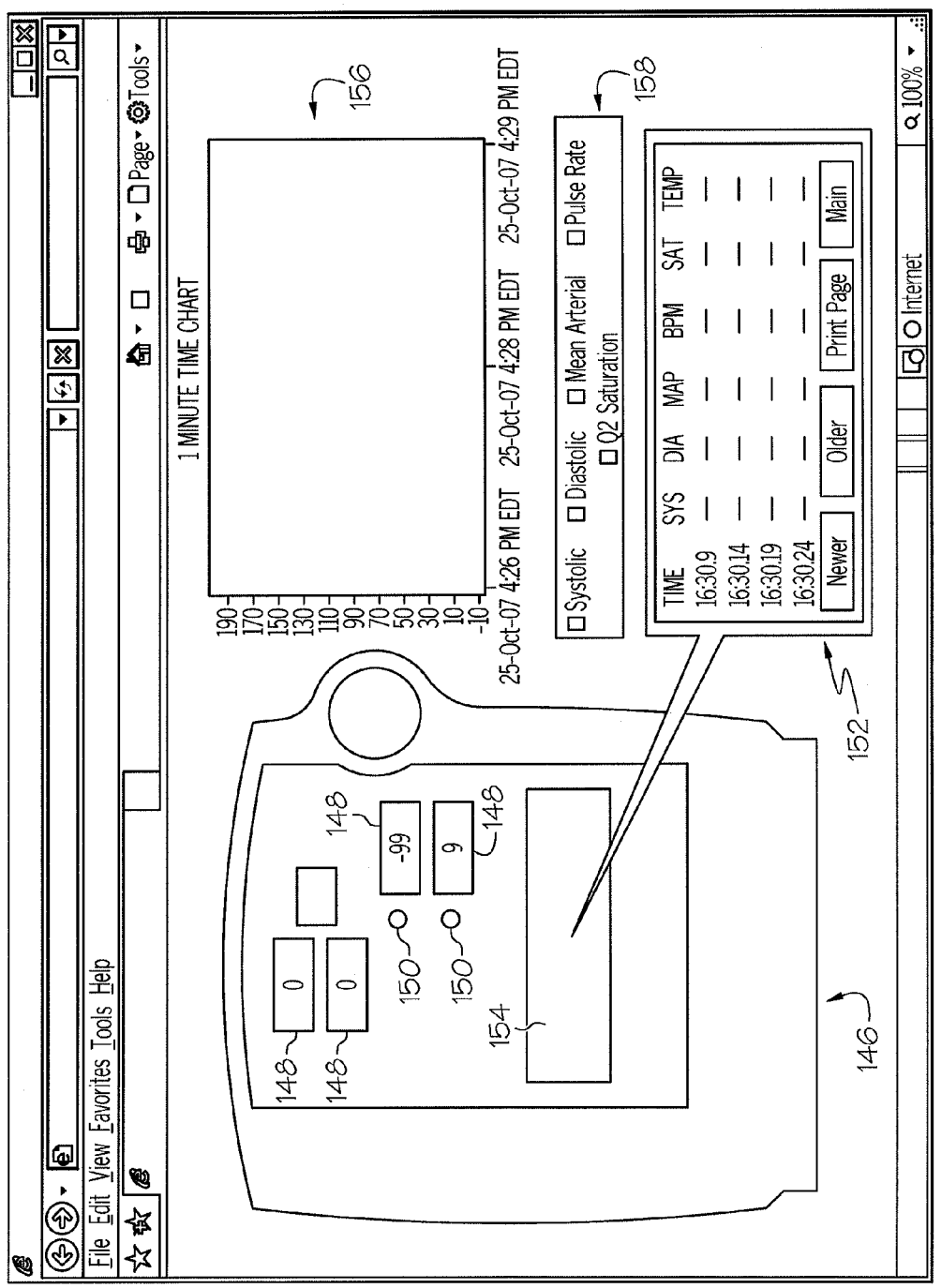
FIG. 6 is a screen shot of a blood pressure monitor screen that is displayed in response to selection of the blood pressure monitor rendering on the home screen, the blood pressure monitor screen showing blood pressure information on the rendering in the same location that it appears on the actual physical device, an enlarged table of information on the lower right hand portion of the screen, and a graph of blood pressure on the upper right hand portion of the screen.

If a caregiver touches monitor rendering 134 on screen 129 shown in FIG. 4, the controller 16 responds by displaying a monitor screen 144 on display 60 as shown, for example, in FIG. 6. Screen 144 includes an enlarged rendering 146 having a number of data boxes 148 in which the corresponding data, as it appears on the actual monitor, is shown. Renderings 150 of LED status indicators of the actual monitor are also shown on screen 144 in the appropriate location of enlarged rendering 146. In the illustrative example, an enlarged table 152 is provided to present the associated data to the caregiver in a larger size than it would be presented if simply reproduced in an area 154 of rendering 146. A one minute time chart or graph 156 is also shown on screen 144. If the caregiver operates the actual monitor to generate a one minute time chart, then a corresponding chart is generated on graph 156 of screen 144. A color key 158 is provided beneath graph 156 on screen 144 so that the caregiver can see which physiological parameter corresponds to the associated trace on graph 156 when it appears. Screen 144 of FIG. 6 is an example in which data is presented to caregivers in basically the identical format and arrangement that the caregivers are used to seeing on the actual associated device 12.

Figure 7:
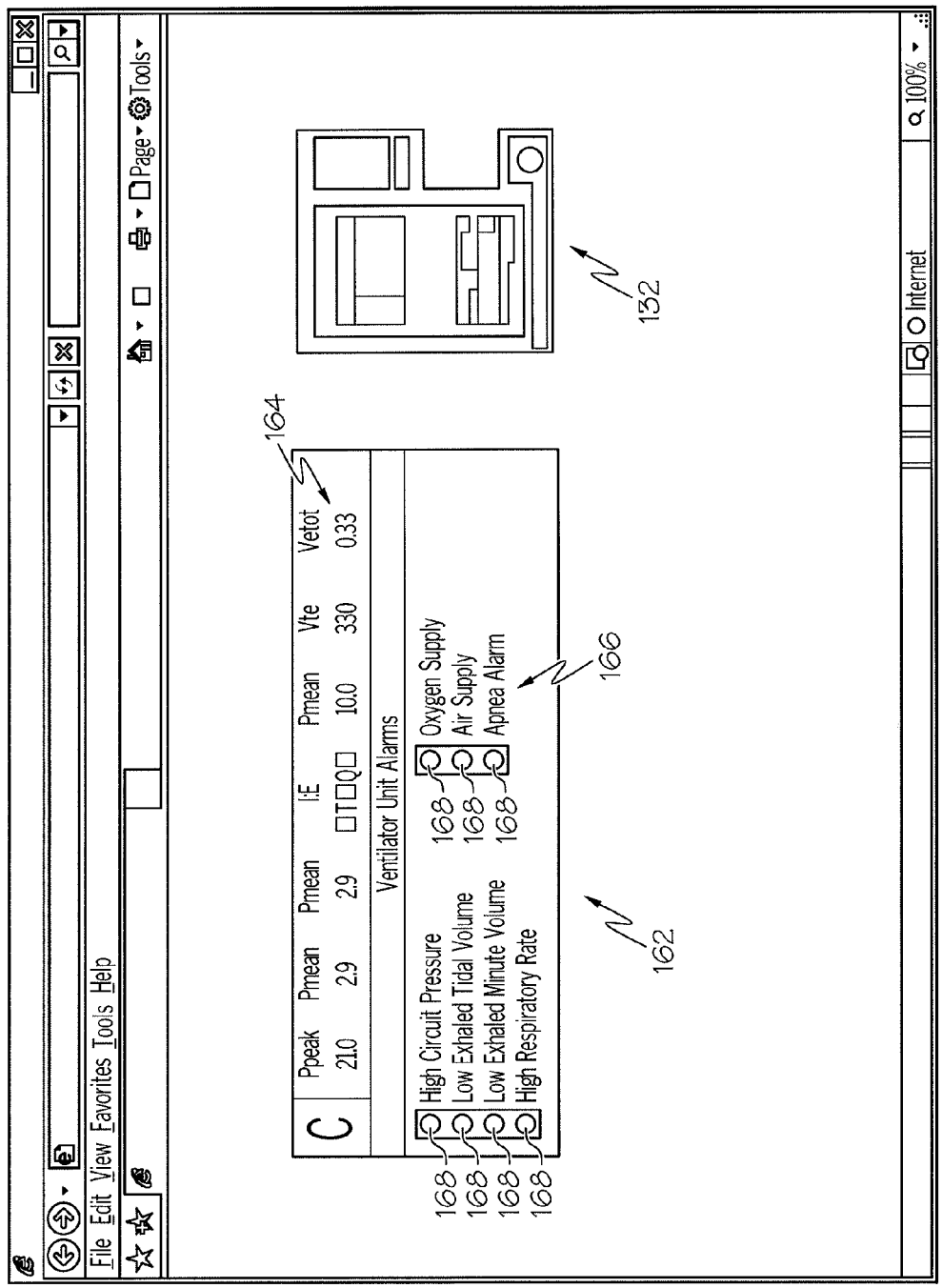
FIG. 7 is a screen shot of a ventilator screen that is displayed in response to selection of the ventilator rendering on the home screen, the ventilator screen showing a rendering of the ventilator on the right hand portion of the ventilator screen and an enlarged window to the left of the ventilator rendering, the enlarged window being displaying key pieces of information from the ventilator.

If a caregiver touches ventilator rendering 132 on screen 129 shown in FIG. 4, the controller 16 responds by displaying a ventilator screen 160 on display 60 as shown, for example, in FIG. 7. Rendering 132 of screen 129 continues to be shown on screen 160 in its same size in the illustrative example. However, a table 162 is provided on screen 160. Key pieces of data are shown in an upper area 164 of table 162. The key pieces of data in area 164 are presented to the user in a different format and/or arrangement than the same data is presented to the user on the actual ventilator. Thus, it is within the scope of this disclosure for users to program controller 16 to display data from devices 12 in a manner that is more to their liking than the same data may be displayed on an actual device. Also, the key pieces of information received from the same type of device, but from different manufacturers, may be shown on display 60 with the same look and feel. Thus, by having controller 16 of module 14 appropriately programmed caregivers can receive data in a more consistent manner even though the data may be provided to module 14 from a wide variety of devices of the same type (e.g., different ventilators from different manufacturers).

Table 162 also has a lower area 166 with a list of alarm conditions that may occur on the associated device 12, in this case, a ventilator. Renderings 168 of status LED indicators are provided next to each of the alarm conditions listed in area 166 of table 162. The alarm list of table 162 may mimic a similar table of an actual device 12 in some instances, and may be custom programmed in other instances to provide a more user friendly presentation of the alarm list to caregivers. Using such custom programming allows for alarm conditions to be presented to caregivers in a more consistent format from device to device of the same type. The renderings 168 of status LED indicators may be green when no alarm condition is occurring, yellow when an alarm condition may soon occur and red when an alarm condition is occurring. It should be noted that the actual device may not indicate an alarm condition in the manner in which it is indicated on display 60 of system 10. Thus, users are able to program system 10 so as to present alarm condition data to caregivers in a format and/or arrangement that is more to their liking than the same information is presented on an actual device 12.

Referring once again to FIG. 2, the illustrative MDA's 30 have a data filter 66 operable to filter data so that subsequent packets of information received from the associated patient care device 12 that are identical to previously received packets are not transmitted to the local data collection module 14. Such an arrangement reduces unnecessary bandwidth usage by transmitting information that has already been transmitted to the local data collection module 14. The data filter 66 may be implemented via software and/or hardware. For example, the packets that have been transmitted by transmitter 38 may be copied to memory of module 30 and then controller 38 may run a software routine to compare subsequent packets to the packets that are stored in memory. In some embodiments, the data filter 66 is omitted and the MDA 30 lacking filter 66 simply transmits data as it is received from the associated device 12. If communication is lost between one of the MDA's 30 and the local data collection module 14, the MDA 30 may buffer the data received from the respective patient care device in memory for transmission to the local data collection module 14 at a later time when communication is restored.

As mentioned above, MDA's 30 have location device 50 that sends or receives at least one signal which is used to determine a location of the MDA 30, and therefore, the location of the associated patient care device 12 in a healthcare facility. The locating device 50 may be coupled to, or included in, the MDA 30. Thus, the locating device 50 may be a locating tag that couples to a housing of module 30. The locating device 50 may have circuitry that is coupled to the controller 32 as also previously mentioned.

The transmitter 38 of the MDA 30 is included as part of a transceiver that is coupled to the controller 30 in some embodiments contemplated herein. Thus, MDA 30 may further have a receiver coupled to the controller 32 and operable to receive wireless signals. In some embodiments, the location device 50 of the MDA has an ultrasonic receiver 52 as previously mentioned. The controller 32 is programmed to determine a time difference between the time at which the receiver of circuitry 38 receives an RF location signal and the time at which the ultrasonic receiver 52 receives an ultrasonic signal. The time difference may, for example, be calculated using a timer that starts when the RF location signal is received and that stops when the ultrasound signal is received or the time difference may be determined by logging in memory the times at which the RF location signal and the ultrasound signal are received and then subtracting the times. Other ways of determining the time difference, such as by counting the number of clock pulses of an oscillator between receipt of the RF location signal and the ultrasound signal, are within the scope of this disclosure. The time difference may be referred to as a time of flight (TOF) in some instances, and the time at which the RF location signal and ultrasound signal are received may be of may be referred to as time of arrival (TOA) in some instances.

Regardless of the technique used, once the controller 32 determines a time difference between receipt of the RF location signal and receipt of the ultrasonic signal, the controller 32 transmits, as one of its wireless signals, the time difference to another device such as module 14 or to a device associated with a locating and tracking system that is coupled to Ethernet 24. Alternatively or additionally, controller 32 may be configured to calculate a distance based on the time difference. The distance calculated is how far away the MDA 30 is from a beacon module which houses the source of transmission of the RF location signal and the ultrasound signal. The beacon module is discussed in further detail below. In those embodiments in which MDA's 30 transmit the time difference, then the receiving device, such as module 14 or another computer device calculates the distance based on the time difference.

Figure 3:
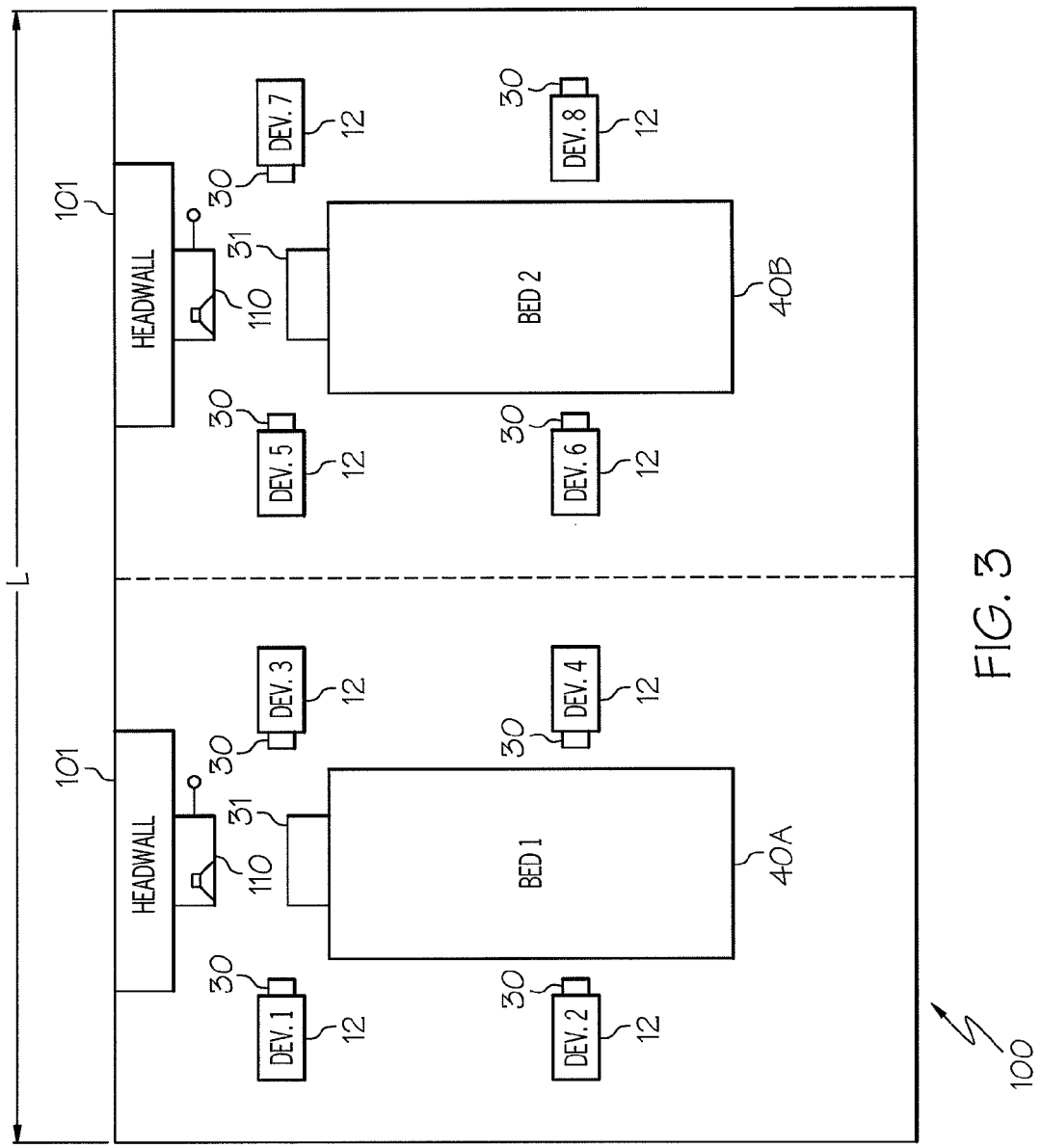
FIG. 3 is a block diagram showing two hospital beds in a hospital room and showing a number of patient care devices, some of which are used for care of a patient associated with one of the hospital bed and others of which are used for care of a patient associated with the other hospital bed.

As shown diagrammatically in FIG. 3, hospital rooms oftentimes have two patient beds 40 (designated as 40A and 40B in FIG. 3) in the same room. Thus, wireless transmissions from modules 30 of devices 12 associated with a first patient on bed 40A may get received by module 14 of bed 40B and wireless transmissions from modules 30 of devices 12 associated with a second patient on bed 40B may get received by module 14 of bed 40A. Accordingly, to reduce the need for caregivers to perform a lot of computer data entry to associate devices 12 with patients, this disclosure contemplates various device-to-patient (or device-to-bed) association methods.

According to this disclosure, a method of associating a plurality of devices 12 in a room 100 with either a first patient in the room (e.g., a patient on bed 40A) or a second patient in the room (e.g., a patient on bed 40B) is provided. As described above locating devices 50 in combination with controller 32 of MDA's 30 are able to determine the time difference between receipt of an RF locating signal and receipt of an ultrasound locating signal. Because the RF signals travel approximately at the speed of light, they are received by MDA's 30 substantially simultaneously with their transmission, whereas the ultrasonic signals travel at the speed of sound which is approximately 1 foot per millisecond. In the illustrative example, a combination RF/ultrasonic transmitter 110, which is referred to herein as a beacon module 110, is coupled to each head wall 101, 102 to transmit the RF locating signal and the ultrasonic locating signal. Devices 110 may be mounted to other portions of room 10, such to a room wall, or to some other structure in the room.

Because the time lag between the RF and ultrasound locating signals is determinable, a distance between each of the MDA's 30 and a point of transmission of the RF and ultrasound signals (referenced to herein as a "reference point" although some point other that the point of signal transmission may be designated and mathematically accounted for and also be considered a "reference point" herein) may be determined by an association computer. The association computer may be module 14 or a computer of locating and tracking system 70 or some other computer as desired. The association computer, therefore, is operable to determine a distance to each device 12 of the plurality of devices 12 from a first reference point associated with the first patient and from a second reference point associated with the second patient based on the distances between the beacon modules 110 and MDA's 30 that are coupled to devices 12.

The association computer may be programmed, for example, such that any devices within a first predetermined distance (e.g., five or six feet, or more or less) from the first reference point are associated with the first patient and such that any devices within a second predetermined distance from the second reference point are associated with the second patient. The first and second predetermined distances may be substantially equivalent distances or may be different distances. In the illustrative example of FIG. 3, if the length (L) of room is 24 feet with 12 feet being associated with the space occupied by bed 40A and 12 feet being associated with the space occupied by bed 40B, and assuming that the first and second reference points are located midway within the respective spaces (e.g., defined on the beacon modules 110 coupled to respective headwalls 101, 102), an association computer may be programmed such that any devices 12 within six feet of a beacon module 110 are associated with that particular location, bed and/or patient.

In rooms that are asymmetric or otherwise oddly shaped the threshold distances for automatic association may be different from one another.

In those embodiments in which local data collection module 14 is coupled to bed 40, a bed listener module (BLM) 31 is coupled to the bed 40 to receive the RF location signal and the ultrasound signal from the beacon module 110 and to determine a time difference between receipt of the RF and ultrasound location signals and/or a distance between beacon module 110 and BLM 31 in the same manner as described above with regard to the MDA's. The BLM 31 may be coupled via a wired connection to module 14 in such an embodiment. The BLM 31 circuitry is similar to the circuitry of MDA 30, but some of the hardware and software found in the MDA 30 is omitted in the BLM 31 because the data from bed 40 is already communicated to module 40 via wired connections with the bed circuitry. In those embodiments in which module 40 is off of the bed, such as being mounted to a wall or headwall in the room, then an MDA 30 is coupled to bed 40 and the bed data is treated just like data from any of the other devices 12 by the associated MDA 30. In some embodiments contemplated by this disclosure, the BLM 31 is also configured to perform an RF energy scan to determine the best channel for module or bed hub 14 to use for communication.

Even after executing algorithms to attempt to associate devices 12 with patients (or beds or locations) automatically, there may be some ambiguities that need to be resolved in one way or another to associate a device 12 with a particular patient (directly or via associating the device 12 with a bed 40 or a location in a healthcare facility). For example, as among two like devices 12 in the room, that may both be beyond the threshold distances mentioned above or that may both be within the threshold distance, the ambiguity may be resolved for the like devices 12 by associating the like device 12 that is closest to the first reference point with the first patient and associating the second of the like devices 12 that is closest to the second reference point with the second patient, regardless of the magnitude of those distances. For example, in FIG. 3, "device 2" and "device 4" are beyond 6 feet from transmitter 110 of headwall 101 and "device 6" and "device 8" are beyond 6 feet from transmitter 110 of headwall 102.

With regard to ambiguities regarding which patient care device 12 is associated with which patient, it is also contemplated that data via Ethernet 24 from a remote computer may be obtained by the association computer and the ambiguity resolved based on the data obtained from the remote computer. The remote computer may be part of an electronic medical records (EMR) system 72 and/or an admission, discharge, and transfer (ADT) system 74, for example. The remote computer may be part of a workflow system 76 or a Nurse Call system 78 or any other computer system in the healthcare facility. For example, if data in the EMR and/or ADT system indicate that a first patient in a room has had knee replacement surgery and that a second patient in the room has had a heart attack, the association computer may use this data to associate a passive motion machine with the first patient and an EKG with the second patient.

Any ambiguities as to whether at least one device 12 of the plurality of devices 12 is associated with the first patient or the second patient may be resolved by prompting a user on display 60 or on a display of the association computer (if module 14 is not serving as the association computer) to provide information to resolve the ambiguity. The user then resolves the ambiguity manually by typing the needed information or touching a touch screen, for example, in the appropriate place or via any other method of data entry.

During the process of associating devices 12 having MDA's 30 with a particular bed 40 or room location, the devices 12 with MDA's 30 are moved into an association field (sometimes referred to as an association cloud) near beacon module 110. Once the devices 12 and MDA's 30 are associated, they do not need to remain in the association field, but should remain within the communication range of module 14 unless MDA's 30 are of the type that capable of establishing a mesh network, in which case only one of the MDA's 30 need to remain within communication distance of hub 14. After the association is made, module or bed hub 14 communicates with the MDA 30 to recognize the particular type of medical device 12 to which the MDA 30 is coupled and to load the appropriate device driver software and protocols.

It is contemplated by this disclosure that display 60 may be included in a heads up type display system integrated into glasses or goggles worn by a caregiver. It is also contemplated that the data received by module 14 as well as any alarm conditions or alert conditions that are determined based on that data could be transmitted via a communication system 80 to a handheld wireless communication device carried by an assigned caregiver or caregivers. Such handheld communication devices may include, for example, PDA's, Vocera™ badges, ASCOM™ handsets, or Spectralink™ handsets, just to name a few. See U.S. Pat. No. 7,319,386, which is hereby incorporated by reference herein, for additional details of communication systems 80 associated with Vocera™ badges, ASCOM™ handsets, or Spectralink™ handsets and the transmission of alarms and alerts to these.

Referring now to FIG. 9, a system 200 similar to system 10 is shown diagrammatically. Because of the similarities between system 200 and system 10, like reference numerals are used to denote like components. Unlike system 10 which had local data collection module 14 and display 60 coupled to bed 40, system 200 has a combination local data collection module and display, indicated diagrammatically at block 1460, mounted to a head wall in the hospital room. The combination local data collection module and display is referred to herein as a "wall hub 1460." In one embodiment, wall hub 1460 is a JACE2700 available from Tridium, Inc. of Richmond, Va. In FIG. 9, a patient 202 is shown diagrammatically on bed 40 and a number of lines 204 are shown diagrammatically interconnecting the patient 202 with the various medical devices 12. Thus, lines 204 are illustrative of the various monitor leads and care delivery tubes that are used in connection with patient care in a healthcare facility.

Wall hub 1460 receives wireless data signals from the MDA's that are coupled to devices 12 and also stores drivers for MDA's 30 as well as storing backup data for the patient. The drivers stored in memory of wall hub 1460 are custom software modules written for each medical device 12 to which an MDA 30 may be coupled and the drivers include rules defining valid data for each device 12. Thus, the drivers account for any protocol conversion that may need to take place to permit communication between the wall hub 1460 and the medical devices 12 and/or between wall hub 1460 and other systems such as EMR system 72 and ADT system 74.

In one embodiment, in connection with wall hub 1460 establishing communications with a particular device 12, the wall hub 1460 receives data from the particular devices 12, such as a model number or device type number or other identification information, from which the type of device 12 can be determined by wall hub 1460. The wall hub 1460 then determines whether device driver software for that particular type of device is stored in its memory. If wall hub 1460 does not have the device driver software for the particular device 12, then wall hub 1460 requests the device driver software from a hub server 206 which, according to this disclosure, contains a library of device driver software for the various types of devices 12 that are present in the healthcare facility and which have been designated for communication with wall hub 1460. Hub server 206 then responds by transmitting the requested device driver software to wall hub 1460 for storage and use. When using the device driver software, wall hub 1460 uses the driver information to determine if medical data is being communicated, to determine if the data is valid, and to display device information on the display of wall hub 1460. The foregoing description regarding the manner in which wall hub 1460 operates to communicate with hub server 206 to obtain device driver software is applicable to module 14 as well, in some embodiments, including display of data on display 60 that is communicatively coupled to module 14.

The data gathered by wall hub 1460 from the various medical devices 12 via MDA's 30 is communicated to the EMR system 72 for automatic entry into the patient's electronic medical record. In connection with associating the various medical devices 12 with the patient being monitored by, or receiving care from, devices 12, wall hub 1460 receives information from ADT system 74. In the illustrative example of FIG. 9, the information from ADT system 74 is routed through hub supervisor 206, which includes a server with a display for system administration and biomedical configuration. Information received by wall hub 1460 from ADT system 74 includes, for example, the name of the patient that has been assigned to the particular room location where the wall hub 1460 is located.

Unlike system 10 which, in the illustrative example above, is programmed and configured to provide on display 60 a local data display of a wide variety of data acquired from devices 12 and to provide alarming capabilities when alarm conditions are indicated on one or more of devices 12, the primary purpose of system 200 is to acquire data from the devices 12 in communication with wall hub 1460 and to transmit that data to the EMR system 72 for automatic storage of at least some of the acquired data in the patient's electronic medical record. System 200, therefore, reduces or possibly, altogether eliminates, the need for a caregiver to manually enter the data from devices 12 onto a written or electronic chart thereby enhancing overall caregiver efficiency.

Figure 10:
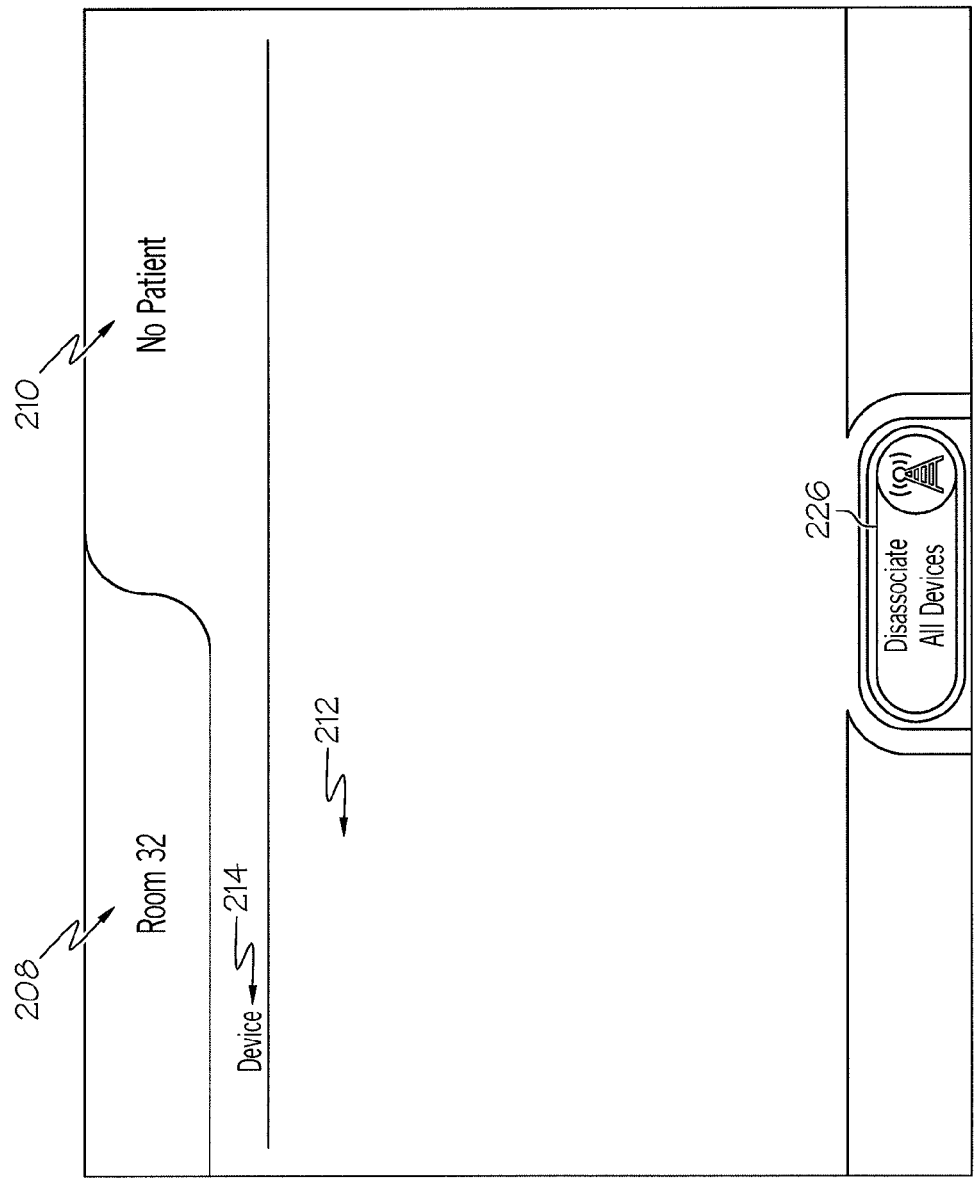
FIG. 10 is a screen shot of a display that is integrated with or coupled to the wall hub of FIG. 9 showing the room number in which the wall hub and display are located in the upper left portion of the screen, an indication of "No Patient" in the upper right portion of the screen to indicate that no patient has been assigned to the room, and a field beneath a "Device" header that is empty to indicate that the system of FIG. 9 is in a state in which no wireless communication between the wall hub and any patient care devices is taking place.

FIGS. 10-15 provide examples of screen shots that appear on the display of wall hub 1460 in connection with the operation of system 200. Referring to FIG. 10, a room number field 208 is provided in the upper left portion of the screen to provide an area for display of the number of the room in which the wall hub is located. In the example of FIG. 10, "Room 32" is shown in field 208. The screen shot of FIG. 10 also has a name field 210 in the upper right portion of the screen to provide an area for the name of a patient to be displayed. In the example of FIG. 10, "No Patient" is displayed in field 210 to indicate that no patient has been assigned to the room. The screen shot of FIG. 10 also has a field 212 beneath a "Device" header 214 that is empty to indicate that the system of FIG. 9 is in a state in which no wireless communication between the wall hub 1460 and any patient care devices 12 is taking place.

Figure 11:
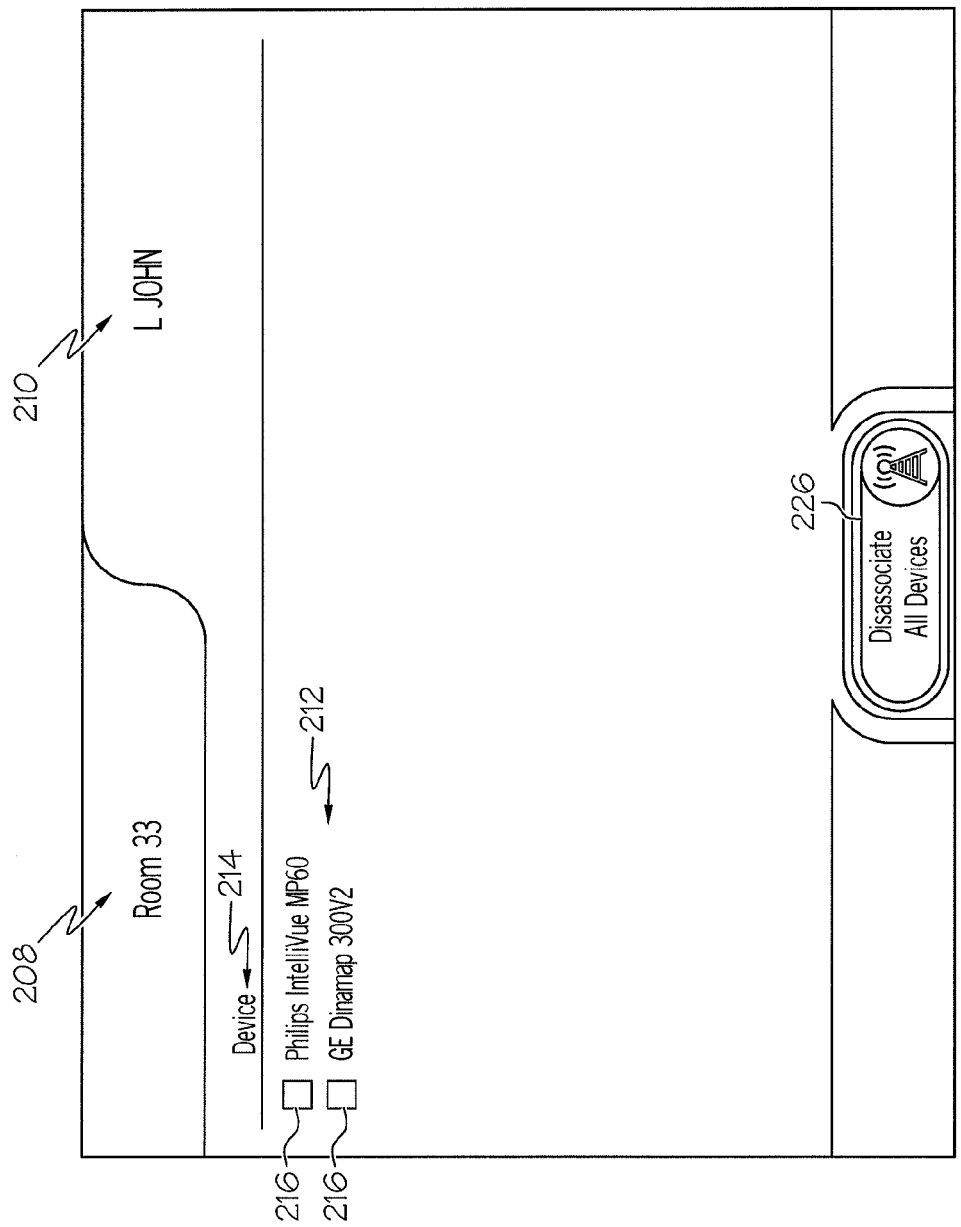
FIG. 11 is a screen shot, similar to FIG. 10, showing the name of an associated patient in the upper right portion of the screen and showing beneath the "Device" header the names of two devices which are in communication with the wall hub.
Figure 12:
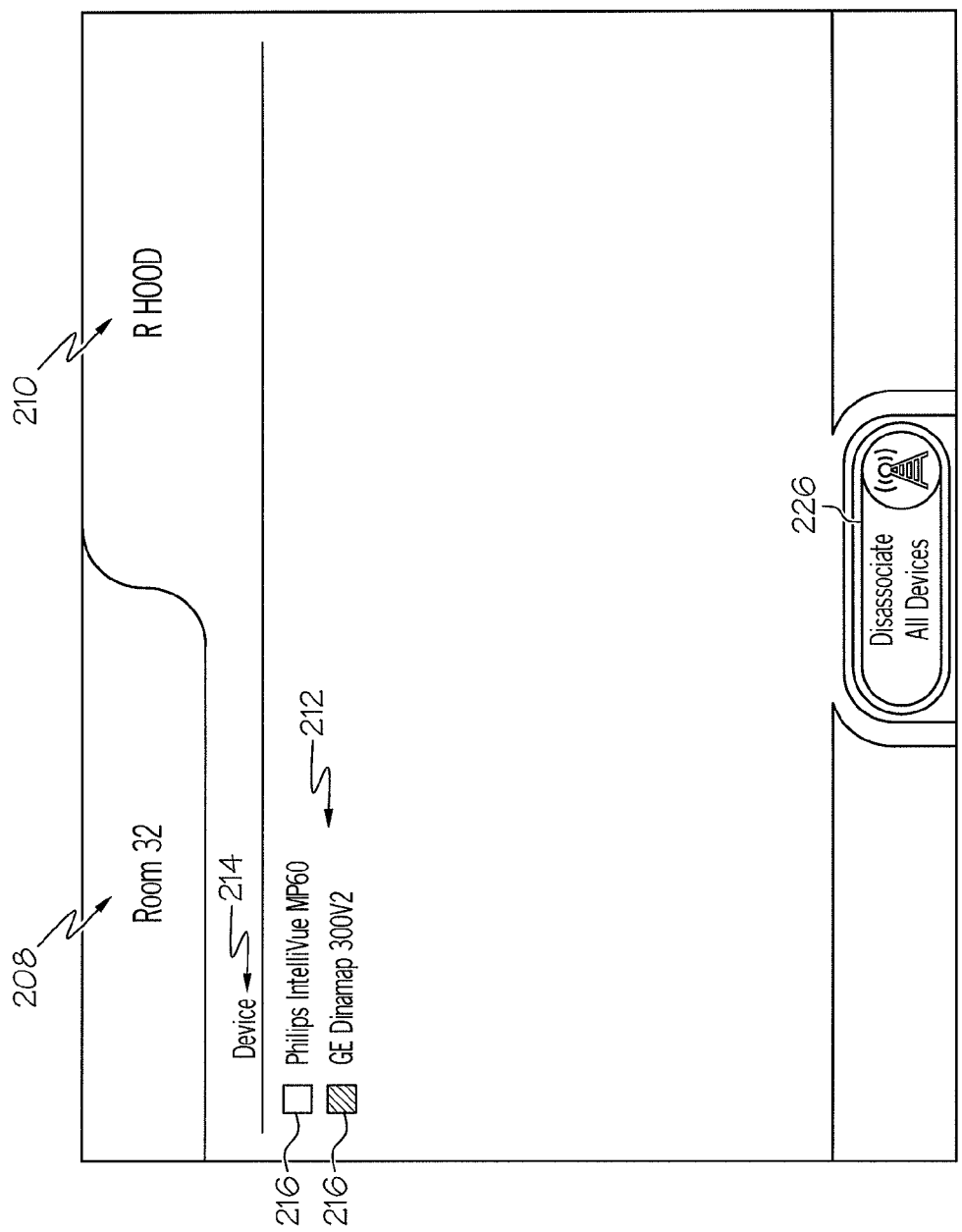
FIG. 12 is a screen shot, similar to FIG. 11, showing that a status box next to one of the device names beneath the "Device" header has been color coded, wherein a color code of green means that the wall hub is currently receiving data from the associated device and a color code of yellow indicates that some sort of communication fault is occurring.

Once a patient has been assigned to the room the patient's name appears in field 210 in a HIPAA compliant format as shown in FIG. 11. In addition, once medical devices 12 have established communications with wall hub 1460, the names of the medical devices are listed in field 212 under the Devices heading 214. In the illustrative example of FIG. 11, a Philips IntelliVue MP60 and a GE Dinamap 300V2 are in communication with wall hub 1460. Next to each of the device names in field 212 is a status box 216. The status boxes 216 are filled with particular colors to indicate that certain events are occurring. In FIG. 12, for example, the status box 216 next to the GE Dinamap 300V2 is shaded to indicate that an event is occurring.

It is contemplated by this disclosure that a color code of green in status box 216 means that the wall hub is currently receiving data from the associated device and a color code of yellow in the status box indicates that some sort of communication fault is occurring. In some embodiments, status box 216 is color coded red to indicate that some type of alarm is occurring or is sensed by the associated medical device 12. However, in the illustrative example, system 200 is configured not to indicate any alarms so as to avoid being subject to certain requirements of the Food and Drug Administration (FDA) that are applicable to medical systems which alarm. Thus, system 200 is programmed to be a non-alarming system that captures patient data and medical device data from patient monitoring equipment and that transmits the data to the patient electronic medical record where the data is stored.

Figure 13:
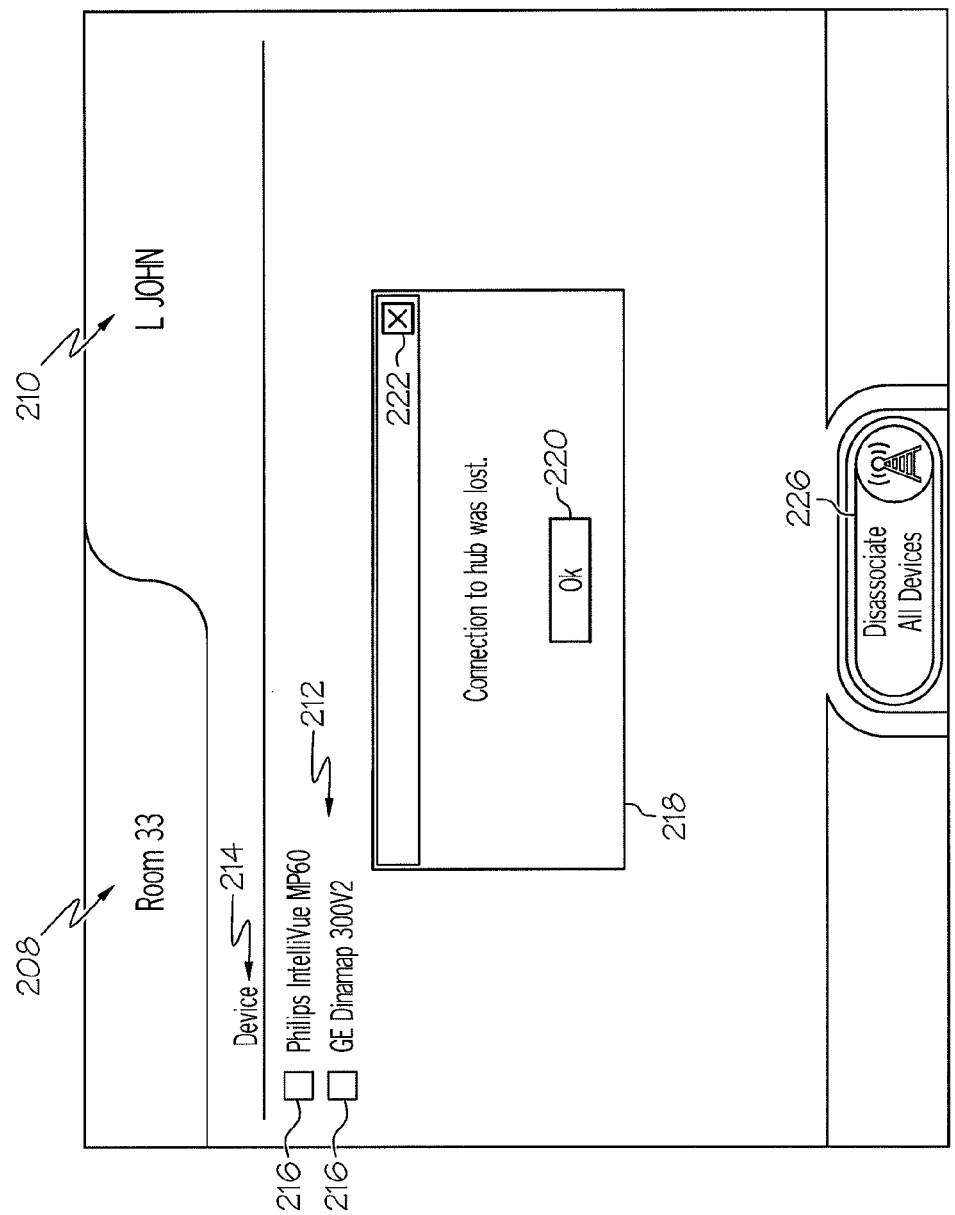
FIG. 13 is a screen shot, similar to FIGS. 10-12, showing a pop up window that has appeared on the screen with the message "Connection to hub was lost" to indicate that the wall hub is no longer able to communicate with one of the pieces of equipment in the room.
Figure 14:
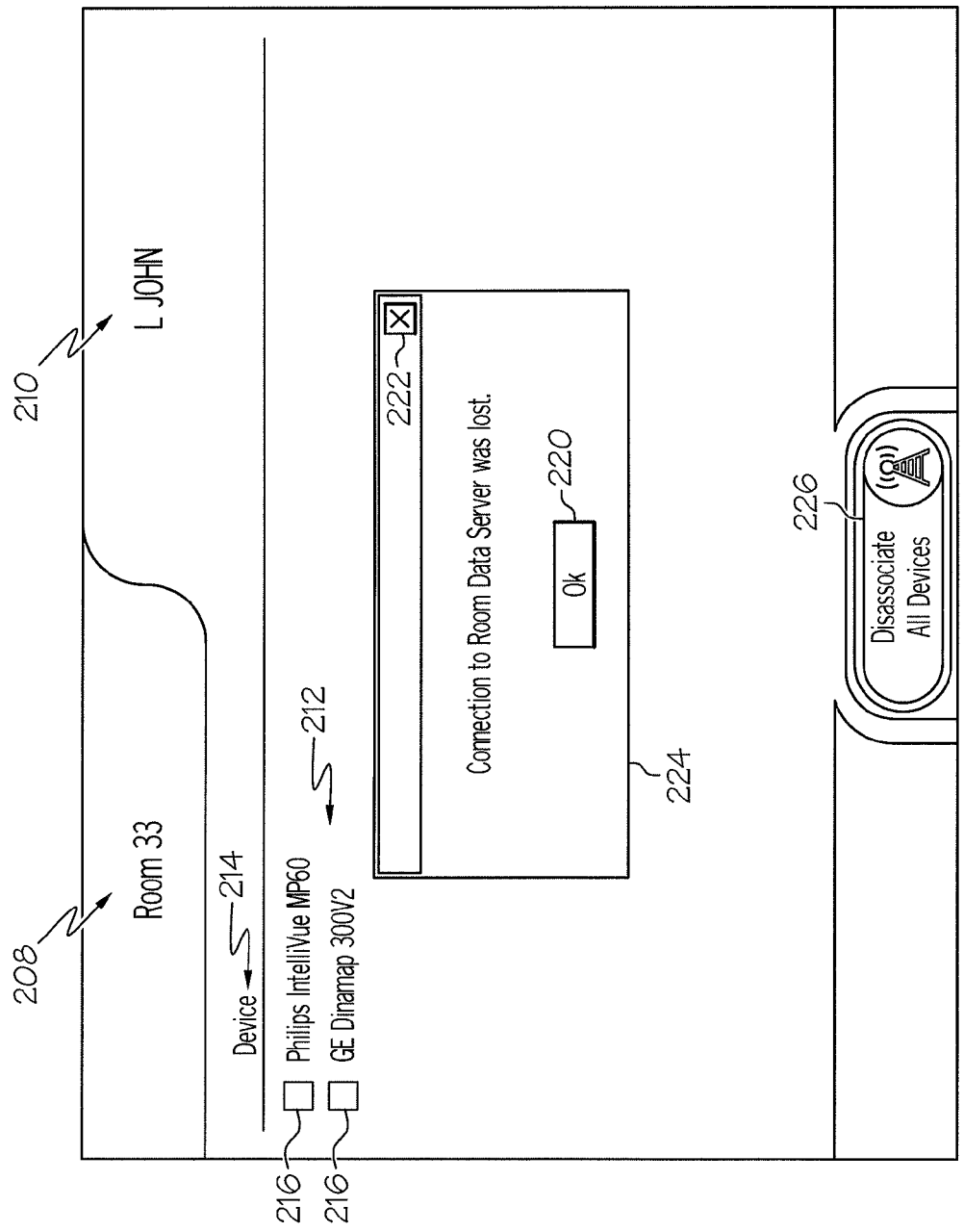
FIG. 14 is a screen shot, similar to FIG. 13, showing a pop up window that has appeared on the screen with the message "Connection to Room Data Server was lost" to indicate that the wall hub is no longer able to communicate with the associated remote server.
Figure 15:
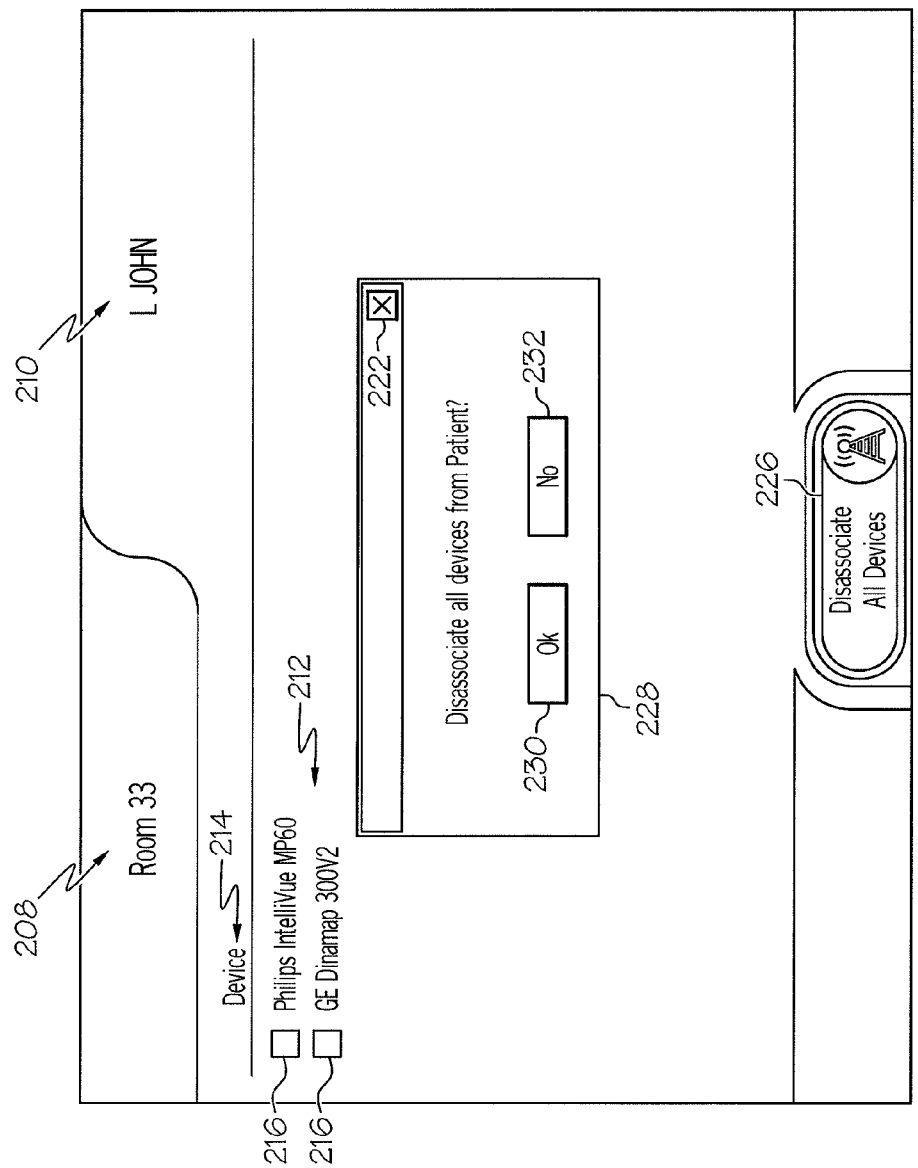
FIG. 15 is a screen shot, similar to FIG. 11, showing a pop up window that has appeared on the screen after a user has selected a "Disassociate All Devices" icon appearing at the bottom of the screen, the pop up window having an "Ok" button that is selectable by a caregiver to confirm that the wall hub should be disassociated from all of the devices in the room and a "No" button if the disassociation between the wall hub and all of the patient care devices in the room should not occur.

As shown in FIG. 13, if communication between the devices 12 in the room and wall hub 1460 is lost completely, then a pop-up window 218 appears on the display of hub 1460 with the message "Connection to hub was lost." A user can close pop-up window 218 by touching, or otherwise selecting, an Ok button 220 or a close box 222. If the wall hub 1460 is no longer able to communicate with the associated remote server 206, a pop-up window 224 with the message "Connection to Room Data Server was lost" appears on the display of hub 1460 as shown in FIG. 13. In some embodiments, when the connection to server 206 is lost, hub 1460 stores incoming data from devices 12 until communication is re-established with server 206 and then the stored data is transmitted. As was the case with window 218, an Ok button 220 and a close box 222 are provided in window 224 to enable a user to close window 224.

As shown in FIGS. 10-15, a "Disassociate All Devices" button or icon 226 is provided on the display of wall hub 1460. Button 226 is touched or otherwise selected to stop data collection from the devices 12 by wall hub 1460. Button 226 may be pressed for example, when the patient has been discharged or when the patient is no longer in need of devices 12. In response to button 226 being selected, a pop-up window 228 with the message "Disassociate all devices from Patient?" appears on the display of hub 1460. A user can then select an Ok button 230 to confirm that all of the devices are to be disassociated from the hub 1460 such that hub 1460 no longer receives data from devices 12 and/or no longer transmits data to the patient's electronic medical record. A user can select either a No button 232 of close box 222 to abort the disassociation. If button 232 or box 222 are selected in window 228 then hub 1460 continues to perform its data collection and communication function.

Figure 16:
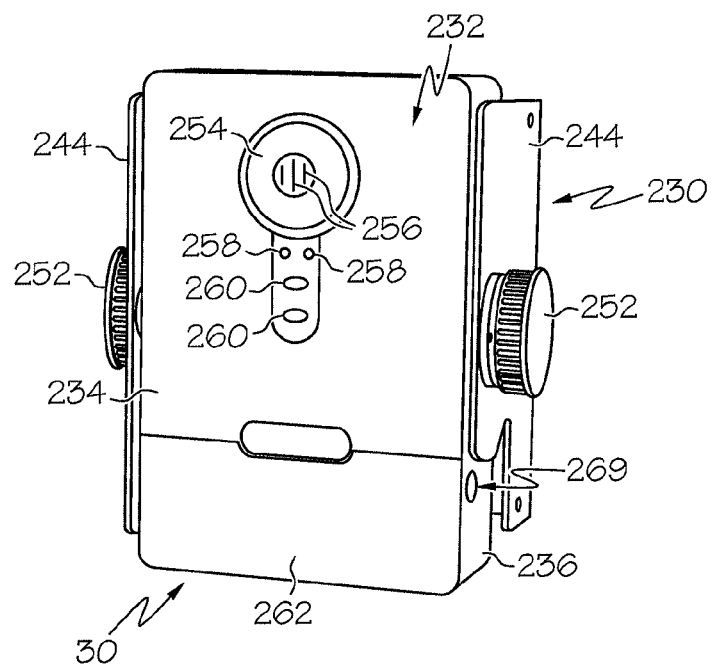
FIG. 16 is a perspective view of one of the MDA's coupled to a mounting bracket.
Figure 17:
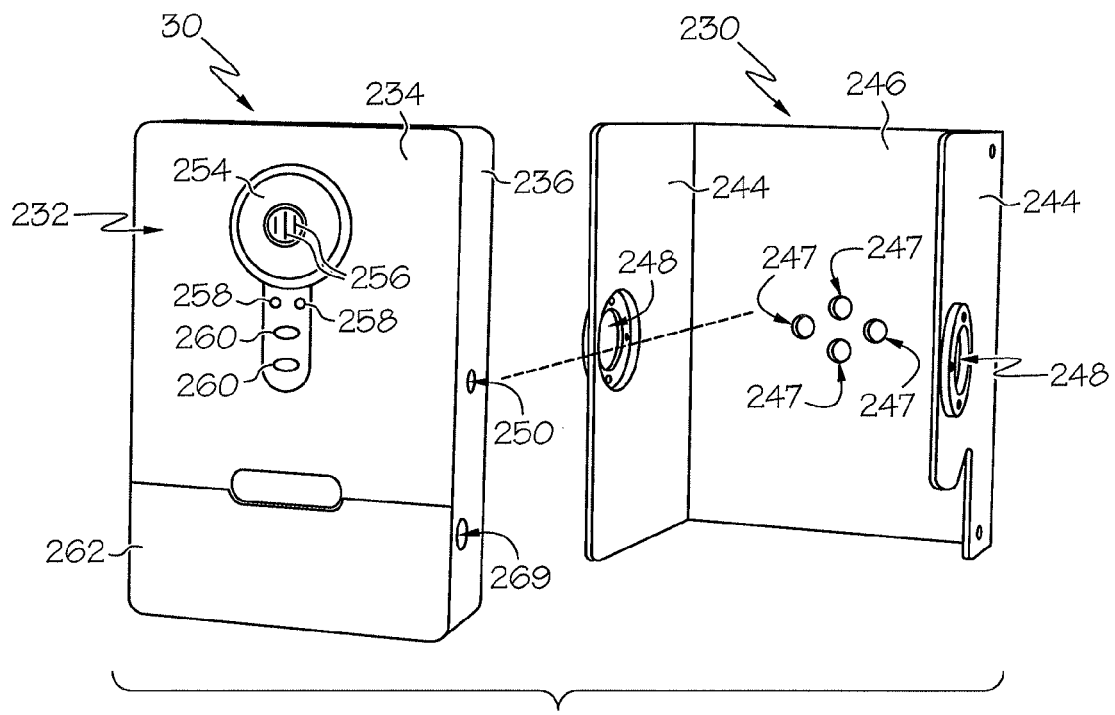
FIG. 17 is an exploded view showing the MDA exploded away from the mounting bracket.
Figure 18:
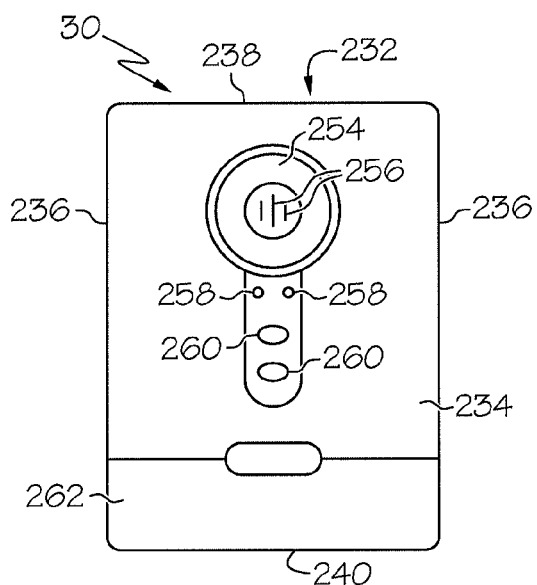
FIG. 18 is a front elevation view of the MDA.

Referring now to FIGS. 16 and 17, an illustrative embodiment of MDA 30 is coupled to a mounting bracket 230 which, in turn, is coupleable to devices 12. MDA 30 includes a housing 232 having a front wall 234, a pair of side walls 236, a top wall 238, a bottom wall 240, and a back wall 242 as shown in FIGS. 16-21. Bracket 230 has a pair of side walls 244 and a back wall 246 that interconnects walls 244 as best shown in FIG. 17. Back wall 246 of bracket 230 has four holes 247 that are located in a central area thereof and that are arranged in a pattern that is compatible with coupling to a Hill-Rom headwall rail mount or to a Hill-Rom IV pole mount. Bracket 244 attaches to medical devices 12 with a suitable coupler such as a clamp, hook-and-loop fasteners (e.g. VELCRO® fasteners), or adhesive, just to name a few.

According to this disclosure, MDA's 30 may mount to power adapters that are coupled to a standard AC wall outlet. That is, the MDA's 30 attach to a power adapter to received power therefrom. A cable is then used to connect the MDA's to associated devices 12 by coupling the cable to the appropriate data ports. Such power adapters for the MDA's may also have an outlet for the associated medicals devices 12 to plug into, such that the power adapter plugs into the wall and the device 12, as well as the associated MDA 30, plugs into the adapter. The power adapter is configured to mount to a pole, such an IV pole, in some embodiments, and in other embodiments, the power adapter may be mounted elsewhere such as to another portion of the bed 40 or to a wall or headwall. The power adapter has a power cord that couples to a standard AC power outlet.

Side walls 244 of bracket 230 each have a hole 248 about midway between the top and the bottom of bracket 230. Side walls 236 of housing 232 each have an aperture 250 therein. Apertures 250 align with holes 248 when MDA 30 is situated between walls 244 of bracket 230. A pair of knobs 252 is provided to fasten MDA 30 in place relative to bracket 230 as shown in FIG. 16. Portions of knobs 252 are received in holes 248 and apertures 250. When knobs 252 are loosened, MDA 30 is able to pivot relative to bracket 230 about an axis that passes through holes 248 and apertures 250. Thus, spacing is provided between back wall 242 of housing 232 and back wall 246 of bracket 230 to allow for the pivoting of the MDA 30 relative to bracket 230. Once MDA 30 is in its desired orientation, knobs 252 are tightened to secure MDA 30 in place relative to bracket 230. Apertures 250 are threaded in some embodiments to receive a threaded screw portion of knobs 252. In other embodiments, threaded nuts are situated adjacent apertures 250 in the interior region of housing 232 to receive the threaded screw portion of knobs 252.

Front wall 234 has a slightly domed disc 254 which has slots 256 in a central region thereof. The ultrasound receiver (illustrated diagrammatically in FIG. 3 as element 52) of MDA 30 is located behind disc 254. Beneath disc 254 are a pair of light emitting diodes (LED's) 258, one of which serves as a status indicator and the other of which serves as a low battery indicator. For example, one of LED's 258 may shine green when data is being acquired and/or transmitted by the MDA 30. The other LED 258 may shine yellow when the battery is low. Suitable text or icons are provided near LED's 258 to indicate the function of each.

MDA 30 also has a pair of buttons 260 which are located beneath LED's 258. One of buttons 260 serves as a "confirm" button for a caregiver to press when a confirmed patient data reading is to be taken from the associated medical device. As compared to the automatic wireless readings that are transmitted by MDA 30, a confirmed reading should be considered to have higher reliability since a caregiver is present to verify that the medical device 12 is operating properly and that the patient is properly hooked up to the device 12. In some embodiments, the "confirm" button, when pressed, serves as a data capture button which allows a caregiver to send data from MDA 30 to bed hub 14 or wall hub 1460 at a time of their choosing. The other button 260 serves as a "disconnect" button that is pressed when the respective medical device 12 is to be removed from the group of medical devices 12 associated with the patient. Suitable text or icons are provided on or near buttons 260 to indicate the function of each. Buttons 260 are membrane switches in some embodiments.

Figure 19:
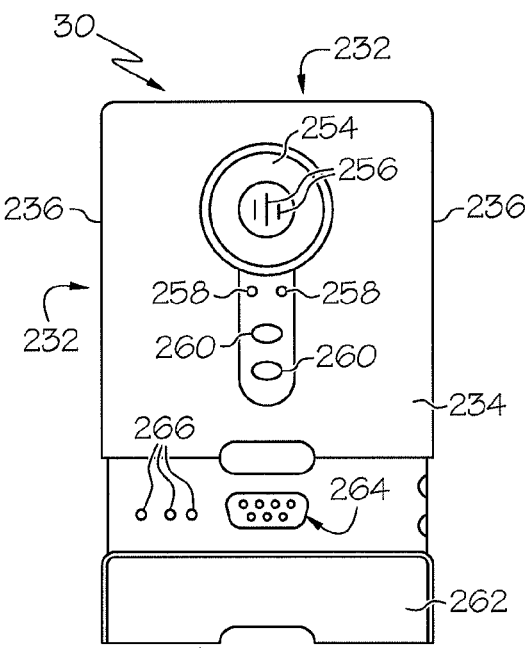
FIG. 19 is a front elevation view of the MDA, similar to FIG. 18, showing a bottom cover flipped down to expose user inputs and an RS-232 data port.
Figure 20:
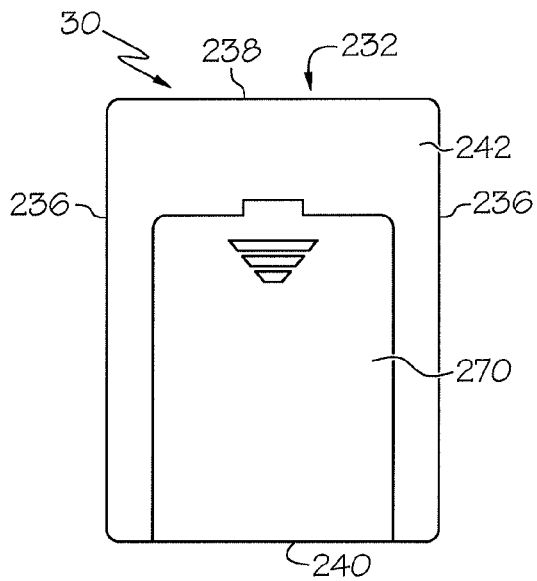
FIG. 20 is a rear elevation view of the MDA, showing a battery door that is removable to replace batteries which power the device.
Figure 21:
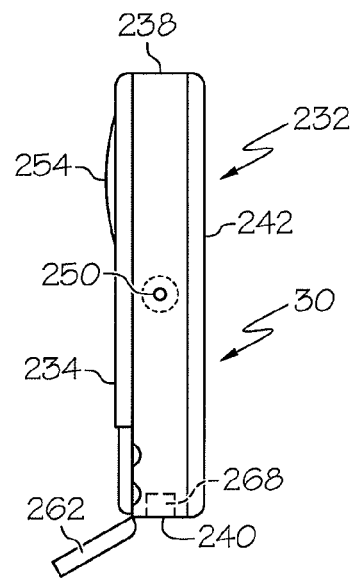
FIG. 21 is a side elevation view of the MDA with the bottom cover flipped open.

MDA 30 has a flip down or drop down access panel or door 262. Panel 262 is movable between a closed position, shown in FIGS. 16-18, and an opened position, shown in FIGS. 19 and 21. When panel 262 is in the opened position, an RS-232 port 264 and set of user inputs 266 are exposed as shown in FIG. 19. Port 264 connects to the associated medical device 12 via an appropriate connector cable. In some embodiments, port 264 is a Universal Serial Bus (USB) port rather the illustrative RS-232 port. Port 264 also provides programming and configuration access to the circuitry of the MDA 30. Thus, another computer device can be coupled to port 264 to configure and program the software of MDA 30. User inputs 266 include a power button, a reset button, and a program and configure button. In some embodiments, an additional port 268, shown in phantom in FIG. 21, is provided so that MDA 30 is coupleable electrically to devices 12 when the panel 262 is in the closed position.

MDA 30 is configured so as to be powered by either a 15.5 Volt DC wall power supply or by a rechargeable battery. A port 269 is provided in one of the sidewalls 236 of housing 232 for coupling to the 15.5 VDC power cord. The rechargeable battery provides short-term power (up to 12 hours) and is, therefore, suitable for powering the MDA 30 during power outages and when the device 12 is mobile, such as when the patient is being moved from one location to another within a healthcare facility while still connected to one or more devices 12. A battery door 270 is provided at the rear of MDA 30 and is removable to allow the batteries to be removed and replaced. In some embodiments, MDA 30 has a low capacity, factory-replaceable backup battery which powers the MDA 30 when the larger batteries are removed. The on/off button of user inputs 266 permits the power to the MDA 30 to be turned off when the MDA 30 will be unused for an extended period of time.

Figure 22:
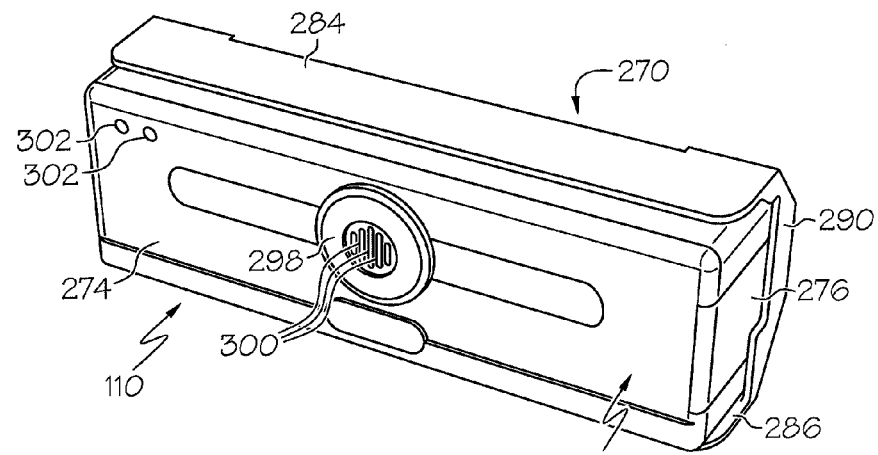
FIG. 22 is a perspective view of one of the beacon modules coupled to a mounting bracket.
Figure 23:
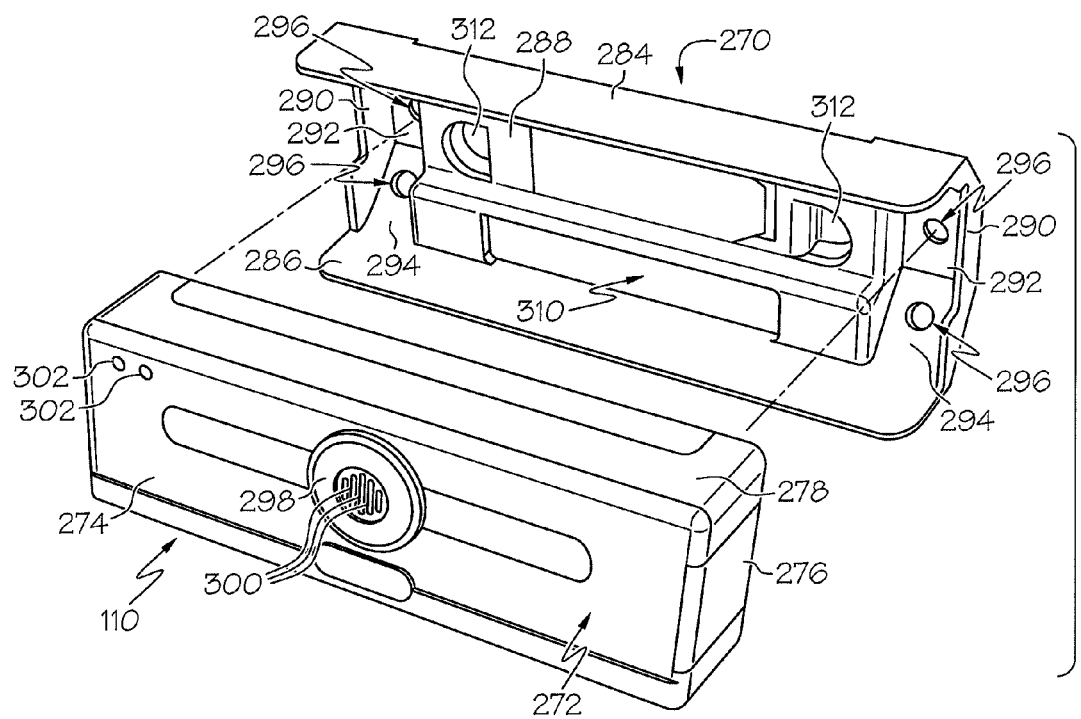
FIG. 23 is an exploded view showing the beacon module exploded away from the mounting bracket.
Figure 24:
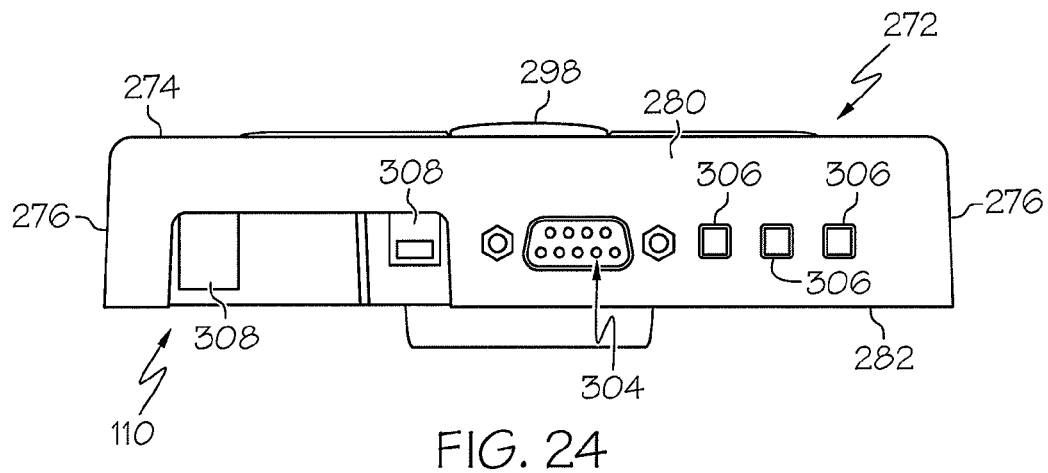
FIG. 24 is a bottom view of the beacon module showing user inputs and data ports of the beacon module.

Referring now to FIGS. 22-24, an illustrative embodiment of beacon module 110 is coupled to a mounting bracket 270 which, in turn, is coupleable to a wall or headwall in a room of a healthcare facility. Beacon module 110 includes a housing 272 having a front wall 274, a pair of side walls 276, a top wall 278, a bottom wall 280, and a back wall 282 as shown in FIGS. 22-24. Bracket 270 has a top wall 284, a bottom wall 286 and a back wall 288 that interconnects walls 284, 286 as best shown in FIG. 23. Bracket 270 also has a pair of relatively small side walls 290 that are interconnected to walls 284, 286, 288.

Opposite end regions of back wall 288 of bracket 270 each have a first wall portion 292 that is generally perpendicular to top wall 284 and a second wall portion 294 that angle from portion 292 to bottom wall 286. A mounting hole 296 is provided in each of portions 292, 294 at each end of bracket 270. Suitable fasteners, such as screws extend through holes 296, to attach bracket 270 to a wall or headwall or any other desired structure within a room of a healthcare facility. Wall portions 294 are provided so that if beacon module is to be mounted relatively high in a room, such as six feet off of the floor or higher, for example, then bracket 270 can be tilted downwardly at about a forty-five degree angle having portions 294 abutting a vertical wall or surface and then fastened thereto. Of course, bracket 270 can be mounted in a non-tilted orientation by having wall portions 292 abutting the vertical surface to which bracket 270 is mounted. Thus, screws are received either by holes 296 of wall portion 292 or holes 296 of wall portion 294 depending upon the orientation at which bracket 270 is to be mounted.

Front wall 274 of beacon module 110 has a slightly domed disc 298 which has slots 300 in a central region thereof as shown in FIGS. 22 and 23. An ultrasound transmitter of module 110 is located behind disc 298 in the interior region of housing 272. In the illustrative example, module 110 is configured to send an RF signal according to the 802.15.4 protocol (i.e., Zigbee protocol) along with the ultrasound signal. Module 110 also has a pair of light emitting diodes (LED's) 302 in an upper region of one of the corners of front wall 274. LED's 302 serve as a status indicators. For example, one of LED's 302 may shine green when RF and ultrasound signals are being transmitted by beacon module 110. The other LED 302 may shine yellow when a fault condition is detected within the circuitry of module 110. Suitable text or icons are provided near LED's 302 to indicate the function of each.

Accessible on bottom wall 280 of housing 272 of module 110 are an RS-232 port 304, a set of user inputs 306, and a pair of power connection ports 308 as shown in FIG. 24. Port 304 provides connectivity to an external computer device for programming and configuration of the circuitry of module 110. User inputs 306 include a Restore Default Configuration button, a Reset button, and a Program Mode button. Module 110 is configured so as to be powered by a 15.5 Volt DC wall power supply and, in some embodiments, ports 308 comprise a standard power co-axial jack. Ports 308 are configured to couple to 15.5 VDC power cords via other types of connectors in other embodiments. Two ports 308 are provided in the event that a second beacon module 110 is used within the room, in which case power can be daisy changed from one beacon module 110 to the other via a suitable power cord. Thus, one of ports 308 is a power input port and the other of ports 308 is a power output port. Module 110 can receive its power at the power input port 308 from a wall-mounted or headwall-mounted display 60 or from a wall hub 1460 or from a standard wall supply.

Ports 304, 308 and user inputs 306 are concealed from view when module 110 is received in bracket 270. However, ports 308 are recessed relative to the rest of bottom wall 280 up into module 110 by a sufficient distance to accommodate the power connectors that couple to one or both of ports 308. Bracket 270 has a large opening 310 in back wall 288 to allow for the routing of power cords therethrough. Back wall 288 is also molded to have a pair of cord wrap tabs 312 around which excess slack of the one or both power cords can be wrapped, if desired. Each beacon module 110 is linked in a database, such as a database of hub server 206, with the room in which it is installed. In rooms having two or more beds, beacon modules 110 may linked in the database with only a portion of the room (e.g., the portion having bed A or the portion having bed B in a particular room).

Figure 25:
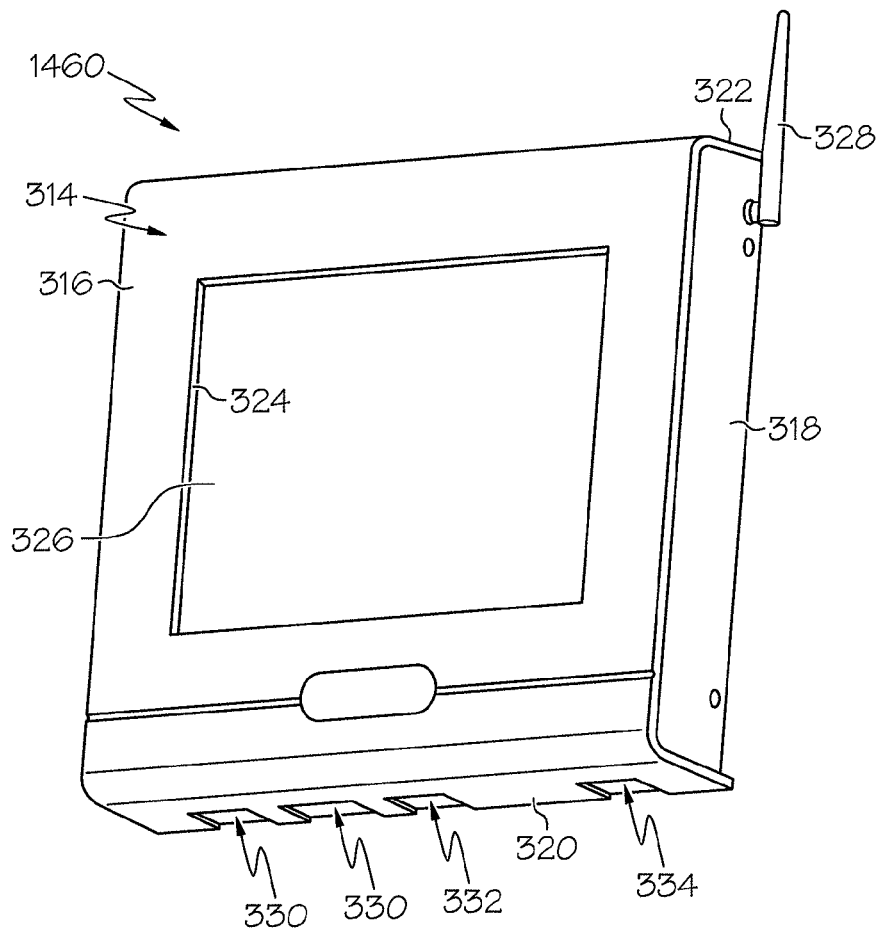
FIG. 25 is a perspective view of a display module showing the display module having an antenna coupled to a sidewall of the display module.

One embodiment of a wall hub 1460 is shown in FIG. 25. Hub 1460 has a housing 314 including a front wall 316, a pair of sidewalls 318, a bottom wall 320, and a top wall 322. The back wall (not shown) of hub 1460 has a 3-hole pattern for attaching hub 1460 to a wall, headwall or another suitable mounting surface. In those embodiments in which the local data collection module 14 and display 60 are integrated together into wall hub 1460, then the circuitry of module 14 is packaged within housing 314. In those embodiments in which the local data collection module 14 is separate from display 60, such as when module 14 is coupled to hospital bed 40, then the circuitry of module 14 is omitted within housing 314. Front wall 316 has a large rectangular opening 324 through which a touch screen 326 can be viewed and accessed. A WiFi antenna 328 is mounted to one of sidewalls 318 as shown in FIG. 25. Antenna 328 receives the 802.11 wireless signals from module 14 in those embodiments in which module 14 is mounted to hospital bed 40. Antenna 328 is also used for bidirectional wireless communications with other wireless access points 22 of Ethernet 24 according to the 802.11 protocol when the circuitry of module 14 is included within housing 314 to form wall hub 1460.

In the illustrative example, two 10/100 Ethernet ports 330 are accessible on bottom wall 320 for wired coupling of hub 1460 to the Ethernet 24 of the healthcare facility. Hub 1460 has a 120 Volts AC input port 332 and a 15 VDC output port 334. In some embodiments, output port 334 is a standard DC power co-axial jack, although port 334 may have other DC power connector configuration in other embodiments. Thus, hub 1460 has circuitry to convert 120 VAC received from a standard wall outlet into 15.5 VDC for powering up to two beacon modules 110. Also in the illustrative example, touch screen 326 is a ten inch diagonal color liquid crystal display (LCD) resistive touch screen that has resolution of 800 by 600 Super Video Graphics Array (SVGA) pixels. Touch screens of different types and different sizes than those of the illustrative example are contemplated within the scope of this disclosure as well.

In some embodiments, hub 1460 has a controller with an onboard rechargeable Nickel Metal Hydride (NiMH) battery pack. The battery pack allows hub 1460 to continue to operate through short power bumps, such as those that are a few seconds in duration. If a longer power outage occurs, the NiMH battery pack provides enough run time for the hub 1460 to store backup data in memory and then shut down.

Figure 26:
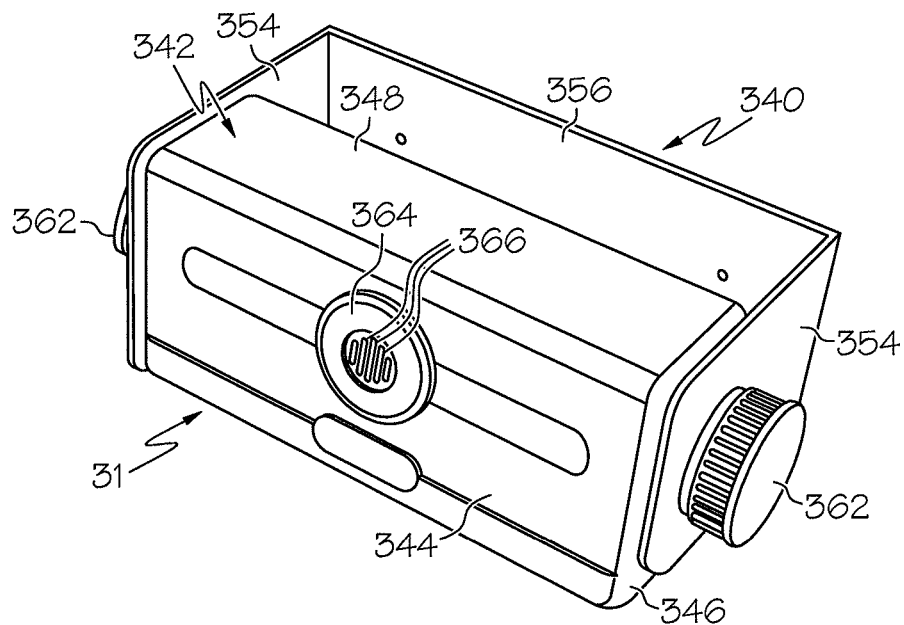
FIG. 26 is a perspective view of one of the BLM's coupled to a mounting bracket.
Figure 27:
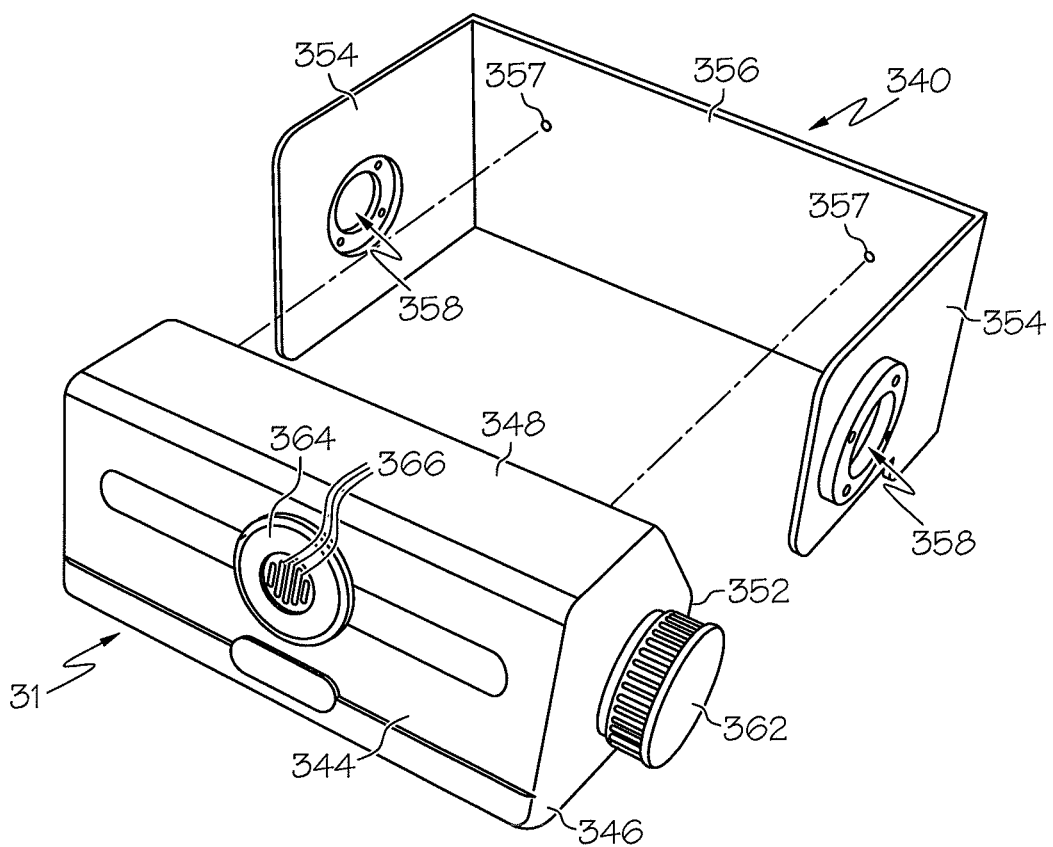
FIG. 27 is an exploded perspective view showing the BLM exploded away from the mounting bracket.
Figure 28:
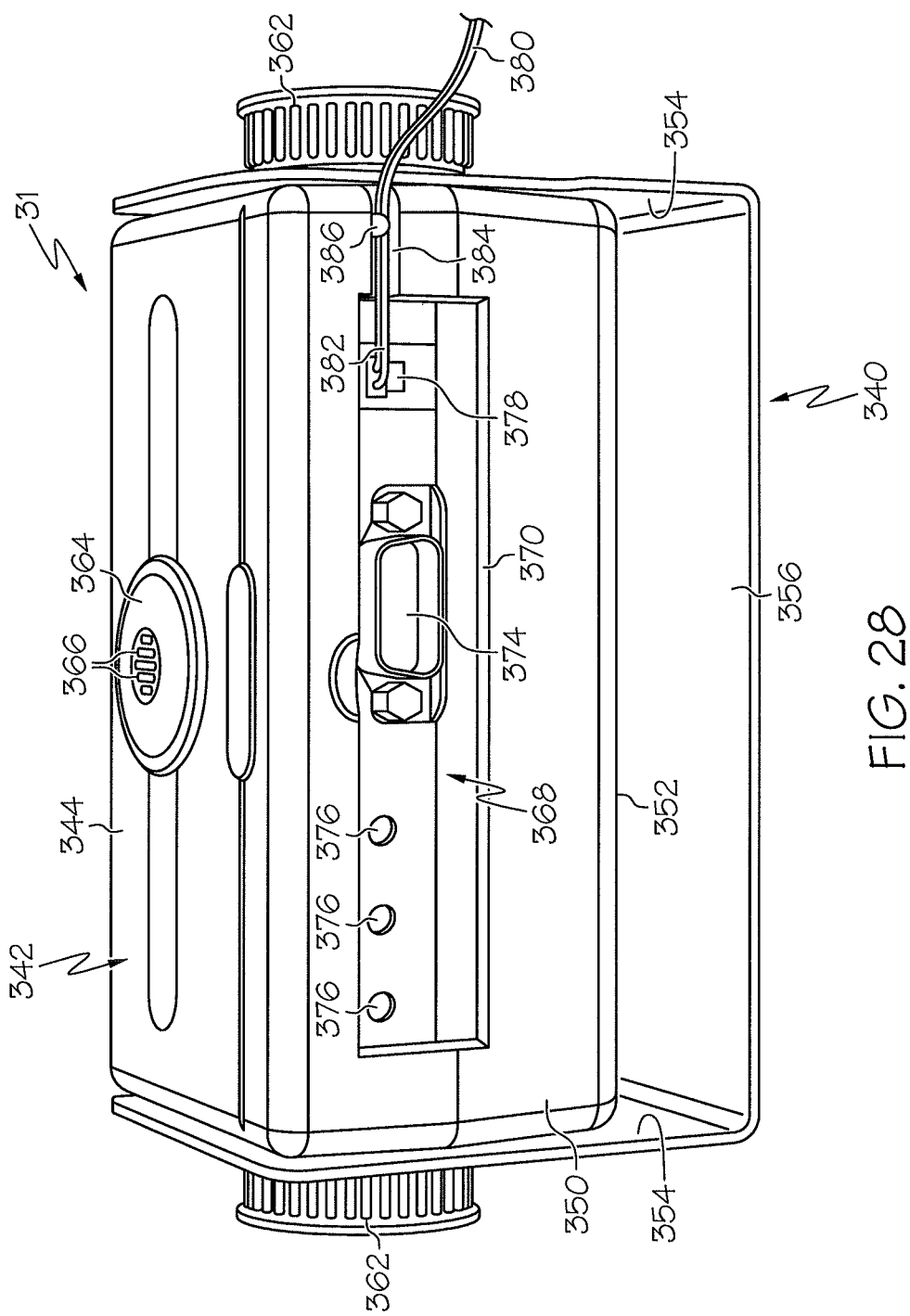
FIG. 28 is a perspective view showing a bottom of the BLM having user inputs and data ports.

Referring now to FIGS. 26-28, an illustrative embodiment of BLM 31 is coupled to a mounting bracket 340 which, in turn, is coupleable to the hospital bed 40. BLM 31 includes a housing 342 having a front wall 344, a pair of side walls 346, a top wall 348, a bottom wall 350, and a back wall 252 as shown in FIGS. 26-28. Bracket 340 has a pair of side walls 354 and a back wall 356 that interconnects walls 354 as best shown in FIG. 12. Back wall 356 of bracket 230 has two holes 357 that provide mounting locations to attach bracket 340 and BLM 31 to hospital bed 40 with a suitable couplers such as bolts or screws. In some embodiments, bracket 31 has a peel and stick adhesive on the back of rear wall 356 for attaching to the bed 40. Other fasteners, such as a clamp, hook-and-loop fasteners (e.g. VELCRO® fasteners), or straps, just to name a few, can be used to attach bracket 340 to hospital bed 40 if desired. Side walls 354 of bracket 340 each have a hole 358 about midway between the top and the bottom of bracket 340. Side walls 356 of housing 232 each have an aperture (not shown but similar to aperture 250 in each sidewall 236 of MDA 30) therein. The apertures in side walls 346 align with holes 358 when BLM 31 is situated between walls 354 of bracket 340.

A pair of knobs 362 is provided to fasten BLM 31 in place relative to bracket 340 as shown in FIG. 26. Portions of knobs 362 are received in holes 358 and the apertures in sidewalls 346. When knobs 362 are loosened, BLM 31 is able to pivot relative to bracket 340 about an axis that passes through holes 358. Thus, spacing is provided between back wall 352 of housing 342 and back wall 356 of bracket 340 to allow for the pivoting of the BLM 31 relative to bracket

340. BLM 31 may be pivoted for example to have its ultrasound receiver aimed more in the direction of beacon modules 110. Once BLM 31 is in its desired orientation, knobs 362 are tightened to secure BLM 31 in place relative to bracket 340. The apertures in sidewalls 346 are threaded in some embodiments to receive a threaded screw portion of knobs 362. In other embodiments, threaded nuts are situated adjacent these apertures in the interior region of housing 342 to receive the threaded screw portion of knobs 362.

Front wall 344 has a slightly domed disc 364 which has slots 366 in a central region thereof. The ultrasound receiver of BLM 31 is located behind disc 364. A green status indicator LED (not shown) may be provided in some embodiments to indicate the proper functioning of BLM 31.

A recessed area 368 is accessible through a large opening 370 provided in bottom wall 350 of housing 342 as shown in FIG. 28. Accessible within area 368 are an RS-232 port 374, set of user inputs 376, and a power port 378. Port 374 provides programming and configuration access to the circuitry of the BLM 31. Thus, another computer device can be coupled to port 374 to configure and program the software of BLM 31. User inputs 376 include a restore configuration button, a program button, and a reset button. In some embodiments, a pivotable access panel is provided to close opening 370 to block access to area 368.

Port 374 is also is coupleable to local data collection module 14 via a suitable coupling cord so that the time difference based on the RF and ultrasound signals received by the BLM 31 from the beacon module 110 can be communicated from the BLM 31 to module 14. In some embodiments, BLM 31 may include a wireless transceiver that is operable to transmit the time difference wirelessly to module 14 on the bed and/or to module 1460 on the wall or headwall or other support structure. Such a BLM 31 with wireless transmission capability may be used, for example, in a system in which an MDA 30 is not used to transmit bed status data to module 1460, but the distance of bed from beacon 110 is still desired to be known.

BLM 31 is configured so as to be powered by a 15.5 Volt DC power supply. Accordingly, power port 378 is provided in recessed area 368 for coupling to a 15.5 VDC power connector 382 at the end of a power cord 380. In some embodiments, power cord 380 receives the 15.5 VDC power from the local data collection module 14 on bed 40. Bottom wall 350 of housing 342 has a wire routing groove 384 which receives a portion of power cord 380 therein and a retention tab 386 that retains power cord 380 within groove 384. In one embodiment, port 378 comprises a Tyco 5-103673-1 connector and power connector 382 comprises a Tyco 5-103957-1 connector. In some embodiments, bed hub 14 provides the 15.5 VDC power to the BLM 31 via a suitable power cable. In embodiments in which bed hub 14 is omitted from the bed, such as embodiments using wall hub 1460, then the 15.5 VDC power is provided by the electrical system of the bed. When BLM 31 receives power from bed hub 14, the back-up battery of bed hub 14 also provides back-up battery for the BLM 31 when back-up battery power is needed.

Figure 29:
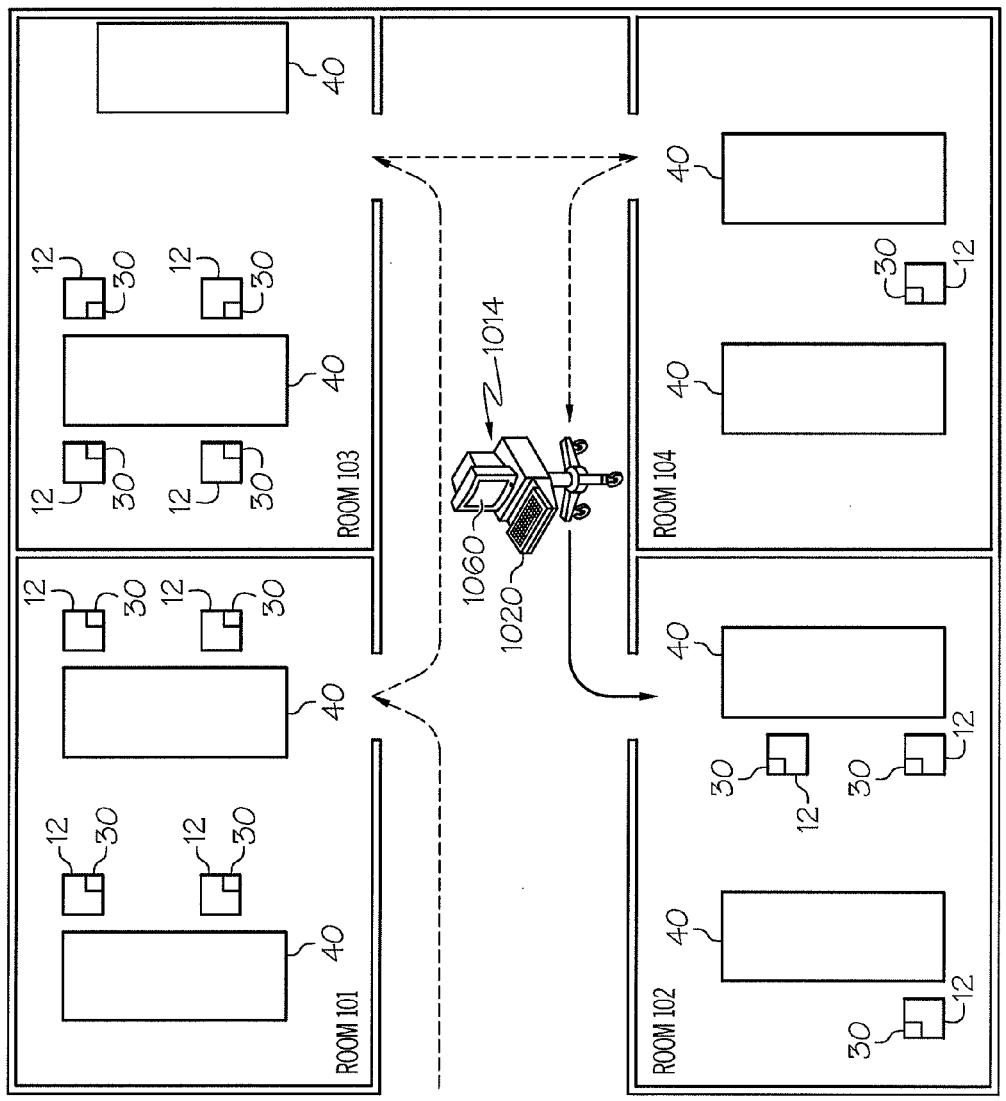
FIG. 29 is a diagrammatic view of an alternative embodiment of a system in which a local data collection module is included as part of a computer on wheels (COW) that is wheeled from room-to-room to collect data from the MDA's coupled to the patient care devices associated with each patient in the room.

Referring now to FIG. 29, a computer on wheels (COW) 1014 is operable as a local data collection module and is wheeled from room-to-room to collect data from MDA's 30 that are coupled to patient care devices 12 in the room. In such an embodiment, a display 1060 of the COW 1014 may prompt a caregiver to select which devices 12 in wireless communication with the COW 1014 within a particular room are to be associated with a particular patient for which data is to be logged automatically. In some embodiments, after the COW 1014 receives the data from the MDA's 30 of the patient care devices 12 associated with a particular patient, the COW 1014 transmits the data wirelessly to an EMR computer 72 via the hospital Ethernet 24. In other embodiments, the COW 1014 may simply store the acquired data for the particular patient for transmission to the EMR computer 72 at a later time.

By using the COW 1014, a caregiver can go from room-to-room and acquire data for automatic logging into the medical records of the various patients in these rooms. In the illustrative example, a caregiver has transported the COW 1014 into rooms 101, 103, and 104, as indicated by the diagrammatic dashed path arrows in FIG. 29, and is getting ready to enter room 102 as indicated by the diagrammatic solid arrow in FIG. 29. In some embodiments, the data acquisition is done automatically by the COW 1014 thereby reducing or eliminating the amount of manual data acquisition and/or data entry that needs to be done by the caregiver.

In some embodiments, the caregiver may be required to perform some amount of data entry using a keyboard 1020 associated with the COW 1014, for example. The caregiver may be prompted, for example, to confirm which devices 12 listed on display 1060 of COW 1014 are associated with a particular patient in the room, to select the devices 12 from which the data is to be logged automatically by the COW 1014 (if data from all devices 12 is not be logged), and to select the particular type of data from the devices 12 that is to be logged automatically by the COW 1014 (if only a subset of data from a particular device 12 is to be logged). However, the more electronic data than can be acquired automatically by the COW 1014 from the patient care devices 12 via the MDA's 30, the less chance there is for human error.

Having a system in which a COW 1014 is used reduces the overall cost of the system because modules 14 and/or 1460 don't need to be placed in each room. However, the trade off is that a caregiver needs to take the time to move the COW 1014 from room to room to acquire the desired data from devices 12 via MDA's 30. Furthermore, because the data transfer between COW 1014 is according to the 802.15.4 protocol, in some embodiments, the COW 1014 needs to be brought into the room by a sufficient distance to permit the short range wireless communications between COW 1014 and MDA's to take place. In those embodiments, in which MDA's 30 for each particular patient are operable to form their own mesh network, then the COW 1014 only needs to be brought within communication range of one of the MDA's 30 for each patient and the data from the other MDA's 30 is communicated to the COW 1014 via the mesh network and the MDA 30 in communication with the COW 1014. Alternatively or additionally, the COW 1014 and devices 12 can be grouped together in close enough proximity for the COW 1014 to acquire data from all of the devices 12 via the associated MDA's 30 for a particular patient.

It is contemplated by this disclosure that the COW 1014 may pull up a particular patient's electronic medical record automatically upon entering a patient's room and establishing communications with MDA's 30 for the particular patient or based on communications between the COW 1014 (such as via a tracking tag attached thereto) and locating and tracking system 70. Alternatively, a caregiver can pull up a patient's electronic medical record on COW 1014 manually. Once the patient's electronic medical record is opened on COW 1014, then some or all of the data received from devices 12 via MDA's 30 populate the patient's electronic medical record in the corresponding fields and the caregiver may enter data into other fields of the patient's electronic medical record. That is, this disclosure contemplates that there may be some patient data that does not automatically get entered into the patient's electronic medical record. Such data could, for example, be data on one or more devices 12 that do not have an associated MDA 30 or such data could be data, such as a patient's temperature or blood pressure, that is not being monitored by any of devices 12 for a particular patient and that the nurse obtains herself while visiting the patient.

Circuit schematics of one embodiment of electric circuit implementations of local data collection module 14, MDA 30, beacon module 110, and BLM 31 are provided in U.S. Provisional Patent Application No. 61/106,830 which was filed Oct. 20, 2008 and which is hereby expressly incorporated herein by reference in its entirety for all that it teaches, including the circuit schematics just mentioned which appear in FIGS. 30A-33D of the referenced provisional. U.S. Provisional Patent Application No. 61/106,830 will become publicly available electronically (i.e., published) on the Public PAIR database of the USPTO website upon the publication of the present U.S. utility patent application. In one embodiment, module 14 is Tridium, Inc. part number HT-BAH-BDH000; MDA 30 is Tridium, Inc. part number HR-BAH-MDA000; beacon module 110 is Tridium, Inc. part number HR-BAH-PBM000; BLM 31 is Tridium, Inc. part number HR-BAH-BLM000; and display 60 is Tridium, Inc. part number HR-BAH-HDM000.

Based on the description herein, it can be appreciated that systems 10, 200 provide centralized technology solutions that wirelessly captures and integrates key patient data from devices 12, including patient monitoring medical devices, and makes the data available to the EMR 72. This is accomplished in illustrative embodiments using MDA's 30 in conjunction with module 14 or wall hub 1460. The MDA's have RF and ultrasound receivers which receive wireless RF and ultrasound signals, respectively, from a beacon module 110 to allow for association of the MDA's 30 and devices 12 to a particular bed 40 or patient associated with a bed 40. The beds 40 may have BLM's 31 having RF and ultrasound receivers similar to those of the MDA's for this same association purpose.

In a variant embodiment, module 14 and hub 1460 are omitted and MDA's 30 are configured to communicate directly with Ethernet 24 via wireless access points (WAP's) 22 using a WiFi card that is included in the MDA 30 or separately attached to one of the ports of the MDA's 30, such as the RS-232 ports 34 of the MDA's. The beacon modules 110 and BLM's 31 may still be present in such a variant embodiment for performing their association function. In still another variant embodiment, ultrawide band (UWB) triangulation techniques may be used in lieu of, or in addition to, use of RF and ultrasound signals. In such a system using UWB triangulation, the MDA's 30 and BLM's 31 are equipped with UWB receivers or transceivers, and beacon modules 110 are equipped with UWB transmitters or transceivers. To triangulate the UWB signals, each MDA 30 and/or BLM 31 generally needs to receive a UWB signal from at least two UWB beacon modules, the locations of which are known (i.e., stored in memory) of an association computer. The time of flight of the UWB signals are used to achieve the triangulation calculations.

It is contemplated by this disclosure that MDA's 30 and BLM's 31 may have RF, ultrasound, and UWB receivers or transceivers and that the RF and ultrasound signals may be used for device-to-bed (or patient) association when devices 12 and bed 40 located within a particular patient room and that the UWB signals are used for tracking the movement of the devices 12 and/or bed 40 when they are outside a patient room such as when they are in transit from one location in the healthcare facility to another. Further variants for associating beds 40, patients, and devices 12 of a system contemplated herein include having a radio frequency identification (RFID) reader on the bed for reading (i.e., receiving wireless signals from) an RFID wristband worn by a patient. The RFID reader on the bed may also receive signals from RFID tags or badges worn by caregivers and such data may be provided to bed hub 14 or wall hub 1460, as the case may be. The identification of one or more caregivers who are present in the patient's room when readings from devices 12 and/or bed 40 are transmitted to the EMR, or other remote system, by bed hub 14 or wall hub 1460 may also be stored in the records of the remote system.

According to this disclosure, the number of hours that devices 12 are used or are in service may be tracked by a remote computer based on information transmitted by MDA's 30, bed hub 14 and/or wall hub 1460. In some contemplated embodiments, the remoter computer may be programmed to compare such information to a maintenance or service schedule which is stored in that remote computer or accessed in a different database associated with another computer. Service or maintenance calls can be scheduled by workflow system 76 if the comparison of the hours-in-use data with the maintenance or service schedule indicates that such maintenance or service is needed for a particular device 12, MDA 30, bed hub 14, wall hub 1460, and so on. An example of a needed service, includes calibrating a device 12 after it has been used for some predetermined amount of time.

It also contemplated by this disclosure that the data regarding the number of hours that devices 12 are used or are in service, which as stated above may be tracked by a remote computer based on information transmitted by MDA's 30, bed hub 14 and/or wall hub 1460, may also be used for more accurate patient billing. For example, a patient (or their insurance company) can be billed based on the number of hours or minutes of actual device usage to deliver treatment or therapy to the patient, rather than being billed on a daily basis or other time basis that is not reflective of the precise amount time the device is actually used for patient treatment or therapy. The systems 10, 200 contemplated herein are suitable to accomplish this time usage tracking function automatically, which function would be nearly impossible for caregivers to suitably accomplish manually.

Also according to this disclosure, it is contemplated that information obtained by MDA's, bed hub 14, and/or wall hub 1460 may be useful for facilitating product recalls that may be initiated by a device manufacturer or by a regulatory body, such as the Food and Drug Administration (FDA). Such recalls may sometimes be limited to devices 12 having a particular firmware version or particular manufacturing series or having some other unique identification characteristic that does not necessarily apply to all of the similar types of devices 12 in use in the healthcare facility from a particular manufacturer. Large hospitals sometimes have thousands of pieces equipment of the same general type but having different firmware versions, manufacturing series, manufacturing lot numbers, and so forth. Thus, according to this disclosure, systems 10, 200 are operable to generate reports, such as by using a remote computer of any of systems 70, 72, 74, 76, 78, 80 to pinpoint the precise locations in the healthcare facility of the particular individual devices 12 that are subject to a recall. In some embodiments of such a system capable of generating such recall reports, the particular device identification data needed to create such reports may be stored in bed hub 14 and/or wall hub 1460 and or hub server 206.

In some embodiments, hubs 14, 1460 have the following features or capabilities: PowerPC 440Epx 667 MHz processor; Integral PCI graphics controller, for LCE touch screen support; 1 GB NAND Flash storage, on-board (non-upgradeable); Base 512 MB DDR-2 333 Mhz RAM, field upgradeable to 1 GB (industrial-grade, sourced from Tridium in some embodiments); two (2) Gigabit Ethernet ports; two (2) USB-2.0 ports; a standard RS-232 port; isolated RS-485/power port (usable as a standard non-powered isolated RS-485 port, or with expansion modules); MiniPCI option slot (for WiFi 802.11g support); and two (2) JACE® comm option slots, for LonWorks®, RS-485 or RS-232, GPRS/Edge Cellular, IPv6/Zigbee Pro 802.15.4 wireless, etc. Further, in some embodiments, hubs 14, 1460 are off the shelf products available from Tridium, Inc. and loaded with QNX OS and Niagara Framework software, also available from Tridium. When hub 14 is mounted to, or included in the circuitry of bed 40, hub 14 receives 120 VAC line voltage from the bed which, in turn, receives its power from a standard wall outlet. Hub 14 has circuitry to convert the 120 VAC line voltage to one or more DC voltages for use.

In one embodiment, hubs 14, 1460 are loaded with Cerner Connectivity Module (CMM) software which is available from Cerner Corporation of Kansas City, Mo., which entity is a supplier of EMR systems to hospitals. Thus, it is contemplated by this disclosure that EMR system 72 may be provided to healthcare facility by Cerner and hubs 14, 1460 are configured so as to be compatible with Cerner's EMR system. The Cerner CMM software includes over one hundred (100) device drivers having protocols to obtain and communicate device data.

As alluded to above, hub server 206 acts a communication intermediary between hubs 14, 1460 and other systems, such as ADT and/or EMR systems 72, 74. More particularly, in some embodiments, server 206 handles usage and location data for all the MDA's 30 and hubs 14, 1460, communicates with the ADT and/or EMR systems 72, 74 to associate patients with rooms, and handles administrative tasks, such as security. Server 206 collects all data from hubs 14, 1460 and pushes that data to an interface gateway. The software for day-to-day operation of hubs 14, 1460 is included on server 206 (i.e., stored in a database of server 206 or associated with server 206), with the exception of the BioMed Configuration Station Software, which is loaded onto a separate BioMed Configuration Station. It should be appreciated that the hub server 206 may not be dedicated to only serving hubs 14, 1460, but may also serve other devices connected to Ethernet 24. Furthermore, it is contemplated by this disclosure that, in some embodiments, hub server 206 is loaded with Rhapsody software which is available from Orion Health of Auckland, New Zealand and which performs protocol conversion of messages from one type to another and, in the contemplated embodiments, permits communication between hub server 206 and ADT system 74.

It is contemplated by this disclosure that, in some embodiments, the BioMed Station provides a front-end for BioMed engineers, or other medical staff, to configure and test the MDA's 30; to assign MDA's 30 to particular medical devices 12; to assign beacon modules 110 to particular rooms; to assign displays 60 to particular rooms; and to assign BLM's 31 to particular beds. Any standard personal computer (PC) operating on a Microsoft Windows® platform and a 40 Gigabyte hard drive may be used as the BioMed Station, including laptops that allow the BioMed engineer, or other medical staff, to configure and/or assign MDA's 30, BLM's 31, displays 60 (including displays of wall hub 1460), and beacon modules 110 in a mobile environment (e.g., walking around a healthcare facility and performing the configuration and/or assignment tasks at various locations throughout the facility). In connection with configuring and assigning functions of the BioMed Station, this may be done using component identification data, such as, for example, serial number, Internet Protocol (IP) address, room number and/or bed number, just to name a few.

The interface gateway may comprise a Cerner MDBus® gateway or a gateway of some other party. The interface gateway collects valid data and maps the data to a patient's medical record. With some non-Cerner EMR systems 72, server 206 may route the data directly to the EMR system 72 without the use of an interface gateway. In some embodiments, a standard personal computer (PC) with a Microsoft Windows® platform and a 40 Gigabyte hard drive is used as hub server 206.

As mentioned above, bed hub 14 and wall hub 1460 have device driver software stored thereon or that that is obtainable from a device driver library stored in a database associated with hub server 206. The device driver software allows information from different medical device protocols to be accepted by hubs 14, 1460. In some embodiments, a Broadcom BCM94306 Wireless LAN Mini-PC Adapter Card is used to provide WiFi or Ethernet wireless communications between MDA's 30 and bed hub 14 or wall hub 1460. In systems 10, 200 described herein, bed hubs 14 and 1460 are capable of receiving wireless data from MDA's 30 for at least ten (10) medical devices that are associated with a corresponding patient.

In some embodiments, systems 10, 200 are compatible with (i.e., configured for communication with) the following list of devices 12: Sigma Spectrum infusion devices; Datascope Passport Monitoring devices; Datascope Passport 2 Monitoring devices; GE Eagle 4000 Monitoring devices; GE Dash 4000, 5000, 6000 Monitoring devices; Philips MP50 Monitoring devices; Edward Life Science Vigilance I Monitoring devices; Edward Life Science Vigileo Monitoring devices; Nellcor N600 Pulse Oximeter devices; Respironics Esprit Ventilator devices; Sensormedics 3100A Ventilator devices; Maquet servo i Ventilator devices; Puritan Bennett 840 Ventilator devices; Puritan Bennett 7200 Ventilator devices; Welch Allyn VSM 5300 Vital Signs Monitoring devices; and Hill-Rom TotalCare hospital beds. The foregoing list is not intended to be an exhaustive list of particular devices that may comprise devices 12 of system 10, 200 according to this disclosure. This list is provided to show the wide variety of types of the devices and manufacturers that systems 10, 200 may include and with which MDA's 30 and hubs 14, 1460 are able to communicate.

In some embodiments, bed 40 communicates bed data to bed hub 14 via an Echelon network (e.g., LON) and in other embodiments, bed 40 communicates bed data to bed hub 14 via a Controller Area Network (CAN). Thus, a CAN card is provided in hub 14 in those embodiments having CAN communications between bed 40 and hub 14. In still other embodiments, hub 14 may be mounted on bed 40 and not receive any bed data at all, such that bed 40 simply provides a structure on which hub 14 is mounted.

Although certain illustrative embodiments have been described in detail above, variations and modifications exist within the scope and spirit of this disclosure as described and as defined in the following claims.

The invention claimed is:

1. A method of associating at least one patient care device in a room of a healthcare facility with a first patient in the room which also has a second patient in the room, the method comprising coupling an input port of a medical device adapter to an output port of the patient care device, the medical device adapter using a low power protocol to wirelessly transmit patient data received from the patient care device, the medical device adapter being battery powered by an onboard battery, the medical device adapter enhancing battery life by using power from the patient care device if power is available via the output port of the patient care device, receiving at an association computer wireless location data transmitted wirelessly from the patient care device via the medical device adapter and received by first and second wireless receivers located in the room and positioned near first and second hospital beds assigned to the first and second patients, respectively, the association computer being operable to determine that the patient care device should be associated with the first patient and not with the second patient based upon association rules programming executed by the association computer including rules regarding resolving ambiguities concerning whether the patient care device is to be associated with the first patient or the second patient based on proximity of the patient care device to the first wireless receiver and to the second wireless receiver, prompting a caregiver with a graphical display in the room to provide an input on the graphical display to confirm the association of the patient care device to the first patient, and receiving the input on the graphical display from the caregiver to confirm the association of the patient care device to the first patient, wherein the patient care device comprises one or more of the following: life support equipment, a ventilator, vital signs monitoring equipment, an electrocardiograph (EKG), an electroencephalograph (EEG), a heart rate monitor, a blood pressure monitor, a blood oxygen saturation monitor, an intravenous (IV) pump, a drug infusion pump, an insulin pump, or a passive motion device.

2. The method of claim 1, wherein the graphical display comprises part of the association computer.

3. The method of claim 1, wherein the graphical display is coupled to a hospital bed and the association computer is remote from the hospital bed.

4. The method of claim 1, wherein the graphical display is coupled to a room wall and the association computer is remote from the room wall.

5. The method of claim 1, wherein the graphical display is coupled to a headwall that is coupled to a room wall and the association computer is remote from the headwall.

6. The method of claim 1, wherein transmitting wireless location data from the patient care device comprises transmitting wireless location data from at least one location tag coupled to the patient care device.

7. The method of claim 1, wherein transmitting wireless location data from the patient care device comprises transmitting wireless location data from a data communication module attached to the patient care device.

8. The method of claim 7, further comprising transmitting device data received by the data communication module from the patient care device to a data collection computer.

9. The method of claim 1, wherein transmitting wireless location data from the patient care device to an association computer comprises transmitting wireless location data via an Ethernet of a healthcare facility.

10. The method of claim 1, further comprising determining a time of flight of the wireless location data from the patient care device to the wireless receiver located in the room.

11. The method of claim 10, wherein the association rules programming of the association computer uses the time of flight in determining that the patient care device should be associated with the first patient.

12. The method of claim 1, further comprising receiving at the association computer a disassociate message after the association has been confirmed, the disassociate message resulting in the association computer disassociating the patient care device from the first patient.

13. The method of claim 12, wherein the disassociate message is transmitted in response to a disassociate input being selected by a caregiver.

14. The method of claim 13, wherein the disassociate input is selected by the caregiver by pressing a button on a data communication module attached to the patient care device.

15. The method of claim 1, further comprising displaying the first patient's name and a name of the patient care device on the graphical display.

16. The method of claim 15, wherein the first patient's name appears on the graphical display in a format that maintains confidentiality of an identity of the first patient.

17. The method of claim 15, wherein a status indicia appears on the graphical display screen to indicate that data is currently being received from the patient care device by a local computer in the room.

18. The method of claim 17, further comprising transmitting the data from the local computer to a computer of an Electronic Medical Records (EMR) system.

19. The method of claim 17, further comprising displaying a message on the graphical display in response to communication between the patient care device and the local computer being lost.

20. The method of claim 15, wherein a status indicia appears on the graphical display screen to indicate that an alarm condition is sensed by the patient care device.

* * * * *